(12) United States Patent
Ebright et al.

(10) Patent No.: US 10,450,292 B2
(45) Date of Patent: Oct. 22, 2019

(54) INHIBITORS OF BACTERIAL RNA POLYMERASE: ARYLPROPANOYL, ARYLPROPENOYL, AND ARYLCYCLOPROPANECARBOXYL PHLOROGLUCINOLS

(71) Applicant: Rutgers, The State University of New Jersey, New Brunswick, NJ (US)

(72) Inventors: Richard H. Ebright, New Brunswick, NJ (US); Joel Freundlich, New Brunswick, NJ (US); Nisha Mittal, New Brunswick, NJ (US); Mark Jaskowski, New Brunswick, NJ (US); Juan Shen, New Brunswick, NJ (US)

(73) Assignee: Rutgers, The State University of New Jersesy, New Brunswick, NJ (US)

( * ) Notice: Subject to any disclaimer, the term of this patent is extended or adjusted under 35 U.S.C. 154(b) by 0 days.

(21) Appl. No.: 15/782,002

(22) PCT Filed: Dec. 9, 2016

(86) PCT No.: PCT/US2016/065931
§ 371 (c)(1),
(2) Date: Jun. 6, 2018

(87) PCT Pub. No.: WO2017/100645
PCT Pub. Date: Jun. 15, 2017

(65) Prior Publication Data
US 2019/0023682 A1    Jan. 24, 2019

Related U.S. Application Data

(60) Provisional application No. 62/265,881, filed on Dec. 10, 2015.

(51) Int. Cl.
| | | |
|---|---|---|
| *C07D 333/22* | (2006.01) | |
| *A61K 31/12* | (2006.01) | |
| *A61K 31/381* | (2006.01) | |
| *C07C 49/753* | (2006.01) | |
| *C07C 49/83* | (2006.01) | |
| *C07C 49/835* | (2006.01) | |
| *C07C 49/84* | (2006.01) | |
| *C07D 213/64* | (2006.01) | |
| *C07D 213/643* | (2006.01) | |
| *A61P 31/04* | (2006.01) | |

(52) U.S. Cl.
CPC ............ *C07D 333/22* (2013.01); *A61K 31/12* (2013.01); *A61K 31/381* (2013.01); *A61P 31/04* (2018.01); *C07C 49/753* (2013.01); *C07C 49/83* (2013.01); *C07C 49/835* (2013.01); *C07C 49/84* (2013.01); *C07D 213/64* (2013.01); *C07D 213/643* (2013.01); *C07C 2601/02* (2017.05); *C07C 2601/16* (2017.05)

(58) Field of Classification Search
CPC ............... C07D 333/22; C07D 213/64; C07D 213/643; A61P 31/04; A61K 31/12; A61K 31/381; C07C 49/753; C07C 49/83; C07C 49/835; C07C 49/84
USPC ......................................................... 549/29
See application file for complete search history.

(56) References Cited

U.S. PATENT DOCUMENTS

| | | |
|---|---|---|
| 2,898,374 A | 8/1959 | Riedl |
| 4,061,769 A | 12/1977 | Ohno et al. |
| 4,421,763 A | 12/1983 | Hamano et al. |
| 5,411,728 A | 5/1995 | Joulain et al. |
| 6,022,983 A | 2/2000 | Wuonola et al. |
| 6,169,181 B1 | 1/2001 | Romines et al. |
| 6,191,288 B1 | 2/2001 | Ramamoorthy |
| 6,228,882 B1 | 5/2001 | Wuonola et al. |
| 8,114,583 B2 | 2/2012 | Ebright et al. |
| 8,772,332 B2 | 7/2014 | Ebright et al. |
| 9,517,994 B2* | 12/2016 | Ebright ................... C07C 49/83 |
| 2003/0065039 A1 | 4/2003 | Kharazmi et al. |
| 2005/0187170 A1 | 8/2005 | Bantia et al. |
| 2006/0100291 A1 | 5/2006 | Perry et al. |
| 2007/0292355 A1 | 12/2007 | Tamarkin et al. |
| 2008/0039511 A1* | 2/2008 | Takemura ............ C07D 277/24 514/365 |
| 2013/0237595 A1 | 9/2013 | Ebright et al. |
| 2013/0289128 A1* | 10/2013 | Ebright ................. C07C 49/747 514/683 |
| 2015/0011647 A1 | 1/2015 | Ebright et al. |
| 2015/0031640 A1 | 1/2015 | Ebright et al. |

(Continued)

FOREIGN PATENT DOCUMENTS

| | | |
|---|---|---|
| CN | 105085219 | * 11/2015 |
| EP | 1764363 | * 3/2007 |

(Continued)

OTHER PUBLICATIONS

Boccard; European Journal of Pharmaceutical Sciences (2009), 36, 254-264. (Year: 2009).*

(Continued)

*Primary Examiner* — Daniel R Carcanague

(74) *Attorney, Agent, or Firm* — Viksnins Harris Padys Malen LLP

(57) ABSTRACT

The invention provides compounds that are inhibitors of bacterial RNA polymerase. The invention also provides compositions comprising such compounds, methods of making such compounds, and methods of using said compounds. The invention has applications in control of bacterial gene expression, control of bacterial growth, antibacterial chemistry, and antibacterial therapy.

14 Claims, 2 Drawing Sheets

(56) References Cited

U.S. PATENT DOCUMENTS

| | | | |
|---|---|---|---|
| 2015/0051275 A1 | | 2/2015 | Ebright et al. |
| 2015/0197512 A1* | | 7/2015 | Ebright ............... C07D 309/38 514/326 |

FOREIGN PATENT DOCUMENTS

| | | | | |
|---|---|---|---|---|
| JP | 09301915 | * | 11/1997 | |
| JP | H10324657 A | | 12/1998 | |
| WO | 1998052899 A1 | | 11/1998 | |
| WO | 2007094799 A1 | | 8/2007 | |
| WO | 2012033846 A1 | | 3/2012 | |
| WO | 2012037508 A2 | | 3/2012 | |
| WO | WO-2013103969 A1 | * | 7/2013 | ............. C07C 49/83 |
| WO | 2013119564 A1 | | 8/2013 | |
| WO | 2013142812 A1 | | 9/2013 | |
| WO | 2013192352 A1 | | 12/2013 | |

OTHER PUBLICATIONS

Bois; J. Med. Chem. 1998, 41, 4161-4164. (Year: 1998).*
Bois; Bioorganic & Medicinal Chemistry 1999, 7, 2691-2695. (Year: 1999).*
Bu; J. Nat. Prod. 1996, 59, 968-969. (Year: 1996).*
Dong; Bioorganic & Medicinal Chemistry 2008, 16, 8151-8160. (Year: 2008).*
Dong; Arch. Pharm. Chem. Life Sci. 2009,342, 428-432. (Year: 2009).*
Sun; Chem Biol Drug Des 2012, 80, 584-590. (Year: 2012).*
Zhao; Bioorganic & Medicinal Chemistry Letters 2005, 15, 5027-5029. (Year: 2005).*
Andre, et al., "Novel synthetic molecules targeting the bacterial RNA polymerase assembly", Journal of Antimicrobial Chemotherapy, 57, 245-251 (2006).
Chatterjee, et al., "Isolation and structure of archangelenone. Flavonoid constituent of Angelica archangelica", XP002692911, Database Caplus [Online] Chemical Abstracts accession No. 1973:489536.
Doundoulakis, et al., "Myxopyronin B analogs as inhibitors of RNA polymerase, synthesis and biological evaluation", Bioorganic and Medicinal Chemistry Letters, vol. 14 (22), 5667-5672 (2004).
Doundoulakis, et al., "Myxopyronin B analogs as inhibitors of RNA polymerase, synthesis and biological evaluation", HCAPLUS Accession No. 2004:863124, 5 pages, Bioorganic & Medicinal Chemistry Letters, 14(22), 5667-5672 (2004).
Hu, "Total syntheses of biologically active natural products: motuporin, oleandolide, (±)—myxopyronin A and B", HCAPLUS Accession No. 2000:514322, 1 page, Diss. Abstr. Int., B 2000, 60(10), 5094.
Iinuma, et al., "Structure-Activity Correlation of Flavonoids for Inhibition of Bovine Lens Aldose Reductase", Chem Pharm Bull 37(7), 1813-181 (1989).
Lira, et al., "Syntheses of novel myxopyronin B analogs as potential inhibitors of bacterial RNA polymerase", Bioorganic & Medicinal Chemistry Letters 17(24), 6797-6800 (2007).
Mapunya, et al., "Tyrosinase activity of Greyia flanaganii (Bolus) constituents", Phytomedicine 18, 1006-1012 (2011).
Mukhopadhyay, et al., "The RNA polymerase "switch region" is a target for inhibitors", Cell 135, 295-307 (2008).
Mukhopadhyay, et al., "The RNA polymerase "switch region" is a target for inhbitiors", HCAPLUS Accession No. 2008:1312023, 2 pages, Cell 135(2), 295-307 (2008).
Patent Cooperation Treaty, International Searching Authority, Search Report and Written Opinion for PCT/2016/065931, 11 pages, dated May 30, 2017.
Pubchem, "Chembl487037", CID 44562517, U.S. National Library of Medicine, p. 1-12 (2010).
Srivastava, et al., "New Target for Inhibition of Bacterial RNA Polymerase: Switch Region", Curr. Opin. Microbiol. 14, 532-543 (2011).
Werner, et al., "Synthesis of non-natural flavanones and dihydrochalcones in metabolically engineered yeast", Journal of Molecular Catalysis B: Enzymatic 66, 257-263 (2010).

* cited by examiner

INHIBITORS OF BACTERIAL RNA POLYMERASE: ARYLPROPANOYL, ARYLPROPENOYL, AND ARYLCYCLOPROPANECARBOXYL PHLOROGLUCINOLS

This application is a U.S.C. § 371 application of International Application No. PCT/US2016/065931, filed Dec. 9, 2016, which claims the benefit of priority to U.S. Provisional Application No. 62/265,881, filed Dec. 10, 2015.

GOVERNMENT SUPPORT

This invention was made with Government support under U19-AI109713 awarded by the National Institutes of Health. The government has certain rights in the invention.

BACKGROUND

Bacterial infections remain among the most common and deadly causes of human disease. Infectious diseases are the third leading cause of death in the United States and the leading cause of death worldwide (Binder et al. (1999) *Science* 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) *Nature* 406, 775-781; Schluger, N. (2000) *Int. J. Tuberculosis Lung Disease* 4, S71-S75; Raviglione et al., (2001) *Ann. NY Acad. Sci.* 953, 88-97). New approaches to drug development are necessary to combat the ever-increasing number of antibiotic-resistant pathogens.

RNA polymerase (RNAP) is the molecular machine responsible for transcription and is the target, directly or indirectly, of most regulation of gene expression (Ebright, R. (2000) *J. Mol. Biol.* 304, 687-698; Darst, S. (2001) *Curr. Opin. Structl. Biol.* 11, 155-162; Murakami, K. and Darst, S. (2003) *Curr. Opin. Structl. Biol.* 13, 31-39; Borukhov, S. and Nudler, E. (2003) *Curr. Opin. Microbiol.* 6, 93-100; Werner, F. (2007) *Mol. Microbiol.* 65, 1395-1404; Hirata, A. and Murakami, K. (2009) *Curr. Opin. Structl. Biol.* 19, 724-731; Jun, S., Reichlen, M., Tajiri, M. and Murakami, K. (2011) *Crit. Rev. Biochem. Mol. Biol.* 46, 27-40; Cramer, P. (2002) *Curr. Opin. Struct. Biol.* 12, 89-97; Cramer, P. (2004) *Curr. Opin. Genet. Dev.* 14, 218-226; Hahn, S. (2004) *Nature Struct. Mol. Biol.* 11, 394-403; Kornberg, R. (2007) *Proc. Natl. Acad. Sci. USA* 104, 12955-12961; Cramer, P., Armache, K., Baumli, S., Benkert, S., Brueckner, F., Buchen, C., Damsma, G., Dengl, S., Geiger, S., Jasiak, A., Jawhari, A., Jennebach, S., Kamenski, T., Kettenberger, Kuhn, C., Lehmann, E., Leike, K., Sydow, J. and Vannini, A. (2008) *Annu. Rev. Biophys.* 37, 337-352; Lane, W. and Darst, S. (2010) *J. Mol. Biol.* 395, 671-685; Lane, W. and Darst, S. (2010) *J. Mol. Biol.* 395, 686-704; Werner, F. and Grohmann, D. (2011) *Nature Rev. Microbiol.* 9, 85-98; Vannini, A. and Cramer, P. (2012) *Mol. Cell* 45, 439-446). Bacterial RNAP core enzyme has a molecular mass of ~380,000 Da and consists of one β' subunit, one β subunit, two α subunits, and one ω subunit; bacterial RNAP holoenzyme has a molecular mass of ~450,000 Da and consists of bacterial RNAP core enzyme in complex with the transcription initiation factor σ (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami and Darst (2003) *Curr. Opin. Structl. Biol.* 13, 31-39; Borukhov and Nudler (2003) *Curr. Opin. Microbiol.* 6, 93-100). Bacterial RNAP core subunit sequences are conserved across Gram-positive and Gram-negative bacterial species (Ebright, R. (2000) *J. Mol. Biol.* 304, 687-698; Darst, S. (2001) *Curr. Opin. Structl. Biol.* 11, 155-162; Lane, W. and Darst, S. (2010) *J. Mol. Biol.* 395, 671-685; Lane, W. and Darst, S. (2010) *J. Mol. Biol.* 395, 686-704). Eukaryotic RNAP I, RNAP II, and RNAP III contain counterparts of all bacterial RNAP core subunits, but eukaryotic-subunit sequences and bacterial-subunit sequences exhibit only limited conservation (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Cramer, P. (2004) *Curr. Opin. Genet. Dev.* 14, 218-226; Lane, W. and Darst, S. (2010) *J. Mol. Biol.* 395, 671-685; Lane, W. and Darst, S. (2010) *J. Mol. Biol.* 395, 686-704).

Crystal structures have been determined for bacterial RNAP and eukaryotic RNAP II (Zhang et al., (1999) *Cell* 98, 811-824; Cramer et al., (2000) *Science* 288, 640-649; Cramer et al., (2001) *Science* 292, 1863-1876).

Structures also have been determined for RNAP complexes with nucleic acids, nucleotides and inhibitors (Campbell, et al. (2001) *Cell* 104, 901-912; Artsimovitch, et al. (2005) *Cell* 122, 351-363; Campbell, et al. (2005) *EMBO J.* 24, 674-682; Tuske, et al. (2005) *Cell* 122, 541-522; Temiaov, et al. (2005) *Mol. Cell* 19, 655-666; Mukhopadhyay, J., Das, K., Ismail, S., Koppstein, D., Jang, M., Hudson, B., Sarafianos, S., Tuske, S., Patel, J., Jansen, R., Irschik, H., Arnold, E., and Ebright, R. (2008) *Cell* 135, 295-307; Belogurov, G., Vassylyeva, M., Sevostyanova, A., Appleman, J., Xiang, A., Lira, R., Webber, S., Klyuyev, S., Nudler, E., Artsimovitch, I., and Vassylyev, D. (2009) *Nature*. 45, 332-335; Vassylyev, D., Vassylyeva, M., Perederina, A., Tahirov, T. and Artsimovitch, I. (2007) *Nature* 448, 157-162; Vassylyev, D., Vassylyeva, M., Zhang, J., Palangat, M., Artsimovitch, I. and Landick, R. (2007) *Nature* 448, 163-168; Gnatt, et al. (2001) *Science* 292, 1876-1882; Westover, et al. (2004a) *Science* 303, 1014-1016; Westover, et al. (2004b) *Cell* 119, 481-489; Ketenberger, et al. (2004) *Mol. Cell* 16, 955-965; Bushnell, et al. (2002) *Proc. Natl. Acad. Sci. U.S.A.* 99, 1218-1222; Kettenberger, et al. (2005) *Natl. Structl. Mol. Biol.* 13, 44-48; Ho, M., Hudson, B., Das, K., Arnold, E. and Ebright, R. (2009) *Curr. Opin. Structl. Biol.* 19, 715-723).

Bacterial RNAP is a proven target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. and Leonetti, J. (2007) *Drug Discov. Today* 12, 200-208; Mariani, R. and Maffioli, S. (2009) *Curr. Med. Chem.* 16, 430-454; Ho, M., Hudson, B., Das, K., Arnold, E. and Ebright, R. (2009) *Curr. Opin. Structl. Biol.* 19, 715-723; Srivastava, A., Talaue, M., Liu, S., Degen, D., Ebright, R. Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N. and Ebright, R. H. (2011) *Curr. Opin. Microbiol.* 14, 532-543). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampin, rifapentine, and rifabutin—function by binding to and inhibiting bacterial RNAP (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912; Artsimovitch, et al. (2005) *Cell* 122, 351-363; Feklistov, A., Mekler, V., Jiang, Q., Westblade, L., Irschik, H., Jansen, R., Mustaev, A., Darst, S., and Ebright, R. (2008) *Proc. Natl. Acad. Sci. USA* 105, 14820-14825). The rifamycins bind to a site on bacterial RNAP adjacent to the RNAP active center and prevent the extension of RNA chains beyond a length of 2-3 nt.

The rifamycins are in current clinical use in treatment of Gram-positive and Gram-negative bacterial infections (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912). The rifamycins are first-line treatments for tuberculosis and are the only current first-line treatments for tuberculosis able to kill non-replicating tuberculosis bacteria, to clear infection, and to prevent relapse (Mitchison, D. (2000) *Int. J Tuberc. Lung Dis.* 4, 796-806). The rifamycins also are first-line treatments for biofilm-associated infections of catheters and implanted medical devices and are among the very few current antibacterial drugs able to kill non-replicating biofilm-associated bacteria (Obst, G., Gagnon, R. F., Prentis, J. and Richards, G. K. (1988) *ASAIO Trans.* 34, 782-784; Obst, G., Gagnon, R. F., Harris, A., Prentis, J. and Richards, G. K. (1989) *Am. J. Nephrol.* 9, 414-420; Villain-Guillot, P., Gualtieri, M., Bastide, L. and Leonetti, J. P. (2007) *Antimicrob. Agents Chemother.* 51, 3117-3121.

The clinical utility of the rifamycin antibacterial agents is threatened by the emergence and spread of bacterial strains resistant to known rifamycins (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912). Resistance to rifamycins typically involves substitution of residues in or immediately adjacent to the rifamycin binding site on bacterial RNAP—i.e., substitutions that directly decrease binding of rifamycins. A significant and increasing percentage of cases of tuberculosis are resistant to rifampicin (1.4% of new cases, 8.7% of previously treated cases, and 100% of cases designated multidrug-resistant, in 1999-2002; Schluger, N. (2000) *Int. J. Tuberc. Lung Dis.* 4, S71-S75; Raviglione, et al. (2001) *Ann. N Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Antituberculosis drug resistance in the world: third global report* (WHO, Geneva)). Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant bacterial infections, there is an urgent need for new antibacterial agents that target bacterial RNAP and an especially urgent need for new antibacterial agents that target bacterial RNAP derivatives resistant to known rifamycins. (See Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. and Leonetti, J. (2007) *Drug Discov. Today* 12, 200-208; Mariani, R. and Maffioli, S. (2009) *Curr. Med. Chem.* 16, 430-454; Ho, M., Hudson, B., Das, K., Arnold, E. and Ebright, R. (2009) *Curr. Opin. Structl. Biol.* 19, 715-723; Srivastava, A., Talaue, M., Liu, S., Degen, D., Ebright, R. Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N. and Ebright, R. H. (2011) *Curr. Opin. Microbiol.* 14, 532-543.)

SUMMARY

The invention provides new compositions of matter—arylpropanoyl phloroglucinols (APPs), arylpropenoyl phloroglucinols (APPUs), and arylcyclopropanecarboxyl phloroglucinols (APPCs)—that inhibit bacterial RNA polymerase and inhibit bacterial growth.

Compounds of the invention differ from previously disclosed arylpropanoyl phloroglucinols with RNAP-inhibitory and antibacterial activities by having a different substituted aryl or heteroaryl moiety and/or a different linker between the aryl or heteroaryl moiety and the phloroglucinol-derived moiety.

It has been determined—surprisingly—that even large substitutions at the "para" position of the aryl or heteroaryl moiety can be tolerated without loss of RNA-polymerase-inhibitory and antibacterial activities.

It has been determined—surprisingly—that the linker between the aryl or heteroaryl moiety and the phloroglucinol-derived moiety can be replaced by a conformationally constrained, olefinic or cyclic linker without loss of RNA-polymerase-inhibitory and antibacterial activities.

Certain compounds of this invention exhibit higher RNA-polymerase-inhibitory and antibacterial potencies than previously disclosed arylpropanoyl phloroglucinols.

Certain compounds of this invention exhibit higher metabolic stabilities than previously disclosed arylpropanoyl phloroglucinols.

Certain compounds of this invention exhibit lower plasma protein binding than previously disclosed arylpropanoyl phloroglucinols.

Certain compounds of this invention exhibit potent RNA-polymerase-inhibitory activities (micromolar and submicromolar IC50s) and potent antibacterial activities (micromolar and submicromolar MICs).

It is believed that compounds of this invention function by binding to the "switch region" of RNA polymerase.

It is believed that compounds of this invention function by binding to the "switch region SW1/SW2 subregion" of RNA polymerase. Applicants have determined crystal structures of complexes containing RNA polymerase and compounds of the invention (FIGS. 1-2). Crystals were obtained by soaking 2 (FIG. 1; Table 1) or 4 (FIG. 2; Table 1) into pre-formed crystals of a complex of *Escherichia coli* RNA polymerase $\sigma^{70}$ holoenzyme. X-ray diffraction data were collected at a synchrotron light source, structures were solved by molecular replacement, using a previously determined structure of *Escherichia coli* RNA polymerase $\sigma^{70}$ holoenzyme as the search model, and structures were refined to a resolution of 3.8 Å and an $R_{free}$ of 0.29 (2; FIG. 1) and a resolution of 4.0 Å and an $R_{free}$ of 0.30 (4; FIG. 2).

The structures indicate that compounds of the invention bind to the RNA polymerase switch region SW1/SW2 subregion in a position and orientation generally similar to the binding position and binding orientation of previously disclosed arylpropanoyl phloroglucinols.

This invention provides crystal structures of a complex containing RNA polymerase and 2 and a complex containing RNA polymerase and 4.

Compounds of this invention are anticipated to have applications in analysis of RNA polymerase structure and function, control of bacterial gene expression, control of bacterial growth, antibacterial chemistry, antibacterial therapy, and drug discovery.

In one embodiment the invention provides a compound of the invention which is a compound selected from compounds of structural formulae (I)-(VI):

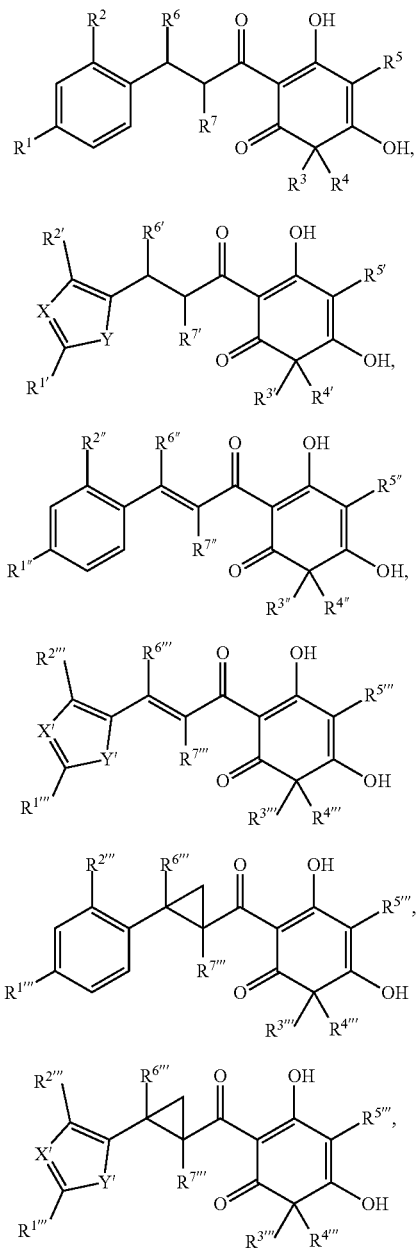

and tautomers and salts thereof, wherein:

$R^2$, $R^6$, and $R^7$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^1$ is fluoromethyl, difluoromethyl, fluoroethyl, difluoroethyl, trifluoroethyl, fluoropropyl, difluoropropyl, trifluoropropyl, fluoromethoxy, difluoromethoxy, fluoroethoxy, difluoroethoxy, trifluoroethoxy, fluoropropoxy, difluoropropoxy, trifluoropropoxy, alkaryl, alkheteroaryl, aryloxy, heteroaryloxy, or benzyloxy, which alkaryl, alkheteroaryl, aryloxy, heteroarlyoxy, or benzyloxy is substituted by one or more of halo, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^3$, $R^4$, and $R^5$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, —$NR^aR^b$, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, $(C_1-C_7)C(=O)NH—$, aryl, heteroaryl, aryloxy, and heteroaryloxy; $R^a$ and $R^b$ each independently is H or $(C_1-C_6)$alkyl, or $R^a$ and $R^b$, together with the nitrogen to which they are attached, form a morpholino, piperazino, pyrrolidino, or piperidino; and at least one of $R^3$, $R^4$, and $R^5$ is other than H; or $R^1$ is $(C_2-C_8)$alkenyl, alkaryl, alkheteroaryl, aryloxy, heteroaryloxy, or benzyloxy, which $(C_2-C_8)$alkenyl, alkaryl, alkheteroaryl, aryloxy, heteroarlyoxy, or benzyloxy optionally is substituted by one or more of halo, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, or heteroaryloxy; and $R^3$, $R^4$, and $R^5$ each is H;

X and Y are individually carbon, sulfur, oxygen, or nitrogen, wherein at least one of X and Y is other than carbon;

$R^{2'}$, $R^{6'}$, and $R^{7'}$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^{1'}$ is halo, $(C_1-C_8)$alkyl, $(C_2-C_8)$alkenyl, $(C_1-C_8)$alkoxy, aryl, heteroaryl, alkaryl, alkheteroaryl, aryloxy, heteroaryloxy, or benzyloxy, which $(C_1-C_8)$alkyl, $(C_2-C_8)$alkenyl, $(C_1-C_8)$alkoxy, aryl, heteroaryl, alkaryl, alkheteroaryl, aryloxy, heteroaryloxy, or benzyloxy optionally is substituted with one or more of halo, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy;

$R^{3'}$, $R^{4'}$, and $R^{5'}$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, $(C_1-C_7)C(=O)NH—$, aryl, heteroaryl, aryloxy, and heteroaryloxy; and $R^{a'}$ and $R^{b'}$ each independently is H or $(C_1-C_6)$alkyl, or $R^{a'}$ and $R^{b'}$, together with the nitrogen to which they are attached, form a morpholino, piperazino, pyrrolidino, or piperidino;

$R^{2''}$, $R^{6''}$, and $R^{7''}$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^{1'''}$ is fluoro, bromo, iodo, $(C_2-C_8)$alkyl, $(C_2-C_8)$alkenyl, $(C_2-C_8)$alkoxy, aryl, heteroaryl, alkaryl, alkheteroaryl, aryloxy, heteroaryloxy, or benzyloxy, which $(C_2-C_8)$ alkyl, $(C_2-C_8)$alkenyl, $(C_2-C_8)$alkoxy, aryl, heteroaryl, alkaryl, alkheteroaryl, aryloxy, heteroaryloxy, or benzyloxy optionally is substituted with one or more of halo, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^{3'''}$, $R^{4'''}$, and $R^{5'''}$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, —NR$^{a''}$R$^{b''}$, fluoromethyl, difluoromethyl, trifluoromethyl, fluoromethoxy, difluoromethoxy, trifluoromethoxy, $(C_1-C_8)$alkyl, $(C_2-C_8)$ alkenyl, $(C_1-C_8)$alkoxy, $(C_1-C_7)C(=O)NH$—, aryl, heteroaryl, aryloxy, and heteroaryloxy; R$^{a''}$ and R$^{b''}$ each independently is H or $(C_1-C_6)$alkyl, or R$^{a''}$ and R$^{b''}$, together with the nitrogen to which they are attached, form a morpholino, piperazino, pyrrolidino, or piperidino; and at least one of R$^{3'''}$, R$^{4'''}$, and R$^{5'''}$ is other than H; or $R^{1'''}$ is fluoromethyl, difluoromethyl, trifluoromethyl, fluoroethyl, difluoroethyl, trifluoroethyl, fluoropropyl, difluoropropyl, trifluoropropyl, fluoromethoxy, difluoromethoxy, trifluoromethoxy, fluoroethoxy, difluoroethoxy, trifluoroethoxy, fluoropropoxy, difluoropropoxy, trifluoropropoxy, aryloxy, heteroaryloxy, alkaryl, or alkheteroaryl, which aryloxy, heteroarlyoxy, alkaryl, or alkheteroaryl optionally is substituted by one or more of halo, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$ alkoxy, aryl, heteroaryl, aryloxy, and heteroaryloxy; and $R^{3'''}$, $R^{4'''}$, and $R^{5'''}$ each is H;

X' and Y' are individually carbon, sulfur, oxygen, or nitrogen, wherein at least one of X and Y is other than carbon;

$R^{2'''}$, $R^{6'''}$, and $R^{7'''}$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^{1'''}$ is halo, $(C_1-C_8)$alkyl, $(C_2-C_8)$alkenyl, $(C_1-C_8)$alkoxy, aryl, heteroaryl, alkaryl, alkheteroaryl, aryloxy, heteroaryloxy, or benzyloxy, which $(C_1-C_8)$alkyl, $(C_2-C_8)$ alkenyl, $(C_1-C_8)$alkoxy, aryl, heteroaryl, alkaryl, alkheteroaryl, aryloxy, heteroaryloxy, or benzyloxy optionally is substituted with one or more of halo, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^{3'''}$, $R^{4'''}$, and $R^{5'''}$ each independently is H, halo, $(C_1-C_8)$ alkyl, or $(C_2-C_8)$alkenyl, which $(C_1-C_8)$alkyl, or $(C_2-C_8)$ alkenyl optionally is substituted with one or more of halo, oxo, hydroxy, carboxy, cyano, —NR$^{a'''}$R$^{b'''}$, fluoromethyl, difluoromethyl, trifluoromethyl, fluoromethoxy, difluoromethoxy, trifluoromethoxy, $(C_1-C_8)$alkyl, $(C_2-C_8)$alkenyl, $(C_1-C_8)$alkoxy, $(C_1-C_7)C(=O)NH$—, aryl, heteroaryl, aryloxy, or heteroaryloxy; and R$^{a'''}$ and R$^{b'''}$ each independently is H or $(C_1-C_6)$alkyl, or R$^{a'''}$ and R$^{b'''}$, together with the nitrogen to which they are attached, form a morpholino, piperazino, pyrrolidino, or piperidino.

The invention also provides methods for making a compound of the invention.

The invention also provides an assay for inhibition of a RNA polymerase comprising contacting a bacterial RNA polymerase with a compound of the invention.

The invention also provides an assay for antibacterial activity comprising contacting a bacterial RNA polymerase with a compound of the invention.

The invention also provides a use of a compound of the invention to bind to a bacterial RNA polymerase.

The invention also provides a use of a compound of the invention to inhibit a bacterial RNA polymerase.

The invention also provides a use of a compound of the invention to inhibit bacterial gene expression.

The invention also provides a use of a compound of the invention to inhibit bacterial growth.

The invention also provides a use of a compound of the invention to inhibit a bacterial infection.

The invention also provides a composition comprising a compound of the invention or a pharmaceutically acceptable salt thereof and a pharmaceutically acceptable vehicle.

The invention also provides a method for inhibiting the growth of bacteria comprising contacting the bacteria with a compound of the invention or a salt thereof.

The invention also provides a method for inhibiting a bacterial RNA polymerase comprising contacting the bacterial RNA polymerase with a compound of the invention or a salt thereof.

The invention also provides a method for treating a bacterial infection in a mammal, e.g., a human, comprising administering to the mammal an effective amount of a compound of the invention or a pharmaceutically acceptable salt thereof.

The invention also provides a compound of the invention or a pharmaceutically acceptable salt thereof for use in the prophylactic or therapeutic treatment of a bacterial infection.

The invention also provides the use of a compound of the invention or a pharmaceutically acceptable salt thereof for the preparation of a medicament for treating a bacterial infection in a mammal, e.g., a human.

The invention also provides a compound of the invention or a pharmaceutically acceptable salt thereof for use in medical treatment.

These and other aspects of the present invention will be better appreciated by reference to the following drawings and Detailed Description.

DETAILED DESCRIPTION

Figure 1:
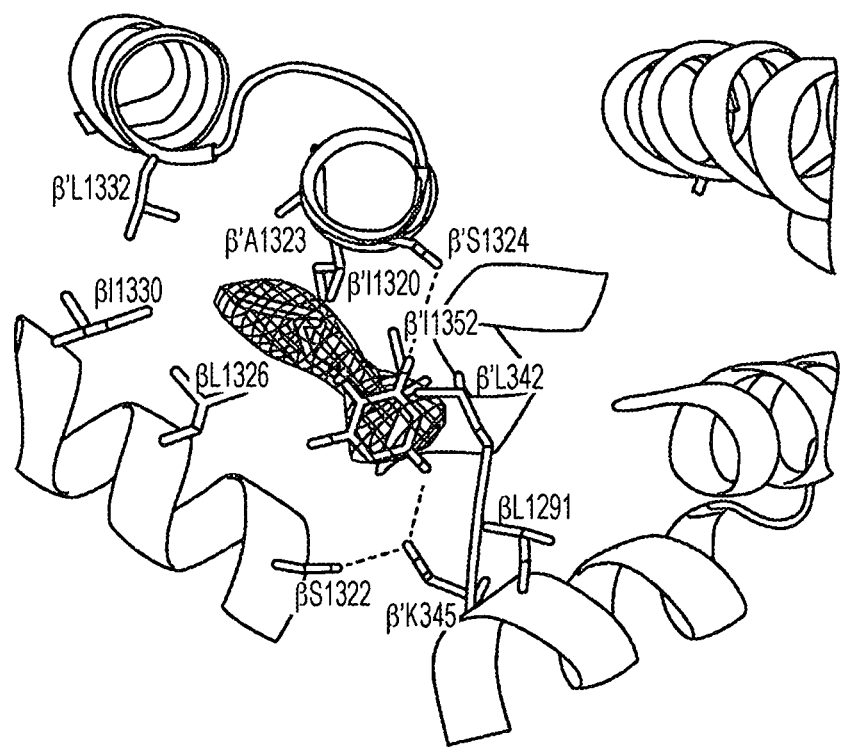
FIG. 1 shows a crystal structure of a complex containing RNA polymerase and 2 (see Detailed Description of the Invention). 2 is in a stick representation in dark gray. Experimental electron density for 2 is indicated as a gray mesh ($F_o$-$F_c$ omit map). RNA polymerase backbone atoms in and near 2 binding site are shown in a ribbon representation in light gray. RNA polymerase sidechain atoms that contact 2 are shown in a stick representation in light gray and are labelled with the RNA polymerase subunit (β or β') and residue number.
Figure 2:
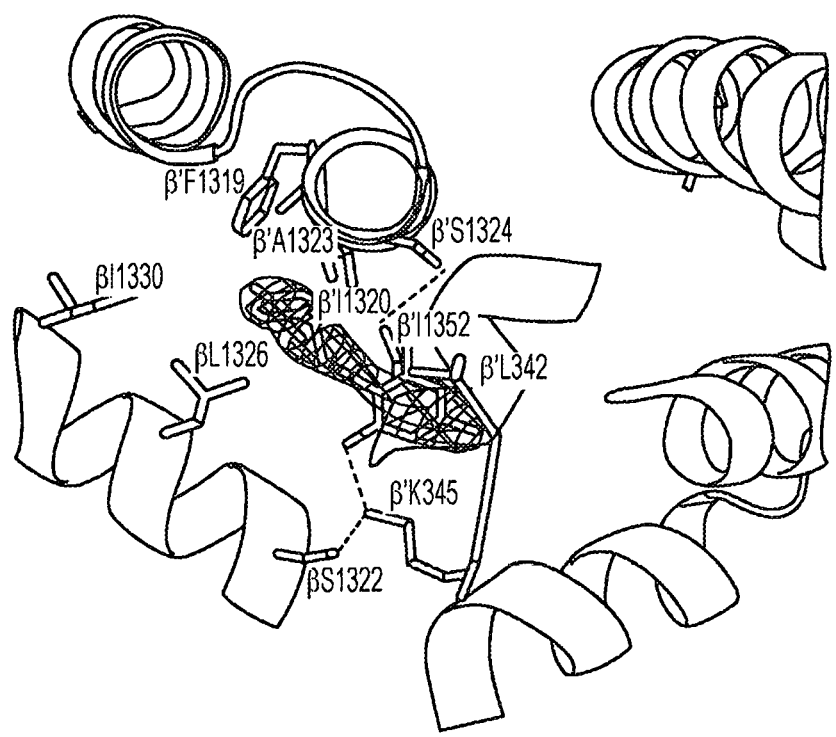
FIG. 2 shows a crystal structure of a complex containing RNA polymerase and 4 (see Detailed Description of the Invention). 4 is in a stick representation in dark gray. Experimental electron density for 4 is indicated as a gray mesh ($F_o$-$F_c$ omit map). RNA polymerase backbone atoms in and near 4 binding site are shown in a ribbon representation in light gray. RNA polymerase sidechain atoms that contact

The following definitions are used, unless otherwise indicated. Halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

Alkaryl refers to a group —$(C_1-C_4)$alkyl-aryl.

Alkheteroaryl refers to a group —$(C_1-C_4)$alkyl-heteroaryl.

Aryloxy refers to a group —O-aryl.

Heteroaryloxy refers to a group —O-heteroaryl.

Unless otherwise specified, the term "binds" used herein refers to high-affinity specific binding (i.e., an interaction for which the equilibrium dissociation constant, Kd, is less than about 100 μM and preferably is less than about 10 μM.

Unless otherwise specified, structures depicted herein are intended to include all stereochemical forms of the structure; i.e., the R and S configurations for each asymmetric center. Therefore, single stereochemical isomers, as well as enantiomeric and diastereomeric mixtures, of the present compounds are within the scope of the invention.

Unless otherwise specified, structures depicted herein are intended to include compounds which differ only in the presence of one or more isotopically enriched atoms. For example, compounds having the present structures, except for the replacement of a hydrogen atom by a deuterium atom or a tritium atom, or except for the replacement of a carbon by a $^{13}$C- or $^{14}$C-enriched carbon atom, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—$(C_1-C_6)$-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Methods to Prepare Compounds of the Invention

Compounds of the invention can be prepared, for example, according to the following synthetic scheme:

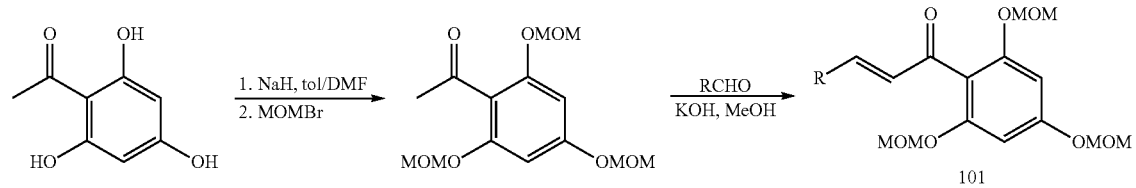

101

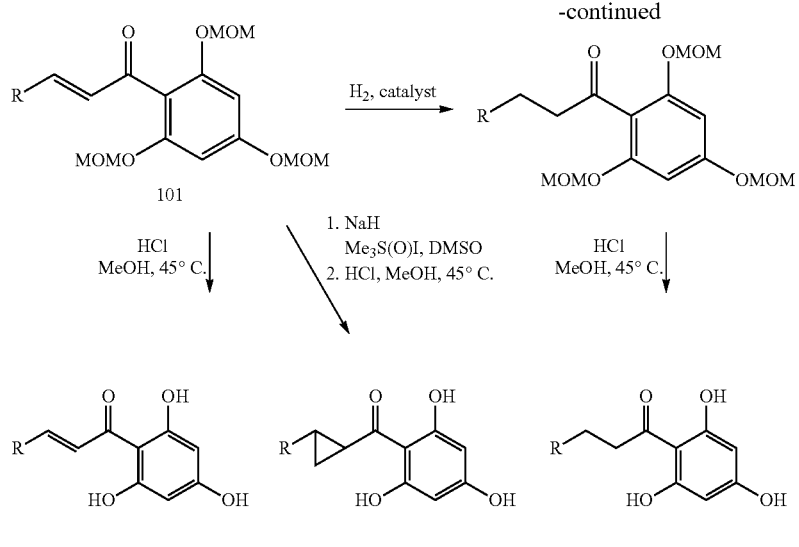

Pharmaceutical Preparations and Methods of Administration

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compound of the invention can be formulated as pharmaceutical compositions and administered to a mammalian host, such as a human patient in a variety of forms adapted to the chosen route of administration, i.e., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compound of the invention can be determined by comparing their in vitro activity, and in vivo activity in animal models.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 100 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

INDUSTRIAL APPLICABILITY

Compounds identified according to the target and method of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

The invention will now be illustrated by the following non-limiting Examples.

EXAMPLES

Preparation of Representative Compounds of the Invention

Using procedures similar to those described in the Scheme above, the following compounds (1-92) were prepared.

TABLE 1
Representative Compounds.
| Example | Structure |
|---|---|
| 1 | 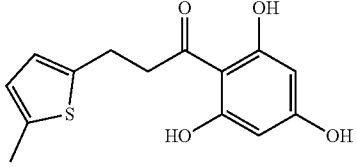 [SMILES: Cc1ccc(CCC(=O)c2c(O)cc(O)cc2O)s1] |
| 2 | 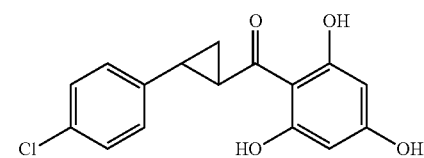 [SMILES: O=C(c1c(O)cc(O)cc1O)C1CC1c1ccc(Cl)cc1] |
| 3 | 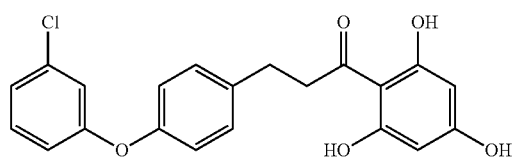 [SMILES: O=C(CCc1ccc(Oc2cccc(Cl)c2)cc1)c1c(O)cc(O)cc1O] |
| 4 | 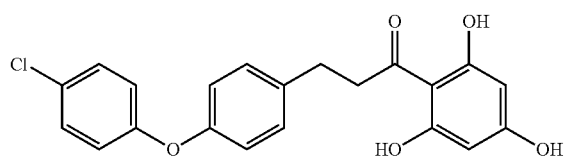 [SMILES: O=C(CCc1ccc(Oc2ccc(Cl)cc2)cc1)c1c(O)cc(O)cc1O] |
| 5 | 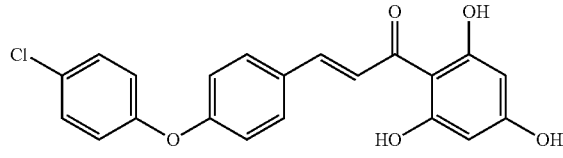 [SMILES: O=C(/C=C/c1ccc(Oc2ccc(Cl)cc2)cc1)c1c(O)cc(O)cc1O] |
| 6 | 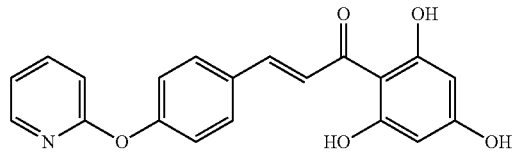 |
| 7 | 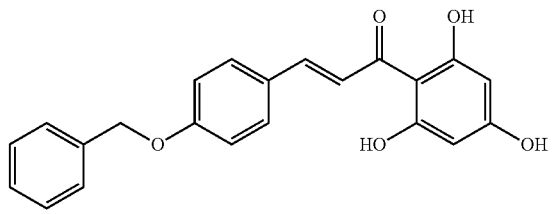 [SMILES: O=C(/C=C/c1ccc(OCc2ccccc2)cc1)c1c(O)cc(O)cc1O] |
| 8 | 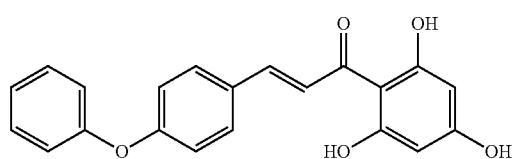 [SMILES: O=C(/C=C/c1ccc(Oc2ccccc2)cc1)c1c(O)cc(O)cc1O] |
| 9 | 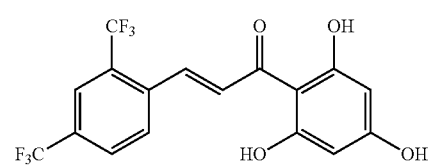 [SMILES: O=C(/C=C/c1ccc(C(F)(F)F)cc1C(F)(F)F)c1c(O)cc(O)cc1O] |

TABLE 1-continued

Representative Compounds.

| Example | Structure |
|---|---|
| 10 | 4-F-C6H4-O-C6H4-CH2CH2-C(O)-C6H2(OH)3 (2,4,6-trihydroxyphenyl ketone with 3-(4-(4-fluorophenoxy)phenyl)propan-1-one) |
| 11 | (E)-1-(2,4,6-trihydroxyphenyl)-3-(4-(4-fluorophenoxy)phenyl)prop-2-en-1-one |
| 12 | cyclopropyl linker: (4-(4-fluorophenoxy)phenyl)cyclopropyl 2,4,6-trihydroxyphenyl ketone |
| 13 | cyclopropyl linker: (4-(4-chlorophenoxy)phenyl)cyclopropyl 2,4,6-trihydroxyphenyl ketone |
| 14 | (E)-1-(2,4,6-trihydroxyphenyl)-3-(4-(trifluoromethyl)phenyl)prop-2-en-1-one |
| 15 | (E)-1-(2,4,6-trihydroxyphenyl)-3-(4-phenoxy-2-(trifluoromethyl)phenyl)prop-2-en-1-one |
| 16 | 1-(2,4,6-trihydroxyphenyl)-3-(4-phenoxy-2-(trifluoromethyl)phenyl)propan-1-one |
| 17 | (E)-1-(2,4,6-trihydroxyphenyl)-3-(4-(4-chlorophenoxy)-2-(trifluoromethyl)phenyl)prop-2-en-1-one |
| 18 | (E)-1-(2,4,6-trihydroxyphenyl)-3-(4-(4-chlorophenoxy)-2-methylphenyl)prop-2-en-1-one |

TABLE 1-continued

Representative Compounds.

| Example | Structure |
|---------|-----------|
| 19 | 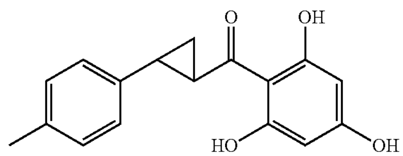 [SMILES: Cc1ccc(C2CC2C(=O)c2c(O)cc(O)cc2O)cc1] |
| 20 | 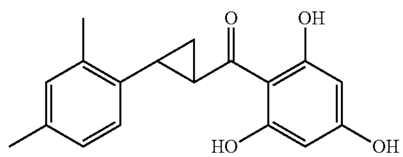 [SMILES: Cc1ccc(C2CC2C(=O)c2c(O)cc(O)cc2O)c(C)c1] |
| 21 | 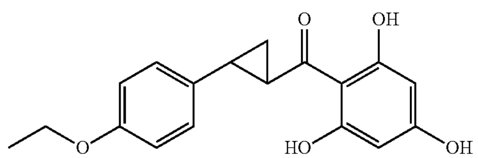 [SMILES: CCOc1ccc(C2CC2C(=O)c2c(O)cc(O)cc2O)cc1] |
| 22 | 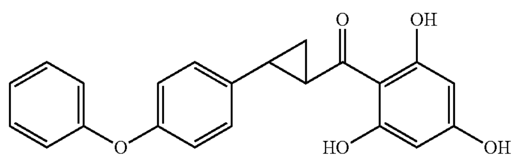 [SMILES: O=C(c1c(O)cc(O)cc1O)C1CC1c1ccc(Oc2ccccc2)cc1] |
| 23 | 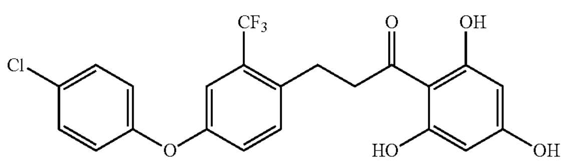 [SMILES: O=C(CCc1ccc(Oc2ccc(Cl)cc2)cc1C(F)(F)F)c1c(O)cc(O)cc1O] |
| 24 | 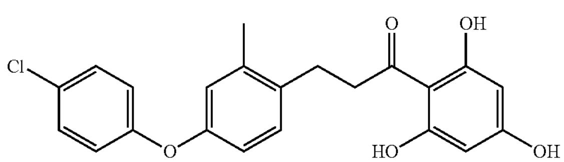 |
| 25 | 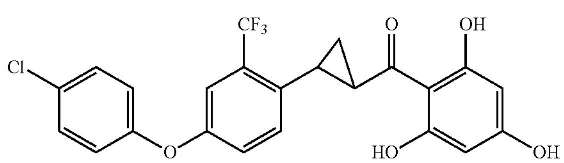 [SMILES: O=C(c1c(O)cc(O)cc1O)C1CC1c1ccc(Oc2ccc(Cl)cc2)cc1C(F)(F)F] |
| 26 | 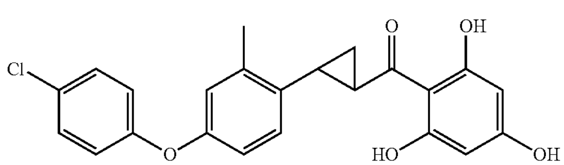 [SMILES: Cc1cc(Oc2ccc(Cl)cc2)ccc1C1CC1C(=O)c1c(O)cc(O)cc1O] |
| 27 | 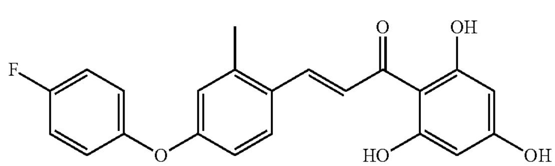 [SMILES: Cc1cc(Oc2ccc(F)cc2)ccc1/C=C/C(=O)c1c(O)cc(O)cc1O] |

TABLE 1-continued
Representative Compounds.
| Example | Structure |
|---|---|
| 28 | 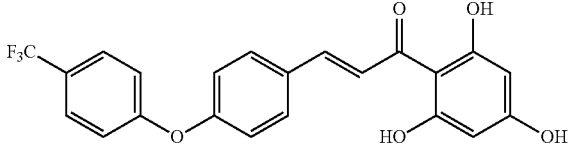 [SMILES: O=C(/C=C/c1ccc(Oc2ccc(C(F)(F)F)cc2)cc1)c1c(O)cc(O)cc1O] |
| 29 | 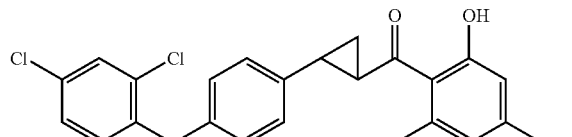 |
| 30 | 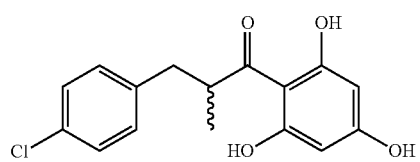 [SMILES: CC(Cc1ccc(Cl)cc1)C(=O)c1c(O)cc(O)cc1O] |
| 31 | 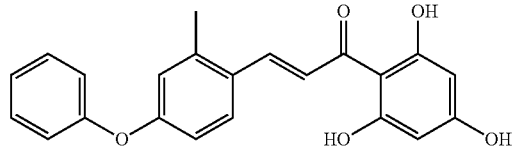 [SMILES: Cc1cc(Oc2ccccc2)ccc1/C=C/C(=O)c1c(O)cc(O)cc1O] |
| 32 | 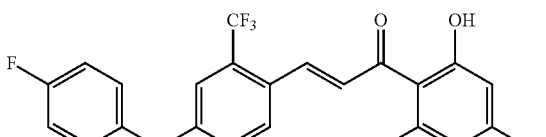 |
| 33 | 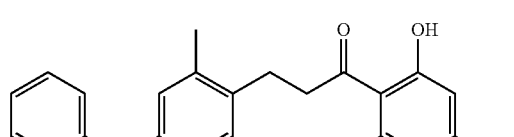 |
| 34 | 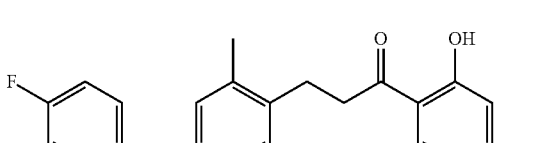 |
| 35 | 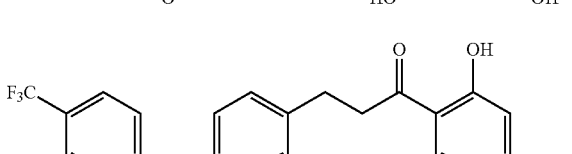 |
| 36 | 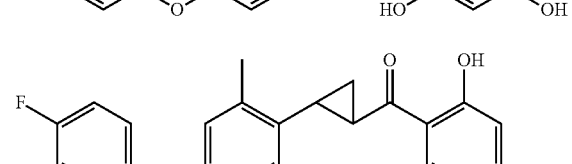 |

TABLE 1-continued

Representative Compounds.

| Example | Structure |
|---|---|
| 37 | 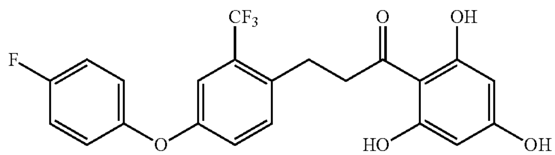 [SMILES: O=C(CCc1ccc(Oc2ccc(F)cc2)cc1C(F)(F)F)c1c(O)cc(O)cc1O] |
| 38 | 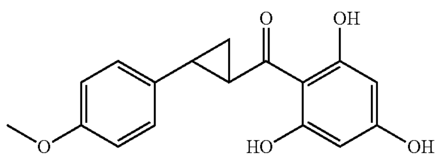 [SMILES: COc1ccc(C2CC2C(=O)c2c(O)cc(O)cc2O)cc1] |
| 39 | 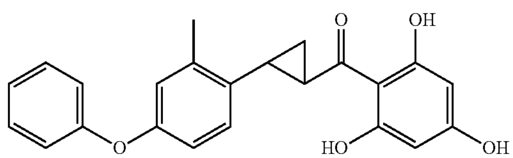 [SMILES: Cc1cc(Oc2ccccc2)ccc1C1CC1C(=O)c1c(O)cc(O)cc1O] |
| 40 | 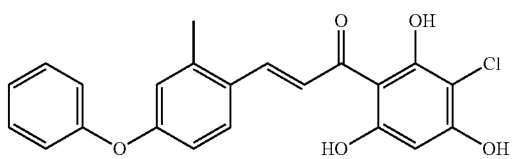 [SMILES: Cc1cc(Oc2ccccc2)ccc1/C=C/C(=O)c1c(O)cc(O)c(Cl)c1O] |
| 41 | 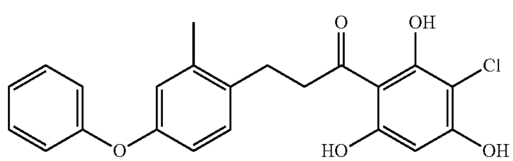 [SMILES: Cc1cc(Oc2ccccc2)ccc1CCC(=O)c1c(O)cc(O)c(Cl)c1O] |
| 42 | 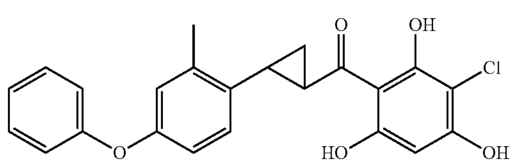 [SMILES: Cc1cc(Oc2ccccc2)ccc1C1CC1C(=O)c1c(O)cc(O)c(Cl)c1O] |
| 43 | 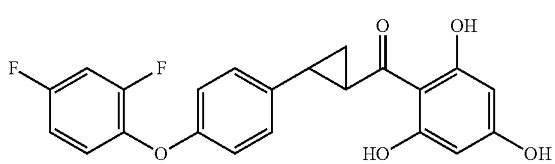 [SMILES: O=C(c1c(O)cc(O)cc1O)C1CC1c1ccc(Oc2ccc(F)cc2F)cc1] |
| 44 | 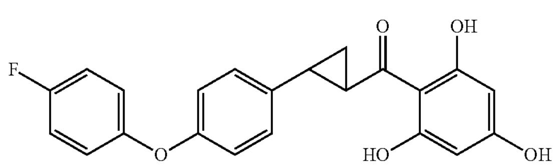 [SMILES: O=C(c1c(O)cc(O)cc1O)C1CC1c1ccc(Oc2ccc(F)cc2)cc1] |
| 45 | 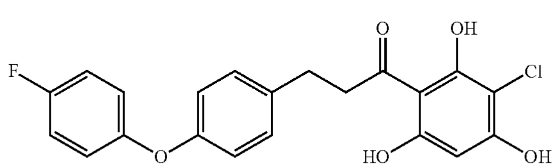 [SMILES: O=C(CCc1ccc(Oc2ccc(F)cc2)cc1)c1c(O)cc(O)c(Cl)c1O] |

TABLE 1-continued
Representative Compounds.
| Example | Structure |
|---|---|
| 46 | 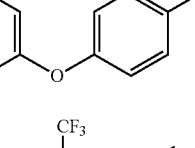 |
| 47 | 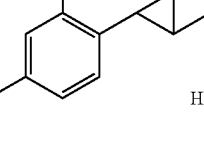 |
| 48 | 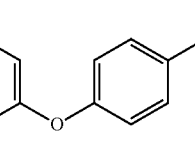 |
| 49 | 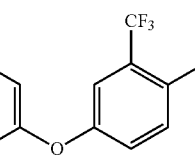 |
| 50 | 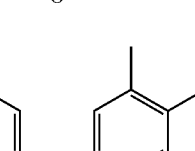 |
| 51 | 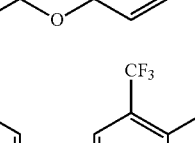 |
| 52 | 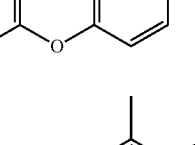 |
| 53 | 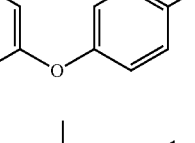 |
| 54 | 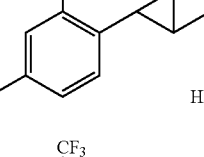 |

TABLE 1-continued

Representative Compounds.

| Example | Structure |
| --- | --- |
| 55 | 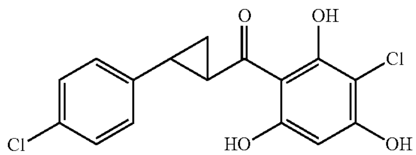 [SMILES: O=C(c1c(O)cc(O)c(Cl)c1O)C1CC1c1ccc(Cl)cc1] |
| 56 | 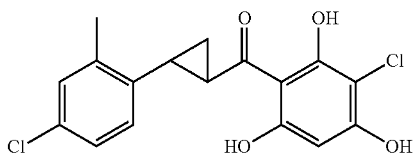 [SMILES: Cc1cc(Cl)ccc1C1CC1C(=O)c1c(O)cc(O)c(Cl)c1O] |
| 57 | 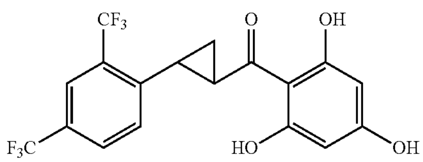 [SMILES: O=C(c1c(O)cc(O)cc1O)C1CC1c1ccc(C(F)(F)F)cc1C(F)(F)F] |
| 58 | 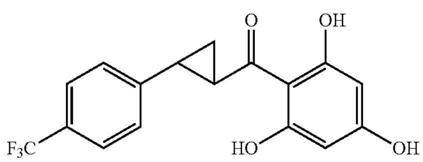 [SMILES: O=C(c1c(O)cc(O)cc1O)C1CC1c1ccc(C(F)(F)F)cc1] |
| 59 | 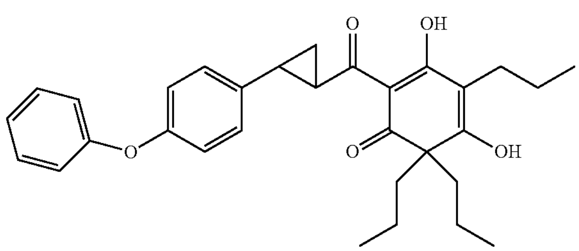 [SMILES: CCCC1=C(O)C(CCC)(CCC)C(=O)C(C(=O)C2CC2c2ccc(Oc3ccccc3)cc2)=C1O] |
| 60 | 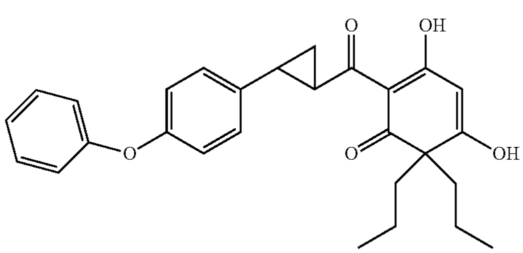 [SMILES: CCCC1(CCC)C(=O)C(C(=O)C2CC2c2ccc(Oc3ccccc3)cc2)=C(O)C=C1O] |
| 61 | 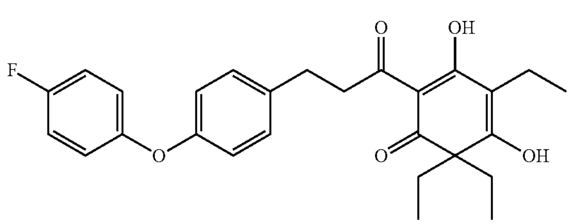 [SMILES: CCC1=C(O)C(CC)(CC)C(=O)C(C(=O)CCc2ccc(Oc3ccc(F)cc3)cc2)=C1O] |

TABLE 1-continued

Representative Compounds.

| Example | Structure |
| --- | --- |
| 62 | 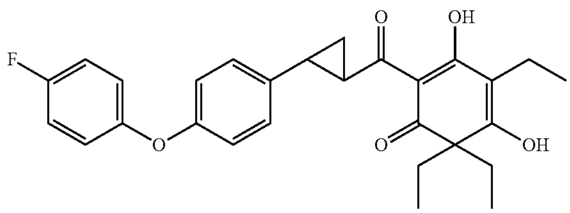 [SMILES: CCC1=C(O)C(CC)(CC)C(=O)C(C(=O)C2CC2c2ccc(Oc3ccc(F)cc3)cc2)=C1O] |
| 63 | 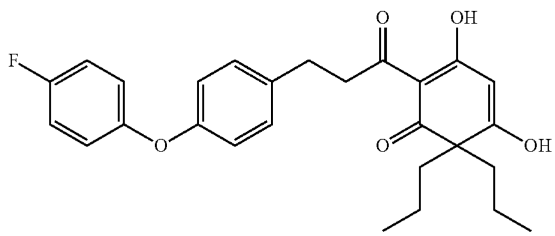 [SMILES: CCCC1(CCC)C(=O)C(C(=O)CCc2ccc(Oc3ccc(F)cc3)cc2)=C(O)C=C1O] |
| 64 | 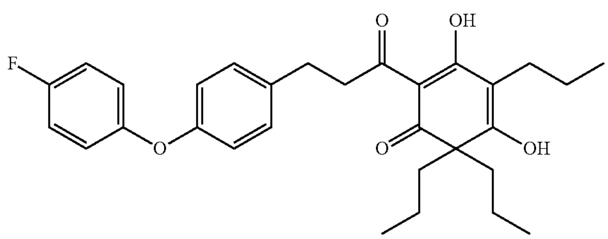 [SMILES: CCCC1=C(O)C(CCC)(CCC)C(=O)C(C(=O)CCc2ccc(Oc3ccc(F)cc3)cc2)=C1O] |
| 65 | 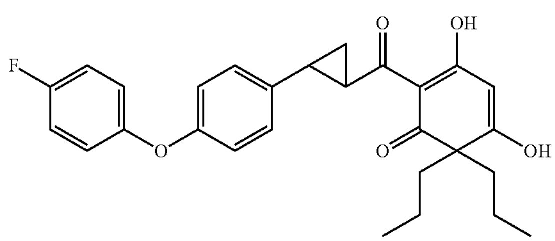 [SMILES: CCCC1(CCC)C(=O)C(C(=O)C2CC2c2ccc(Oc3ccc(F)cc3)cc2)=C(O)C=C1O] |
| 66 | 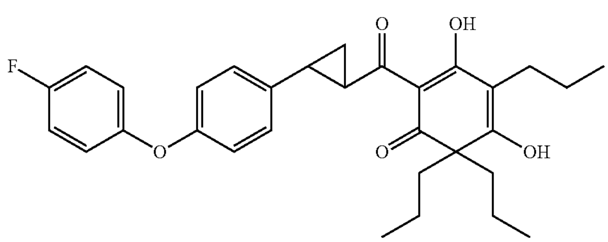 [SMILES: CCCC1=C(O)C(CCC)(CCC)C(=O)C(C(=O)C2CC2c2ccc(Oc3ccc(F)cc3)cc2)=C1O] |
| 67 | 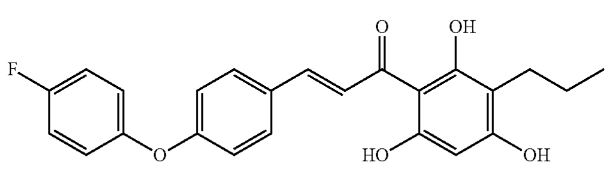 [SMILES: CCCc1c(O)cc(O)c(C(=O)/C=C/c2ccc(Oc3ccc(F)cc3)cc2)c1O] |

TABLE 1-continued
Representative Compounds.
| Example | Structure |
|---|---|
| 68 | 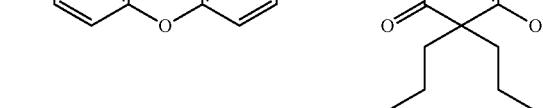 |
| 69 | 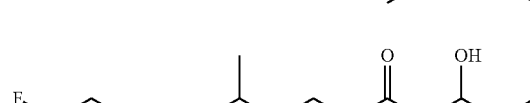 |
| 70 | 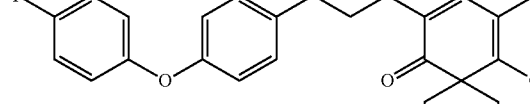 |
| 71 | 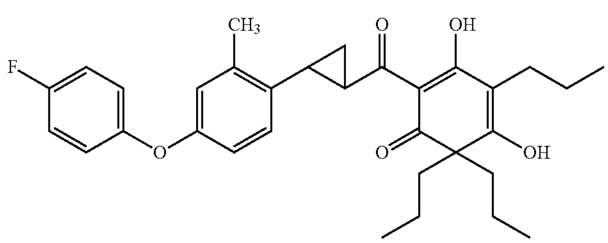 [SMILES: CCCC1=C(O)C(CCC)(CCC)C(=O)C(C(=O)C2CC2c2ccc(Oc3ccc(F)cc3)cc2C)=C1O] |
| 72 | 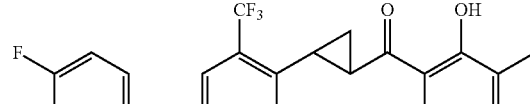 |
| 73 | 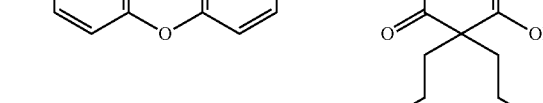 |

TABLE 1-continued

Representative Compounds.

| Example | Structure |
|---------|-----------|
| 74 | 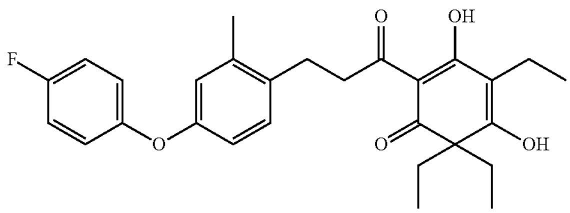 [SMILES: CCC1=C(O)C(CC)(CC)C(=O)C(C(=O)CCc2ccc(Oc3ccc(F)cc3)cc2C)=C1O] |
| 75 | 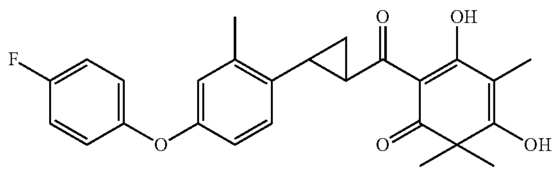 [SMILES: CC1=C(O)C(C)(C)C(=O)C(C(=O)C2CC2c2ccc(Oc3ccc(F)cc3)cc2C)=C1O] |
| 76 | 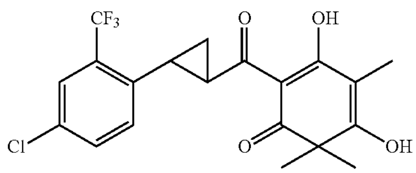 [SMILES: CC1=C(O)C(C)(C)C(=O)C(C(=O)C2CC2c2ccc(Cl)cc2C(F)(F)F)=C1O] |
| 77 | 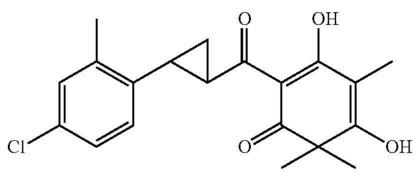 [SMILES: CC1=C(O)C(C)(C)C(=O)C(C(=O)C2CC2c2ccc(Cl)cc2C)=C1O] |
| 78 | 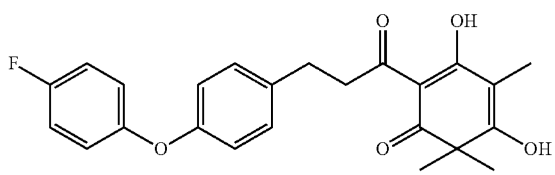 [SMILES: CC1=C(O)C(C)(C)C(=O)C(C(=O)CCc2ccc(Oc3ccc(F)cc3)cc2)=C1O] |
| 79 | 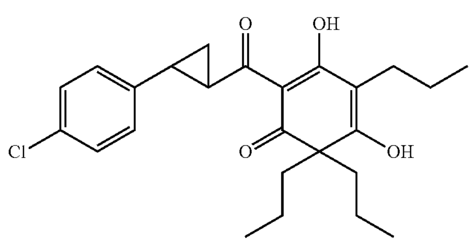 [SMILES: CCCC1=C(O)C(CCC)(CCC)C(=O)C(C(=O)C2CC2c2ccc(Cl)cc2)=C1O] |
| 80 | 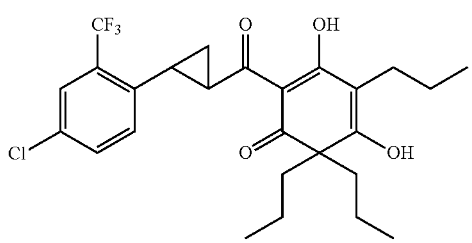 [SMILES: CCCC1=C(O)C(CCC)(CCC)C(=O)C(C(=O)C2CC2c2ccc(Cl)cc2C(F)(F)F)=C1O] |

TABLE 1-continued

Representative Compounds.

| Example | Structure |
| --- | --- |
| 81 | 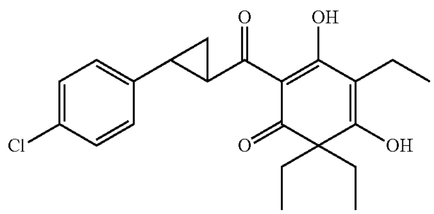 [SMILES: CCC1=C(O)C(CC)(CC)C(=O)C(C(=O)C2CC2c2ccc(Cl)cc2)=C1O] |
| 82 | 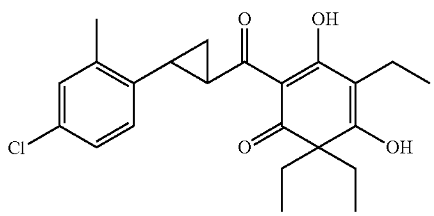 [SMILES: CCC1=C(O)C(CC)(CC)C(=O)C(C(=O)C2CC2c2ccc(Cl)cc2C)=C1O] |
| 83 | 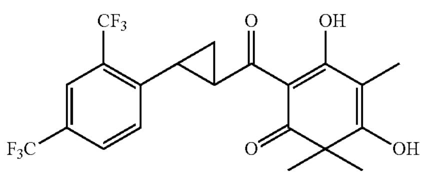 [SMILES: CC1=C(O)C(C)(C)C(=O)C(C(=O)C2CC2c2ccc(C(F)(F)F)cc2C(F)(F)F)=C1O] |
| 84 | 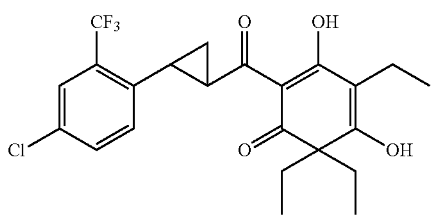 [SMILES: CCC1=C(O)C(CC)(CC)C(=O)C(C(=O)C2CC2c2ccc(Cl)cc2C(F)(F)F)=C1O] |
| 85 | 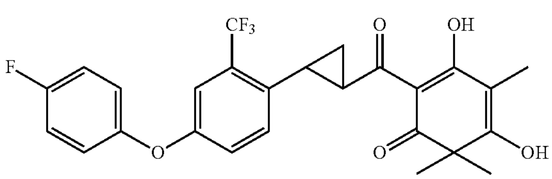 [SMILES: CC1=C(O)C(C)(C)C(=O)C(C(=O)C2CC2c2ccc(Oc3ccc(F)cc3)cc2C(F)(F)F)=C1O] |
| 86 | 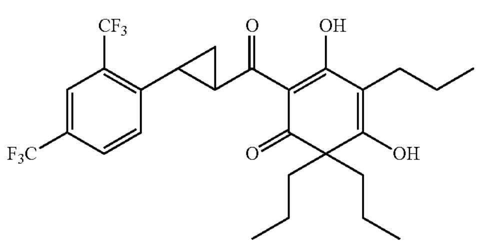 [SMILES: CCCC1=C(O)C(CCC)(CCC)C(=O)C(C(=O)C2CC2c2ccc(C(F)(F)F)cc2C(F)(F)F)=C1O] |
| 87 | 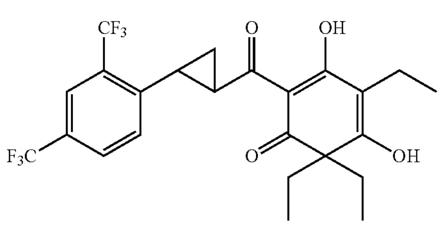 [SMILES: CCC1=C(O)C(CC)(CC)C(=O)C(C(=O)C2CC2c2ccc(C(F)(F)F)cc2C(F)(F)F)=C1O] |

TABLE 1-continued

Representative Compounds.

| Example | Structure |
|---|---|
| 88 | 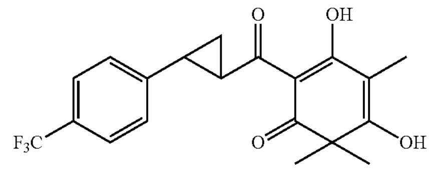 [SMILES: CC1=C(O)C(C)(C)C(=O)C(C(=O)C2CC2c2ccc(C(F)(F)F)cc2)=C1O] |
| 89 | 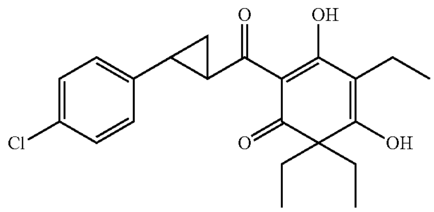 [SMILES: CCC1=C(O)C(CC)(CC)C(=O)C(C(=O)C2CC2c2ccc(Cl)cc2)=C1O] |
| 90 | 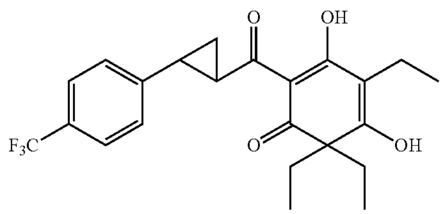 [SMILES: CCC1=C(O)C(CC)(CC)C(=O)C(C(=O)C2CC2c2ccc(C(F)(F)F)cc2)=C1O] |
| 91 | 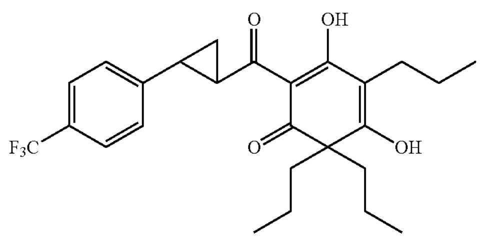 [SMILES: CCCC1=C(O)C(CCC)(CCC)C(=O)C(C(=O)C2CC2c2ccc(C(F)(F)F)cc2)=C1O] |
| 92 | 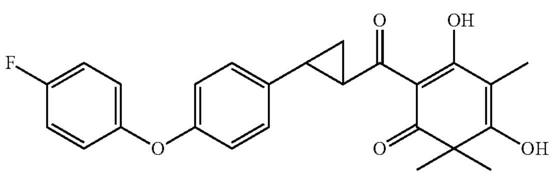 [SMILES: CC1=C(O)C(C)(C)C(=O)C(C(=O)C2CC2c2ccc(Oc3ccc(F)cc3)cc2)=C1O] |

Example 1

Synthesis of 3-(5-methylthiophen-2-yl)-1-(2,4,6-trihydroxyphenyl)propan-1-one To a solution of 1-(2,4,6-trihydroxyphenyl)ethanone (50.00 g, 297.35 mmol, Sigma-Aldrich) in DMF (1.00 L) was added NaH (41.60 g, 1.04 mol, 60% dispersion in mineral oil, Sigma-Aldrich) portionwise at 0~10° C. The mixture was stirred at 25° C. for 30 min, chloro(methoxy)methane (83.79 g, 1.04 mol, 79.05 mL, Sigma-Aldrich) was added dropwise and stirred for another 16 hours. The mixture was poured into water (3 L) and extracted with ethyl acetate (2×1 L), the combined organic layers were washed with brine (1 L) and dried over anhydrous $Na_2SO_4$, filtered and evaporated under vacuum to give a black oil. 1-(2,4,6-tris(methoxymethoxy)phenyl) ethanone (55.0 g, 61% yield) was isolated by silica gel chromatography (eluent, 30% ethyl acetate in hexane). Yield: 35%. MS (ESI): calculated, m/z 279.3 (MH$^+$); found, 300.0. $^1$H NMR (400 MHz, CDCl$_3$) δ=6.51 (s, 2H), 5.19-5.11 (m, 6H), 3.51-3.42 (m, 9H), 2.54-2.42 (m, 3H).

To a solution of 1-(2,4,6-tris(methoxymethoxy)phenyl) ethan-1-one (718.6 mg, 2.392 mmol) and 5-methylthiophene-2-carbaldehyde (315.9 mg, 0.27 ml, 2.5 mmol, Aldrich) in MeOH (6.00 mL) was added KOH (210 mg, 3.74 mmol) at room temperature. The reaction mixture was stirred at room temperature overnight. The reaction mixture was concentrated, and then water (20 ml) was added, 1 M HCl was added to neutralize the pH. The mixture was extracted with ethyl acetate (6×20 ml) and the organic layer was washed with brine (30 ml). The combined extracts were dried over anhydrous sodium sulfate, filtered and evaporated under vacuum to crude product. (E)-3-(5-methylthiophen-2-yl)-1(2,4,6-tris(methoxymethoxy)phenyl)prop-2-en-1-one was isolated by silica gel chromatography (eluent, 40% ethyl acetate in hexane) in 77% yield (752.3 mg).

(E)-3-(5-methylthiophen-2-yl)-1(2,4,6-tris (methoxymethoxy)phenyl)prop-2-en-1-one (0.345 g, 0.845 mmol) was dissolved in 8 mL methanol after flushing with N$_2$. Raney Nickel (162.5 uL, 50% slurry in water, ACROS) was added and then hydrogen gas was bubbled in the reaction mixture via a needle. The reaction was stirred at room temperature; after three hours, the reaction was monitored to be mostly complete by TLC. The reaction mixture was filtered with Celite and rinsed with methanol. The organics was concentrated under vacuum and 3-(5-methylthiophen-2-yl)-1(2,4,6-tris(methoxymethoxy)phenyl)propan-1-one was isolated by silica gel chromatography in 67% yield (0.232 g) as a clean colorless oil.

3-(5-methylthiophen-2-yl)-1(2,4,6-tris(methoxymethoxy)phenyl)propan-1-one (130 mg, 0.317 mmol) was dissolved in 4 mL methanol and concentrated HCl (0.2 mL, 37%, Aldrich) was added dropwise. The reaction was stirred at 60° C. for 4 hours. After cooling, the reaction mixture was neutralized with 1M NaOH and then extracted with ethyl acetate (3×10 ml). The combined extracts were dried over anhydrous sodium sulfate, filtered and evaporated under vacuum to crude product. The crude product was purified by prep HPLC (reverse phase). 43.5 mg of 3-(5-methylthiophen-2-yl)-1-(2,4,6-trihydroxyphenyl)propan-1-one was obtained as a light reddish oil. Yield: 39%. MS: m/z 305.1, [M+H]$^+$; $^1$H NMR (500 MHz, d$_6$-acetone); δ 11.7 (s, 1), 9.25 (s, 1), 6.63 (d, J=3.3 Hz, 1), 6.55 (d, J=2.3 Hz, 1), 5.94 (s, 2), 3.42 (t, J=7.4 Hz, 2), 3.11 (t, J=7.4 Hz, 2), 2.38 (s, 3).

Example 2

Synthesis of (2-(4-chlorophenyl)cyclopropyl)(2,4,6-trihydroxyphenyl)methanone

To a solution of 1-(2,4,6-tris(methoxymethoxy)phenyl)ethan-1-one (509 mg, 1.69 mmol) and 4-chlorobenzaldehyde (0.148 g, 1.05 mmol, Aldrich) in MeOH (4.00 mL) was added KOH (148 mg, 2.64 mmol) at room temperature. The reaction mixture was concentrated, and then water (20 ml) was added, sat. NH$_4$Cl (20 mL) was added to neutralize the pH. The mixture was extracted with ethyl acetate (4×15 ml) and the organic layer was washed with brine (30 ml). The combined extracts were dried over anhydrous sodium sulfate and concentrated under reduced pressure. Purification on silica gel (Hex/EtOAc) provided the (2-(4-chlorophenyl)cyclopropyl)(2,4,6-tri(methoxymethoxy)phenyl)methanone as a yellow solid in 80% yield (0.367 g).

In a 50 mL round bottom flask, trimethylsulfoxonium iodide (0.227 g, 1.0 mmol, Aldrich) and sodium hydride (41.0 g, 1.0 mmol, 60% dispersion in mineral oil, Aldrich) were added sequentially to 4.5 mL dry DMSO. The reaction mixture was stirred for 1 hour followed by the addition of the (2-(4-chlorophenyl)cyclopropyl)(2,4,6-tri(methoxymethoxy)phenyl)methanone (0.122 g, 0.24 mmol) in 1.0 mL DMSO dropwise over 1 minute. The resulting mixture was stirred for 8 hours and then the reaction was quenched by pouring into 50 mL sat. NH$_4$Cl. The mixture was extracted with ethyl acetate (4×15 mL). The combined extracted were diluted to 100 mL and extracted with sat. NaCl. The organic layer was dried and concentrated. The crude residue was dissolved in 10 mL methanol and concentrated HCl (2 mL, 37%, Aldrich) was added dropwise. The reaction was stirred overnight. The crude reaction was concentrated on a rotary evaporator and dissolved in 8 mL of 50% acetonitrile/water and purified by prep HPLC. (2-(4-chlorophenyl)cyclopropyl)(2,4,6-trihydroxyphenyl)methanone was obtained as an off-white solid (18.3 mg, 25% yield). MS: m/z 305.1 [M+H]$^+$; $^1$H NMR (500 MHz, d$_6$-DMSO) δ 12.2 (s, 2), 10.4 (s, 1), 7.30 (dd, J=46.5, 8.1 Hz, 4), 5.80 (s, 2), 3.83-3.52 (m, 1), 3.33 (s, 2), 3.12 (s, 1), 2.77-2.26 (m, 4), 2.12 (t, J=6.5 Hz, 1), 1.91-1.72 (m, 1), 1.71-1.57 (m, 1), 1.49 (dd, J=10.3, 7.1 Hz, 1).

Example 3

Synthesis of 3-(4-(3-chlorophenoxy)phenyl)-1-(2,4,6-trihydroxyphenyl)propan-1-one 3-(4-(3-chlorophenoxy)phenyl)-1-(2,4,6-trihydroxyphenyl)propan-1-one was synthesized as described in Example 1, but 5-methylthiophene-2-carbaldehyde was replaced by 4-(3-chlorophenoxy)benzaldehyde. Yield: 50%. MS: m/z 385.2 [M+H]$^+$, 387.2 [M+2+H]$^+$; $^1$H NMR (500 MHz, d$_6$-acetone) δ 11.9 (br s, 0.4), 11.8 (br s, 1), 9.31 (br s, 1), 7.42 (d, J=8.1 Hz, 1), 7.38 (d, J=8.1 Hz, 2), 7.16 (d, J=7.7 Hz, 1), 7.08-7.0 (comp, 3), 6.96 (d, J=8.1 Hz, 1), 5.97 (s, 2), 3.37 (t, J=7.4 Hz, 2), 3.04 (t, J=7.5 Hz, 2).

Example 4

Synthesis of 3-(4-(4-chlorophenoxy)phenyl)-1-(2,4,6-trihydroxyphenyl)propan-1-one 3-(4-(4-chlorophenoxy)phenyl)-1-(2,4,6-trihydroxyphenyl)propan-1-one was synthesized as described in Example 1, but 5-methylthiophene-2-carbaldehyde was replaced by 4-(4-chlorophenoxy)benzaldehyde. The title compound was isolated as a white solid. Yield: 19%. MS: m/z 385.2 [M+H]$^+$, 387.2 [M+2+H]$^+$; $^1$H NMR (500 MHz, d$_6$-acetone) δ 11.7 (br s, 2), 9.24 (br s, 1), 7.41 (d, J=8.5 Hz, 2), 7.36 (d, J=8.5 Hz, 2), 7.02 (d, J=8.6 Hz, 2), 7.0 (d, J=8.6 Hz, 2), 5.99 (s, 2), 3.45 (t, J=7.7 Hz, 2), 3.03 (t, J=7.6 Hz, 2).

Example 5

Synthesis of (E)-3-(4-(4-chlorophenoxy)phenyl)-1-(2,4,6-trihydroxyphenyl)prop-2-en-1-one 3-(4-(4-chlorophenoxy)phenyl)-1-(2,4,6-trihydroxyphenyl)propan-1-one was synthesized as described in Example 1, but 5-methylthiophene-2-carbaldehyde was replaced by 4-(4-chlorophenoxy)benzaldehyde. Yield: 50%. MS: m/z 383.2 [M+H]$^+$, 385.2 [M+2+H]$^+$; $^1$H NMR (500 MHz, d$_6$-acetone); the compound exists as a mixture of E and Z isomers in the ratio 1:0.4; δ 12.2 (br s, 0.3), 11.0 (br s, 2), 8.24 (d, J=15.6 Hz, 1), 7.82 (d, J=15.6, 1), 7.77 (d, J=8.5 Hz, 2), 7.65 (d, J=8.4, Hz, 1), 7.48 (d, J=8.6, Hz, 2), 7.45 (br s, 0.4), 7.15 (d, J=8.7, Hz, 2.5), 7.11 (d, J=8.7, Hz, 2.6), 6.07-6.03 (m, 0.4), 6.02 (br s, 2), 5.62 (dd, J=12.8, J=2.5. Hz, 0.4), 3.33-3.16 (m, 1), 2.85 (dd, J=17.0, J=2.6 Hz, 1).

Example 6

Synthesis of (E)-3-(4-(pyridin-2-yloxy)phenyl)-1-(2,4,6-trihydroxyphenyl)prop-2-en-1-one (E)-3-(4-(pyridin-2-yloxy)phenyl)-1-(2,4,6-trihydroxyphenyl)prop-2-en-1-one was synthesized as described in Example 1, but 5-methylthiophene-2-carbaldehyde was replaced by 4-(pyridin-2-yloxy)benzaldehyde. The title compound was isolated as a yellow solid. Yield: 40%. MS: m/z 350.4 [M+H]$^+$; $^1$H NMR (500 MHz, d$_6$-acetone); the compound exists as a mixture of E and Z isomers in the ratio 1:0.2; δ 12.2 (br s, 0.2), 8.26 (d, J=15.7 Hz, 1), 8.20 (d, J=4.0, 1), 8.18 (br s, 0.2), 7.94-7.88 (m, 1), 7.84 (d, J=15.6 Hz, 1), 7.78 (d, J=8.5, Hz, 2), 7.65 (d, J=8.3, Hz, 0.4), 7.24

(d, J=8.3, Hz, 2.3), 7.18 (app t, J=6.1, Hz, 1), 7.16-7.13 (m, 0.2), 7.09 (d, J=8.2, Hz, 1), 7.06 (br s, 0.2), 6.05 (br s, 0.2), 6.02 (br s, 2), 5.64 (dd, J=12.7, J=2.6. Hz, 0.2), 3.32-3.21 (m, 0.4), 2.26-2.13 (m, 0.4), 2.05-1.93 (m, 0.3).

Example 7

Synthesis of (E)-3-(4-benzyloxy)phenyl)-1-(2,4,6-trihydroxyphenyl)prop-2-en-1-one (E)-3-(4-benzyloxy)phenyl)-1-(2,4,6-trihydroxyphenyl) prop-2-en-1-one was synthesized as described in Example 1, but 5-methylthiophene-2-carbaldehyde was replaced by 4-(benzyloxy)benzaldehyde. The title compound was isolated as a yellow solid. Yield: 40%. MS: m/z 363.4 [M+H]$^+$; $^1$H NMR (500 MHz, CDCl3): δ 5.13 (s, 2H), 5.85 (s, 2H), 7.04 (m, 2H), 7.32-7.43 (m, 4H), 7.57 (m, 2H), 7.71 (d, J=15 Hz, 1H), 8.10 (d, J=15 Hz, 1H).

Example 8

Synthesis of (E)-3-(4-phenoxyphenyl)-1-(2,4,6-trihydroxyphenyl)prop-2-en-1-one (E)-3-(4-phenoxyphenyl)-1-(2,4,6-trihydroxyphenyl) prop-2-en-1-one was synthesized as described in Example 1, but 5-methylthiophene-2-carbaldehyde was replaced by 4-phenoxybenzaldehyde. The title compound was isolated as a yellow solid. Yield: 60%. MS: m/z 349.4 [M+H]$^+$; $^1$H NMR (500 MHz, d$_6$-acetone); the compound exists as a mixture of E and Z isomers; δ 12.2 (br s, 1), 7.63 (d, J=8.6 Hz, 2), 7.49-7.42 (m, 2), 7.21 (app t, J=7.4 Hz, 1), 7.14-7.06 (comp, 4), 6.0 (dd, J=14.3, 2.2 Hz, 2, 5.61 (dd, J=12.9, 3.0 Hz, 1), 3.29-3.20 (m, 1), 2.84 (dd, J=17.2, 3.1 Hz, 2), 2.13 (s, 2).

Example 9

Synthesis of (E)-3-(2,4-bis(trifluoromethyl)phenyl)-1-(2,4,6-trihydroxyphenyl)prop-2-en-1-one To a solution of 1-[2,4,6-tris(methoxymethoxy)phenyl] ethanone (500.00 mg, 1.67 mmol) and 2,4-bis(trifluoromethyl)benzaldehyde (484.24 mg, 2.00 mmol, Sigma-Aldrich) in MeOH (5.00 mL) was added KOH (140.56 mg, 2.51 mmol) at 0° C. The reaction mixture was brought to room temperature and stirred for 16 hours. The mixture was poured into water (20 mL) and extracted with ethyl acetate (2×30 mL), the combined organic layers were washed with brine (20 mL) and dried over anhydrous Na$_2$SO$_4$, filtered and evaporated under vacuum to give a yellow oil. The residue was dissolved in MeOH (5.00 mL) and THF (2.00 mL), con. HCl (0.2 mL) was added dropwise at 20° C. and stirred at 20° C. for 12 hours. The mixture was neutralized with saturated NaHCO$_3$ solution (3 mL) to pH>6. The mixture was poured into water (20 mL) and extracted with ethyl acetate (2×30 mL), the combined organic layers were washed with brine (20 mL) and dried over anhydrous Na$_2$SO$_4$, filtered and evaporated under vacuum. The residue was purified by prep-HPLC (Phenomenex Synergi C18 150*25*10 um, 60-90% B in 11 mins; buffer A=0.1% TFA-H$_2$O, buffer B=0.1% TFA-Acetonitrile) to afford 326 mg of the title compound as yellowish solid. Yield: 27%. MS (ESI): calculated, m/z 393.1 (MH$^+$); found, 393.0. $^1$H NMR (400 MHz, d4-Methanol) δ=8.27 (d, J=15.4 Hz, 1H), 8.12 (d, J=8.2 Hz, 1H), 8.06-7.96 (m, 3H), 5.89 (s, 2H).

Example 10

Synthesis of 3-(4-(4-fluorophenoxy)phenyl)-1-(2,4,6-trihydroxyphenyl)propan-1-one 3-(4-(4-fluorophenoxy)phenyl)-1-(2,4,6-trihydroxyphenyl)propan-1-one was synthesized as described in Example 1, but 5-methylthiophene-2-carbaldehyde was replaced by 4-(4-fluorophenoxy)benzaldehyde. The title compound was isolated as a colorless oil. Yield: 34%. MS: m/z 369.4 [M+H]$^+$; $^1$H NMR (500 MHz, d$_3$-acetonitrile); the compound exists as a mixture of isomers and tautomers; δ 7.25 (d, J=8.5 Hz, 2), 7.15-7.08 (m, 2), 7.04-6.99 (m, 2), 6.91 (d, J=8.6 Hz, 2), 6.15 (d, J=3.0 Hz, 0.6), 5.95 (d, J=3.0 Hz, 0.6), 5.92 (br s, 0.1), 5.89 (s, 2), 4.41 (s, 1), 3.34 (t, J=7.7 Hz, 2), 3.38 (app t, J=7.1 Hz, 0.4), 3.29-3.24 (m, 0.5), 2.27 (br s, 2, signal merged with water peak), 2.94 (t, J=7.7 Hz, 2), 1.07 (app t, J=7.2 Hz, 0.5).

Example 11

Synthesis of (E)-3-(4-(4-fluorophenoxy)phenyl)-1-(2,4,6-trihydroxyphenyl)prop-2-en-1-one (E)-3-(2,4-bis(trifluoromethyl)phenyl)-1-(2,4,6-trihydroxyphenyl)prop-2-en-1-one was synthesized as described in Example 9, but 2,4-bis(trifluoromethyl)benzaldehyde was replaced by 4-(4-fluorophenoxy)benzaldehyde. Yield: 49%. MS (ESI): calculated, m/z 367.1 (MH$^+$); found, 367.1. $^1$H NMR (400 MHz, d6-Acetone) δ=12.21-11.96 (m, 1H), 9.39 (br s, 1H), 8.27-8.12 (m, 1H), 7.84-7.66 (m, 3H), 7.28-7.13 (m, 4H), 7.04 (d, J=8.7 Hz, 2H), 6.00 (s, 2H).

Example 12

Synthesis of (2-(4-(4-fluorophenoxy)phenyl)cyclopropyl)(2,4,6-trihydroxyphenyl) methanone (2-(4-(4-fluorophenoxy)phenyl)cyclopropyl)(2,4,6-trihydroxyphenyl) methanone was synthesized as described in Example 2, but 4-chlorobenzaldehyde was replaced by 4-(4-fluorophenoxy)benzaldehyde. Yield: 16%. MS: m/z 381.0 [M+H]$^+$; $^1$H NMR (500 MHz, d$_6$-acetone); the compound exists as a mixture of isomers and tautomers; δ 7.28 (d, J=8.6 Hz, 2), 7.22-7.15 (m, 2), 7.09-7.04 (m, 2), 6.95 (d, J=8.4 Hz, 2), 5.99 (s, 2), 3.85-3.78 (m, 1), 3.42 (t, J=7.0 Hz, 2), 3.28 (q, J=7.1 Hz, 2), 2.69-2.62 (m, 1), 2.23 (t, J=7.9 Hz, 2), 2.05-1.95 (comp, 2), 1.90-1.84 (m, 1), 1.51-1.43 (m, 1), 1.08 (t, J=7.4 Hz, 3).

Example 13

Synthesis of (2-(4-(4-chlorophenoxy)phenyl)cyclopropyl)(2,4,6-trihydroxyphenyl)methanone (2-(4-(4-chlorophenoxy)phenyl)cyclopropyl)(2,4,6-trihydroxyphenyl)methanone was synthesized as described in Example 2, but 4-chlorobenzaldehyde was replaced by 4-(4-chlorophenoxy)benzaldehyde. Yield: 20%. MS: m/z 397.0 [M+H]$^+$; $^1$H NMR (500 MHz, d$_3$-acetonitrile); the compound exists as a mixture of isomers and tautomers; δ 7.38 (d, J=8.9 Hz, 2, 7.32 (d, J=8.6 Hz, 2), 7.07-6.97 (m, 4), 5.87 (s, 2), 4.41 (br s, 0.2), 4.26-4.21 (m, 1), 3.37 (t, J=7.1 Hz, 0.4), 3.26 (q, J=6.8 Hz, 0.5), 3.10-3.03 (comp, 2), 2.13-2.05 (comp, 4, signal merged with water peak), 2.01-1.97 (comp, 2, signal merged with the solvent peak) 1.08 (t, J=7.5 Hz, 0.5).

Example 14

Synthesis of (E)-3-(4-(trifluoromethyl)phenyl)-1-(2,4,6-trihydroxyphenyl)prop-2-en-1-one (E)-3-(4-(trifluoromethyl)phenyl)-1-(2,4,6-trihydroxyphenyl)prop-2-en-1-one was synthesized as described in Example 9, but 2,4-bis(trifluoromethyl)benzaldehyde was replaced by 4-(trifluoromethyl)benzaldehyde. Yield: 91%. MS (ESI): calculated, m/z 325.1 (MH$^+$); found, 325.0. $^1$H NMR (400 MHz, d6-Acetone) $^1$H NMR (400 MHz, Acetone) δ=8.35 (d, J=15.7 Hz, 1H), 7.92 (d, J=8.3 Hz, 2H), 7.84-7.77 (m, 3H), 6.01 (s, 2H).

Example 15

Synthesis of (E)-3-(4-phenoxy-2-(trifluoromethyl)phenyl)-1-(2,4,6-trihydroxyphenyl)prop-2-en-1-one (E)-3-(4-phenoxy-2-(trifluoromethyl)phenyl)-1-(2,4,6-trihydroxyphenyl)prop-2-en-1-one was synthesized as described in Example 9, but 2,4-bis(trifluoromethyl)benzaldehyde was replaced by 4-phenoxy-2-(trifluoromethyl)benzaldehyde. Yield: 47%. MS (ESI): calculated, m/z 417.4 (MH$^+$); found, 417.1. $^1$H NMR (400 MHz, d6-Acetone) δ=12.44-11.66 (m, 1H), 9.98-9.01 (m, 1H), 8.28-8.18 (m, 1H), 8.07 (dd, J=2.3, 15.4 Hz, 1H), 8.02 (d, J=8.8 Hz, 1H), 7.57-7.45 (m, 2H), 7.37 (d, J=2.6 Hz, 1H), 7.32-7.25 (m, 2H), 7.23-7.16 (m, 2H), 6.01 (s, 2H).

Example 16

Synthesis of 3-(4-phenoxy-2-(trifluoromethyl)phenyl)-1-(2,4,6-trihydroxyphenyl)propan-1-one To a solution of (E)-3-(4-phenoxy-2-(trifluoromethyl)phenyl)-1-(2,4,6-trihydroxyphenyl)prop-2-en-1-one (Example 15, 227.3 mg, 545.94 umol) in MeOH (10.00 mL) was added Pd/C (50.00 mg) and stirred at 20° C. under H$_2$ (15 psi) for 15 mins. The reaction mixture was filtered and evaporated under vacuum. The residue was purified by prep-HPLC (Phenomenex Synergi C18 150*25*10 um, 60-90% B in 11 mins; buffer A=0.1% TFA-H$_2$O, buffer B=0.1% TFA-Acetonitrile) to obtain 204.6 mg of 3-(4-phenoxy-2-(trifluoromethyl)phenyl)-1-(2,4,6-trihydroxyphenyl)propan-1-one as yellowish solid. Yield: 50%. MS (ESI): calculated, m/z 419.1 (MH$^+$); found, 419.1. $^1$H NMR (400 MHz, d6-Acetone) δ=12.43-11.38 (m, 1H), 9.89-9.33 (m, 1H), 7.60 (d, J=8.4 Hz, 1H), 7.48-7.41 (m, 2H), 7.28 (d, J2.5 Hz, 1H), 7.24-7.18 (m, 2H), 7.12-7.07 (m, 2H), 5.98 (s, 2H), 3.49-3.42 (m, 2H), 3.22-3.13 (m, 2H).

Example 17

Synthesis of (E)-3-(4-(4-chlorophenoxy)-2-(trifluoromethyl)phenyl)-1-(2,4,6-trihydroxyphenyl)prop-2-en-1-one (E)-3-(4-(4-chlorophenoxy)-2-(trifluoromethyl)phenyl)-1-(2,4,6-tri hydroxyphenyl)prop-2-en-1-one was synthesized as described in Example 9, but 2,4-bis(trifluoromethyl)benzaldehyde was replaced by 4-(4-chlorophenoxy)-2-(trifluoromethyl)benzaldehyde. Yield: 52%. MS (ESI): calculated, m/z 451.1 (MH$^+$); found, 451.0. $^1$H NMR (400 MHz, d6-Acetone) δ=12.35-11.25 (m, 1H), 9.43 (br s, 1H), 8.28-8.17 (m, 1H), 8.12-7.99 (m, 2H), 7.55-7.46 (m, 2H), 7.42 (d, J=2.5 Hz, 1H), 7.33 (dd, J=2.5, 8.7 Hz, 1H), 7.25-7.13 (m, 2H), 6.00 (s, 2H).

Example 18

Synthesis of (E)-3-(4-(4-chlorophenoxy)-2-methylphenyl)-1-(2,4,6-trihydroxyphenyl)prop-2-en-1-one (E)-3-(4-(4-chlorophenoxy)-2-methylphenyl)-1-(2,4,6-trihydroxyphenyl)prop-2-en-1-one was synthesized as described in Example 9, but 2,4-bis(trifluoromethyl)benzaldehyde was replaced by 4-(4-chlorophenoxy)-2-methylbenzaldehyde. Yield: 55%. MS (ESI): calculated, m/z 397.2 (MH$^+$); found, 397.1. $^1$H NMR (400 MHz, d6-Acetone) δ=8.20-8.11 (m, 1H), 8.10-8.01 (m, 1H), 7.75 (d, J=8.5 Hz, 1H), 7.49-7.39 (m, 2H), 7.15-7.05 (m, 2H), 6.96 (d, J=2.5 Hz, 1H), 6.90 (dd, J=2.6, 8.6 Hz, 1H), 6.00 (s, 2H), 2.49 (s, 3H).

Example 19

Synthesis of (2-(p-tolyl)cyclopropyl)(2,4,6-trihydroxyphenyl)methanone

To a solution of 1-(2,4,6-trihydroxyphenyl)ethanone (50.00 g, 297.35 mmol, Sigma-Aldrich) in DMF (1.00 L) was added NaH (41.60 g, 1.04 mol, 60% dispersion in mineral oil, Sigma-Aldrich) portionwise at 0-10° C. The mixture was stirred at 25° C. for 30 min, chloro(methoxy)methane (83.79 g, 1.04 mol, 79.05 mL, Sigma-Aldrich) was added dropwise and stirred for another 16 hours. The mixture was poured into water (3 L) and extracted with ethyl acetate (2×1 L), the combined organic layers were washed with brine (1 L) and dried over anhydrous Na$_2$SO$_4$, filtered and evaporated under vacuum to give a black oil. 1-(2,4,6-tris(methoxymethoxy)phenyl) ethanone (55.0 g, 61% yield) was isolated by silica gel chromatography (eluent, 30% ethyl acetate in hexane). Yield: 35%. MS (ESI): calculated, m/z 301.1 (MH$^+$); found, 300.0. $^1$H NMR (400 MHz, CDCl$_3$) δ=6.51 (s, 2H), 5.19-5.11 (m, 6H), 3.51-3.42 (m, 9H), 2.54-2.42 (m, 3H).

To a solution of 1-[2,4,6-tris(methoxymethoxy)phenyl]ethanone (2.00 g, 6.66 mmol) and 4-methylbenzaldehyde (0.8 g, 6.66 mmol, Sigma-Aldrich) in MeOH (20.00 mL) was added KOH (560.54 mg, 9.99 mmol) at 0° C. The reaction mixture was brought to room temperature and stirred for 16 hours. The mixture was poured into water (20 mL) and extracted with ethyl acetate (2×30 mL), the combined organic layers were washed with brine (20 mL) and dried over anhydrous Na$_2$SO$_4$, filtered and evaporated under vacuum to give a yellow oil. (E)-3-(p-tolyl)-1-(2,4,6-tris(methoxymethoxy)phenyl)prop-2-en-1-one (2.09 g, 78% yield) was isolated by silica gel chromatography (eluent, 50% ethyl acetate in hexane).

To a solution of trimethylsulfoxonium iodate (4.58 g, 20.81 mmol, Sigma-Aldrich) in DMSO (15.00 mL) was added NaH (832.45 mg, 20.81 mmol, 60% dispersion in mineral oil, Sigma-Aldrich) at 5° C. After stirred at 20° C. for 1 hour, a solution of (E)-3-(p-tolyl)-1-(2,4,6-tris(methoxymethoxy)phenyl)prop-2-en-1-one (1.67 g, 4.16 mmol) in DMSO (15.00 mL) was added. The reaction mixture was stirred for another 15 hours. The mixture was poured into water (20 mL), extracted with ethyl acetate (30 mL), dried over Na$_2$SO$_4$ and concentrated to get a yellow oil. The residue was dissolved in MeOH (10.00 mL) and THF (4.00 mL), con. HCl (0.4 mL) was added dropwise at 20° C. and stirred at 20° C. for 12 hours. The mixture was neutralized with saturated NaHCO₃ solution (6 mL) to pH>6. The mixture was poured into water (20 mL) and extracted with ethyl acetate (2×30 mL), the combined organic layers were washed with brine (20 mL) and dried over anhydrous $Na_2SO_4$, filtered and evaporated under vacuum. The residue was purified by prep-HPLC (Phenomenex Synergi C18 150*25*10 um, 60-90% B in 11 mins; buffer A=0.1% TFA-H₂O, buffer B=0.1% TFA-Acetonitrile) to afford 305 mg of the title compound as yellowish solid. Yield: 43%. MS (ESI): calculated, m/z 285.1 (MH⁺); found, 285.1. ¹H NMR (400 MHz, d6-Acetone) δ=12.26-11.44 (m, 1H), 10.19-8.92 (m, 1H), 7.35-6.88 (m, 4H), 6.19-5.87 (m, 2H), 3.84-3.73 (m, 1H), 2.59 (ddd, J=4.1, 6.4, 9.0 Hz, 1H), 2.29 (s, 3H), 1.82 (ddd, J=3.6, 5.4, 9.0 Hz, 1H), 1.43 (ddd, J=3.6, 6.5, 8.0 Hz, 1H).

Example 20

Synthesis of (2-(2,4-dimethylphenyl)cyclopropyl)(2,4,6-trihydroxyphenyl)methanone (2-(2,4-dimethylphenyl)cyclopropyl)(2,4,6-trihydroxyphenyl)methanone was synthesized as described in Example 19, but 4-methylbenzaldehyde was replaced by 2,4-dimethylbenzaldehyde. Yield: 44%. MS (ESI): calculated, m/z 299.1 (MH⁺); found, 299.1. ¹H NMR (400 MHz, d6-Acetone) δ=12.07-11.60 (m, 1H), 9.36 (br s, 1H), 7.05 (d, J=7.8 Hz, 1H), 6.98 (s, 1H), 6.94 (d, J=7.7 Hz, 1H), 5.97 (s, 2H), 3.65-3.53 (m, 1H), 2.60 (br dd, J=8.2, 11.9 Hz, 1H), 2.31 (s, 3H), 2.26 (s, 3H), 1.78 (td, J=4.3, 8.7 Hz, 1H), 1.47 (dt, J=3.5, 7.4 Hz, 1H).

Example 21

Synthesis of (2-(4-ethoxyphenyl)cyclopropyl)(2,4,6-trihydroxyphenyl)methanone (2-(4-ethoxyphenyl)cyclopropyl)(2,4,6-trihydroxyphenyl)methanone was synthesized as described in Example 19, but 4-methylbenzaldehyde was replaced by 4-ethoxybenzaldehyde. Yield: 36%. MS (ESI): calculated, m/z 315.1 (MH⁺); found, 315.1. ¹H NMR (400 MHz, d6-Acetone) δ=12.20-11.55 (m, 2H), 9.76-9.05 (m, 1H), 7.28-7.17 (m, 2H), 6.97-6.85 (m, 2H), 5.97-5.86 (m, 2H), 4.25-4.12 (m, 1H), 4.10-3.99 (m, 2H), 3.14-3.07 (m, 2H), 2.03-1.91 (m, 1H), 1.42-1.33 (m, 3H).

Example 22

Synthesis of (2-(4-phenoxyphenyl)cyclopropyl)(2,4,6-trihydroxyphenyl) methanone (2-(4-phenoxyphenyl)cyclopropyl)(2,4,6-trihydroxyphenyl) methanone was synthesized as described in Example 19, but 4-methylbenzaldehyde was replaced by 4-phenoxybenzaldehyde. Yield: 20%. MS (ESI): calculated, m/z 363.1 (MH⁺); found, 363.0. ¹H NMR (400 MHz, d6-Acetone) δ=12.05-11.59 (m, 2H), 9.42 (br s, 1H), 7.43-7.35 (m, 2H), 7.30-7.23 (m, 2H), 7.17-7.10 (m, 1H), 7.03-6.97 (m, 2H), 6.97-6.91 (m, 2H), 5.97 (s, 2H), 3.87-3.74 (m, 1H), 2.64 (ddd, J=4.1, 6.4, 9.0 Hz, 1H), 1.85 (ddd, J=3.8, 5.3, 9.0 Hz, 1H), 1.46 (ddd, J=3.8, 6.5, 8.1 Hz, 1H).

Example 23

Synthesis of 3-(4-(4-chlorophenoxy)-2-(trifluoromethyl)phenyl)-1-(2,4,6-trihydroxyphenyl)propan-1-one 3-(4-(4-chlorophenoxy)-2-(trifluoromethyl)phenyl)-1-(2,4,6-trihydroxyphenyl)propan-1-one was synthesized as described in Example 16, but 2,4-bis(trifluoromethyl)benzaldehyde was replaced by 4-(4-chlorophenoxy)-2-(trifluoromethyl)benzaldehyde. Yield: 42%. MS (ESI): calculated, m/z 453.1 (MH⁺); found, 453.1. ¹H NMR (400 MHz, d6-Acetone) δ=11.77 (br s, 1H), 7.61 (d, J=8.5 Hz, 1H), 7.49-7.39 (m, 2H), 7.33 (d, J=2.5 Hz, 1H), 7.26 (dd, J=2.6, 8.5 Hz, 1H), 7.15-7.03 (m, 2H), 5.96 (s, 2H), 3.55-3.41 (m, 2H), 3.23-3.14 (m, 2H).

Example 24

Synthesis of 3-(4-(4-chlorophenoxy)-2-methylphenyl)-1-(2,4,6-trihydroxyphenyl)propan-1-one 3-(4-(4-chlorophenoxy)-2-methylphenyl)-1-(2,4,6-trihydroxyphenyl)propan-1-one was synthesized as described in Example 16, but 2,4-bis(trifluoromethyl)benzaldehyde was replaced by 4-(4-chlorophenoxy)-2-methylbenzaldehyde. Yield: 61%. MS (ESI): calculated, m/z 399.1 (MH⁺); found, 399.1. ¹H NMR (400 MHz, d6-Acetone) δ=12.24-11.55 (m, 2H), 9.37 (br s, 1H), 7.43-7.33 (m, 2H), 7.25 (d, J=8.3 Hz, 1H), 7.05-6.94 (m, 2H), 6.87 (d, J=2.4 Hz, 1H), 6.80 (dd, J=2.6, 8.3 Hz, 1H), 5.96 (s, 2H), 3.43-3.33 (m, 2H), 3.02-2.97 (m, 2H), 2.35 (s, 3H).

Example 25

Synthesis of (2-(4-(4-chlorophenoxy)-2-(trifluoromethyl)phenyl)cyclopropyl)(2,4,6-trihydroxyphenyl)methanone (2-(4-(4-chlorophenoxy)-2-(trifluoromethyl)phenyl)cyclopropyl)(2,4,6-trihydroxyphenyl)methanone was synthesized as described in Example 19, but 4-methylbenzaldehyde was replaced by 4-(4-chlorophenoxy)-2-(trifluoromethyl)benzaldehyde. Yield: 42%. MS (ESI): calculated, m/z 465.1 (MH⁺); found, 465.1. ¹H NMR (400 MHz, d6-Acetone) δ=11.76 (br s, 2H), 9.38 (br s, 1H), 7.51-7.42 (m, 3H), 7.34 (d, J=2.5 Hz, 1H), 7.23 (dd, J=2.4, 8.6 Hz, 1H), 7.15-7.07 (m, 2H), 5.97 (s, 2H), 3.93-3.81 (m, 1H), 2.98-2.85 (m, 1H), 1.83 (ddd, J=4.1, 5.2, 9.1 Hz, 1H), 1.66-1.57 (m, 1H).

Example 26

Synthesis of (2-(4-(4-chlorophenoxy)-2-methylphenyl)cyclopropyl)(2,4,6-trihydroxyphenyl)methanone (0MTIC90)

(2-(4-(4-chlorophenoxy)-2-methylphenyl)cyclopropyl)(2,4,6-trihydroxyphenyl)methanone was synthesized as described in Example 19, but 4-methylbenzaldehyde was replaced by 4-(4-chlorophenoxy)-2-methylbenzaldehyde. Yield: 33%. MS (ESI): calculated, m/z 411.1 (MH⁺); found, 411.1. ¹H NMR (400 MHz, d6-Acetone) δ=12.15-11.51 (m, 2H), 7.44-7.36 (m, 2H), 7.22 (d, J=8.4 Hz, 1H), 7.05-6.97

(m, 2H), 6.89 (d, J=2.3 Hz, 1H), 6.80 (dd, J=2.5, 8.4 Hz, 1H), 5.99 (s, 2H), 3.71-3.59 (m, 1H), 2.69-2.58 (m, 1H), 2.35 (s, 3H), 1.81 (ddd, J=3.7, 5.1, 8.8 Hz, 1H), 1.57-1.44 (m, 1H).

Example 27

Synthesis of (E)-3-(4-(4-fluorophenoxy)-2-methylphenyl)-1-(2,4,6-trihydroxyphenyl)prop-2-en-1-one (E)-3-(4-(4-fluorophenoxy)-2-methylphenyl)-1-(2,4,6-trihydroxyphenyl)prop-2-en-1-one was synthesized as described in Example 9, but 2,4-bis(trifluoromethyl)benzaldehyde was replaced by 4-(4-fluorophenoxy)-2-methylbenzaldehyde. Yield: 64%. MS (ESI): calculated, m/z 381.1 (MH$^+$); found, 381.0. $^1$H NMR (400 MHz, d6-Acetone) δ=12.41-11.77 (m, 2H), 9.39 (br s, 1H), 8.17-8.11 (m, 1H), 8.09-8.01 (m, 1H), 7.73 (d, J=8.5 Hz, 1H), 7.27-7.18 (m, 2H), 7.18-7.09 (m, 2H), 6.91 (d, J=2.5 Hz, 1H), 6.85 (dd, J=2.5, 8.5 Hz, 1H), 6.00 (s, 2H), 2.48 (s, 3H).

Example 28

Synthesis of (E)-3-(4-(4-(trifluoromethyl)phenoxy) phenyl)-1-(2,4,6-trihydroxyphenyl)prop-2-en-1-one (E)-3-(4-(4-(trifluoromethyl)phenoxy)phenyl)-1-(2,4,6-trihydroxyphenyl)prop-2-en-1-one was synthesized as described in Example 9, but 2,4-bis(trifluoromethyl)benzaldehyde was replaced by 4-(4-(trifluoromethyl)phenoxy)benzaldehyde. Yield: 54%. MS (ESI): calculated, m/z 417.1 (MH$^+$); found, 417.1. $^1$H NMR (400 MHz, d6-Acetone) δ=12.46-11.81 (m, 1H), 9.50 (br s, 1H), 8.25 (d, J=15.6 Hz, 1H), 7.87-7.73 (m, 5H), 7.26 (d, J=8.5 Hz, 2H), 7.22-7.17 (m, 2H), 6.01 (s, 2H).

Example 29

Synthesis of (2-(4-(2,4-dichlorophenoxy)phenyl) cyclopropyl)(2,4,6-trihydroxyphenyl) methanone (2-(4-(2,4-dichlorophenoxy)phenyl)cyclopropyl)(2,4,6-trihydroxyphenyl) methanone was synthesized as described in Example 2, but 4-chlorobenzaldehyde was replaced by 4-(2,4-dichlorophenoxy)benzaldehyde. Yield: 1.4%. MS: m/z 431.0, [M+H]$^+$; $^1$H NMR (500 MHz, d$_6$-acetone); δ 10.9 (s, 3), 7.62 (d, J=2.4 Hz, 1), 7.39 (dd, J=8.8, 2.4 Hz, 1), 7.29 (d, J=8.4 Hz, 2), 7.05 (d, J=8.8 Hz, 1), 6.95 (d, J=8.4 Hz, 2), 5.96 (s, 2), 3.80 (dt, J=5.6, 4.7 Hz, 1), 2.72-2.52 (m, 1), 1.92-1.76 (m, 1), 1.45 (dt, J=6.6, 5.5 Hz, 1).

Example 30

Synthesis of 3-(4-chlorophenyl)-2-methyl-1-(2,4,6-trihydroxyphenyl)propan-1-one

To a stirred solution of 1-(2,4,6-trihydroxyphenyl)propan-1-one (1 g, 5.48 mmol) in dry DMF at 0° C., under N$_2$ was added NaH (0.65 g, 27.4 mmol) in dry DMF:toluene (5 mL each) dropwise and stirred at 0° C. for 1 h. Afterwards, MOMCl (1.66 mL, 21.9 mmol) was added slowly and reaction was allowed to stir at rt overnight. Crude reaction was extracted with EtOAc (50 mL) and washed with 10% NaOH. The organic layer was washed with satd. NaHCO$_3$ and brine. Then, the organic layer was dried over anhydrous Na$_2$SO$_4$ and evaporated under vacuum to yield an oily residue. Product 1 was isolated by chromatography on silica gel. Yield: 50%. MS: m/z 314 [M+H]$^+$.

KOH (0.107 g, 1.92 mmol) was added to dry methanol (5 mL) under N$_2$ and stirred until KOH disappeared. Then, a solution of 4-chlorobenzaldehyde (0.213 g, 1.51 mmol) and 1-(2,4,6-tris(methoxymethoxy)phenyl)propan-1-one (0.43 g, 1.37 mmol) in dry methanol (5 mL) was added and heated at 40° C. until reaction completion. Crude was concentrated in vacuo, extracted with EtOAc (3×10 mL) and washed with brine. Then, the organic layer was dried over anhydrous Na$_2$SO$_4$ and evaporated under vacuum to yield an oily residue. Product was isolated by chromatography on silica gel. Yield: 50%. MS: m/z 436 [M+H]$^+$.

A solution of 3-(4-chlorophenyl)-2-methyl-1-(2,4,6-tris (methoxymethoxy)phenyl)prop-2-en-1-one (0.1 g, 0.22 mmol) in dry MeOH:THF (3 mL each) was purged with N$_2$ and then 0.02 g of Pd/C was added and the mixture was purged with N$_2$. Then, a H$_2$ balloon was attached and the reaction mixture was stirred for 1 h. Afterwards, crude product was filtered and concentrated. No further purification was required and it was used for next reaction. A solution of 3-(4-chlorophenyl)-2-methyl-1-(2,4,6-tris (methoxymethoxy)phenyl)propan-1-one in dry DCM: MeOH (5 mL:1 mL) was added p-TSOH (0.1 g, 5 eq) and allowed to stir at rt overnight. The crude reaction was quenched with water and extracted with EtOAc (3×10 mL). The organic layer was washed with satd. NaHCO$_3$, dried over anhydrous Na$_2$SO$_4$, and evaporated under vacuum to yield a solid residue. Product was purified by reverse phase HPLC (80% Water:ACN 20%, with 0.1% TFA, to 100% ACN over 15 minutes. Compound was obtained as a white solid in 20% yield; MS: calculated, m/z 306 [M+H]$^+$; $^1$H NMR (500 MHz, CD$_3$CN) δ 7.26 (d, J=8.0 Hz, 2), 7.19 (d, J=8.0 Hz, 2), 5.86 (s, 2), 4.13 (q, J=7.0 Hz, 1), 3.10 (dd, J=13.5, 6.0 Hz, 1), 2.56 (dd, J=14.0, 7.5 Hz, 1), 1.08 (d, J=6.5 Hz, 3).

Example 31

Synthesis of (E)-3-(2-methyl-4-phenoxyphenyl)-1-(2,4,6-trihydroxyphenyl)prop-2-en-1-one (E)-3-(2-methyl-4-phenoxyphenyl)-1-(2,4,6-trihydroxyphenyl)prop-2-en-1-one was synthesized as described in Example 9, but 2,4-bis(trifluoromethyl)benzaldehyde was replaced by 2-methyl-4-phenoxybenzaldehyde. Yield: 64%. MS (ESI): calculated, m/z 363.1 (MH$^+$); found, 363.1. $^1$H NMR (400 MHz, d6-Acetone) δ=12.33-11.72 (m, 2H), 9.35 (br s, 1H), 8.20-8.00 (m, 2H), 7.73 (d, J=8.7 Hz, 1H), 7.50-7.38 (m, 2H), 7.20 (t, J=7.4 Hz, 1H), 7.09 (dd, J=0.8, 8.6 Hz, 2H), 6.92 (d, J=2.4 Hz, 1H), 6.86 (dd, J=2.4, 8.6 Hz, 1H), 6.00 (s, 2H), 2.48 (s, 3H).

Example 32

Synthesis of (E)-3-(4-(4-fluorophenoxy)-2-(trifluoromethyl)phenyl)-1-(2,4,6-trihydroxyphenyl)prop-2-en-1-one (E)-3-(4-(4-fluorophenoxy)-2-(trifluoromethyl)phenyl)-1-(2,4,6-trihydroxyphenyl)prop-2-en-1-one was synthesized as described in Example 9, but 2,4-bis(trifluoromethyl) benzaldehyde was replaced by 4-(4-fluorophenoxy)-2-(trifluoromethyl)benzaldehyde. Yield: 21%. MS (ESI): calculated, m/z 435.1 (MH$^+$); found, 435.1. $^1$H NMR (400 MHz, d6-Acetone) δ=12.28-11.75 (m, 2H), 9.46 (br s, 1H), 8.26-

8.19 (m, 1H), 8.11-8.03 (m, 1H), 8.01 (d, J=8.8 Hz, 1H), 7.36 (d, J=2.6 Hz, 1H), 7.31-7.21 (m, 5H), 6.01 (s, 2H).

Example 33

Synthesis of 3-(2-methyl-4-phenoxyphenyl)-1-(2,4,6-trihydroxyphenyl)propan-1-one 3-(2-methyl-4-phenoxyphenyl)-1-(2,4,6-trihydroxyphenyl)propan-1-one was synthesized as described in Example 16, but 2,4-bis(trifluoromethyl)benzaldehyde was replaced by 2-methyl-4-phenoxybenzaldehyde. Yield: 58%. MS (ESI): calculated, m/z 365.1 (MH$^+$); found, 365.0. $^1$H NMR (400 MHz, d6-Acetone) δ=12.28-11.44 (m, 2H), 9.29 (br s, 1H), 7.41-7.31 (m, 2H), 7.23 (d, J8.3 Hz, 1H), 7.11 (t, J=7.4 Hz, 1H), 6.98 (dd, J=0.9, 8.7 Hz, 2H), 6.85 (d, J=2.4 Hz, 1H), 6.78 (dd, J=2.5, 8.3 Hz, 1H), 5.96 (s, 2H), 3.43-3.33 (m, 2H), 3.01-2.98 (m, 2H), 2.35 (s, 3H).

Example 34

Synthesis of 3-(4-(4-fluorophenoxy)-2-methylphenyl)-1-(2,4,6-trihydroxyphenyl)propan-1-one 3-(4-(4-fluorophenoxy)-2-methylphenyl)-1-(2,4,6-trihydroxyphenyl)propan-1-one was synthesized as described in Example 16, but 2,4-bis(trifluoromethyl)benzaldehyde was replaced by 4-(4-fluorophenoxy)-2-methylbenzaldehyde. Yield: 86%. MS (ESI): calculated, m/z 383.1 (MH$^+$); found, 383.1. $^1$H NMR (400 MHz, d6-Acetone) δ=11.81 (br s, 2H), 9.52-9.00 (m, 1H), 7.22 (d, J=8.5 Hz, 1H), 7.19-7.09 (m, 2H), 7.06-6.99 (m, 2H), 6.83 (d, J=2.5 Hz, 1H), 6.76 (dd, J=2.6, 8.2 Hz, 1H), 5.96 (s, 2H), 3.41-3.33 (m, 2H), 2.98 (br s, 2H), 2.34 (s, 3H).

Example 35

Synthesis of 3-(4-(4-(trifluoromethyl)phenoxy)phenyl)-1-(2,4,6-trihydroxyphenyl)propan-1-one 3-(4-(4-(trifluoromethyl)phenoxy)phenyl)-1-(2,4,6-trihydroxyphenyl)propan-1-one was synthesized as described in Example 16, but 2,4-bis(trifluoromethyl)benzaldehyde was replaced by 4-(4-(trifluoromethyl)phenoxy)benzaldehyde. Yield: 57%. MS (ESI): calculated, m/z 419.1 (MH$^+$); found, 419.1. $^1$H NMR (400 MHz, d6-Acetone) δ=11.84 (br s, 2H), 9.40 (br s, 1H), 7.71 (d, J=8.7 Hz, 2H), 7.40 (d, J=8.5 Hz, 2H), 7.13 (d, J=8.5 Hz, 2H), 7.09-7.03 (m, 2H), 5.97 (s, 2H), 3.48-3.41 (m, 2H), 3.04 (d, J=7.9 Hz, 2H).

Example 36

Synthesis of (2-(4-(4-fluorophenoxy)-2-methylphenyl)cyclopropyl)(2,4,6-trihydroxyphenyl)methanone (2-(4-(4-fluorophenoxy)-2-methylphenyl)cyclopropyl)(2,4,6-trihydroxyphenyl)methanone was synthesized as described in Example 19, but 4-methylbenzaldehyde was replaced by 4-(4-fluorophenoxy)-2-methylbenzaldehyde. Yield: 36%. MS (ESI): calculated, m/z 395.1 (MH$^+$); found, 395.0. $^1$H NMR (400 MHz, d6-Acetone) δ=12.11-11.68 (m, 2H), 9.33 (br s, 1H), 7.22-7.11 (m, 3H), 7.08-7.00 (m, 2H), 6.84 (d, J=2.4 Hz, 1H), 6.75 (dd, J=2.5, 8.4 Hz, 1H), 5.98 (s, 2H), 3.67-3.57 (m, 1H), 2.61 (ddd, J=4.5, 6.8, 8.6 Hz, 1H), 2.34 (s, 3H), 1.81 (ddd, J=3.6, 5.1, 8.8 Hz, 1H), 1.55-1.46 (m, 1H).

Example 37

Synthesis of 3-(4-(4-fluorophenoxy)-2-(trifluoromethyl)phenyl)-1-(2,4,6-trihydroxyphenyl)propan-1-one 3-(4-(4-fluorophenoxy)-2-(trifluoromethyl)phenyl)-1-(2,4,6-trihydroxyphenyl)propan-1-one was synthesized as described in Example 16, but 2,4-bis(trifluoromethyl)benzaldehyde was replaced by 4-(4-fluorophenoxy)-2-(trifluoromethyl)benzaldehyde. Yield: 46%. MS (ESI): calculated, m/z 437.1 (MH$^+$); found, 437.1. $^1$H NMR (400 MHz, d6-Acetone) δ=11.85-11.44 (m, 2H), 9.34 (br s, 1H), 7.58 (d, J=8.5 Hz, 1H), 7.27 (d, J=2.6 Hz, 1H), 7.26-7.11 (m, 5H), 5.96 (s, 2H), 3.50-3.40 (m, 2H), 3.20-3.13 (m, 2H).

Example 38

Synthesis of (2-(4-methoxyphenyl)cyclopropyl)(2,4,6-trihydroxyphenyl)methanone (2-(4-methoxyphenyl)cyclopropyl)(2,4,6-trihydroxyphenyl)methanone was synthesized as described in Example 19, but 4-methylbenzaldehyde was replaced by 4-methoxybenzaldehyde. Yield: 19%. MS (ESI): calculated, m/z 301.1 (MH$^+$); found, 301.0. $^1$H NMR (400 MHz, d6-Acetone) δ=12.05-11.53 (m, 2H), 9.64-9.31 (m, 1H), 7.30-7.20 (m, 2H), 6.97-6.87 (m, 2H), 5.96-5.89 (m, 21-), 4.25-4.15 (m, 1H), 3.83-3.78 (m, 3H), 3.13-3.10 (m, 2H), 1.99 (td, J=6.0, 8.3 Hz, 1H).

Example 39

Synthesis of (2-(2-methyl-4-phenoxyphenyl)cyclopropyl)(2,4,6-trihydroxyphenyl)methanone (2-(2-methyl-4-phenoxyphenyl)cyclopropyl)(2,4,6-trihydroxyphenyl)methanone was synthesized as described in Example 19, but 4-methylbenzaldehyde was replaced by 2-methyl-4-phenoxybenzaldehyde. Yield: 48%. MS (ESI): calculated, m/z 377.1 (MH$^+$); found, 377.0. $^1$H NMR (400 MHz, d6-Acetone) δ=12.16-11.44 (m, 2H), 9.66-9.12 (m, 1H), 7.42-7.33 (m, 2H), 7.19 (d, J=8.4 Hz, 1H), 7.16-7.09 (m, 1H), 6.99 (d, J=8.4 Hz, 2H), 6.86 (s, 1H), 6.79-6.74 (m, 1H), 5.98 (s, 2H), 3.67-3.56 (m, 1H), 2.62 (br dd, J=8.2, 11.8 Hz, 1H), 2.35 (s, 3H), 1.82 (td, J=4.3, 8.8 Hz, 1H), 1.50 (dt, J=3.6, 7.4 Hz, 1H).

Example 40

Synthesis of (E)-1-(3-chloro-2,4,6-trihydroxyphenyl)-3-(2-methyl-4-phenoxyphenyl)prop-2-en-1-one To a solution of (E)-3-(2-methyl-4-phenoxy-phenyl)-1-(2,4,6-trihydroxyphenyl)prop-2-en-1-one (Example 31, 20.00 mg, 55.19 umol) in CHCl$_3$ (1.00 mL) was added sulfuryl chloride (8.19 mg, 60.71 umol) and EtOH (20.00 uL), and the mixture was stirring at 20° C. for 1 hour. The solvent was evaporated under vacuum. The residue was purified by prep-HPLC (Phenomenex Synergi C18 150*25*10 um, 60-90% B in 11 mins; buffer A=0.1% TFA-H$_2$O, buffer B=0.1% TFA-Acetonitrile) to afford 15 mg of the title compound as yellow solid. Yield: 68%. MS (ESI): calculated, m/z 397.1 (MH$^+$); found, 397.0. $^1$H NMR (400 MHz, d6-Acetone) δ=14.07 (br s, 1H), 10.84 (br s, 1H), 9.86 (br s, 1H), 8.13 (d, J=2.6 Hz, 2H), 7.76 (d, J=8.7 Hz, 1H), 7.49-7.40 (m, 2H), 7.25-7.17 (m, 1H), 7.14-7.06 (m, 2H), 6.97-6.84 (m, 2H), 6.28 (s, 1H), 2.50 (s, 3H).

Example 41

Synthesis of 1-(3-chloro-2,4,6-trihydroxyphenyl)-3-(2-methyl-4-phenoxyphenyl)propan-1-one 1-(3-chloro-2,4,6-trihydroxyphenyl)-3-(2-methyl-4-phenoxyphenyl)propan-1-one was synthesized as described in Example 40, but (E)-3-(2-methyl-4-phenoxy-phenyl)-1-(2,4,6-trihydroxyphenyl)prop-2-en-1-one was replaced by 3-(2-methyl-4-phenoxyphenyl)-1-(2,4,6-trihydroxyphenyl)propan-1-one. Yield: 68%. MS (ESI): calculated, m/z 399.1 (MH$^+$); found, 399.0. $^1$H NMR (400 MHz, d6-Acetone) δ=13.56 (br s, 1H), 10.75 (br s, 1H), 10.13-9.61 (m, 1H), 7.43-7.34 (m, 2H), 7.23 (d, J=8.3 Hz, 1H), 7.16-7.08 (m, 1H), 7.02-6.95 (m, 2H), 6.85 (d, J=2.5 Hz, 1H), 6.78 (dd, J=2.6, 8.2 Hz, 1H), 6.24 (s, 1H), 3.47-3.36 (m, 2H), 3.02 (br d, J=3.8 Hz, 2H), 2.35 (s, 3H).

Example 42

Synthesis of (3-chloro-2,4,6-trihydroxyphenyl)(2-(2-methyl-4-phenoxyphenyl)cyclopropyl)methanone (3-chloro-2,4,6-trihydroxyphenyl)(2-(2-methyl-4-phenoxyphenyl)cyclopropyl)methanone was synthesized as described in Example 40, but (E)-3-(2-methyl-4-phenoxy-phenyl)-1-(2,4,6-trihydroxyphenyl)prop-2-en-1-one was replaced by (2-(2-methyl-4-phenoxyphenyl)cyclopropyl)-(2,4,6-trihydroxyphenyl)methanone. Yield: 23%. MS (ESI): calculated, m/z 411.1 (MH$^+$); found, 411.1. $^1$H NMR (400 MHz, d6-Acetone) δ=14.07-13.40 (m, 1H), 10.84 (br s, 1H), 7.41-7.34 (m, 2H), 7.20 (d, J=8.4 Hz, 1H), 7.16-7.10 (m, 1H), 7.02-6.97 (m, 2H), 6.86 (d, J=2.5 Hz, 1H), 6.77 (dd, J=2.6, 8.4 Hz, 1H), 6.29 (s, 1H), 3.64 (td, J=4.8, 7.9 Hz, 1H), 2.66 (ddd, J=4.5, 7.0, 8.7 Hz, 1H), 2.34 (s, 3H), 1.85 (ddd, J=3.6, 5.1, 8.8 Hz, 1H), 1.61-1.52 (m, 1H).

Example 43

(2-(4-(2,4-difluorophenoxy)phenyl)cyclopropyl)(2,4,6-trihydroxyphenyl) methanone (2-(4-(2,4-dichlorophenoxy)phenyl)cyclopropyl)(2,4,6-trihydroxyphenyl) methanone was synthesized as described in Example 2, but 4-chlorobenzaldehyde was replaced by 4-(2,4-difluorophenoxy)benzaldehyde. Yield: 1.4%. MS: 399.1, [M+H]$^+$; $^1$H NMR (500 MHz, d$_6$-DMSO); δ 12.2 (s, 2), 10.4 (s, 1), 7.47 (dd, J=14.2, 5.7 Hz, 1), 7.37-7.16 (m, 3), 7.10 (dd, J=26.0, 18.0 Hz, 1), 6.88 (d, J=8.3 Hz, 2), 5.99-5.61 (m, 2), 3.85-3.54 (m, 1), 3.35 (s, 3), 2.67-2.31 (m, 3), 1.90-1.62 (m, 1), 1.46 (d, J=1.9 Hz, 1).

Example 44

Synthesis of (2-(4-(4-fluorophenoxy)-2-(trifluoromethyl)phenyl)cyclopropyl)(2,4,6-trihydroxyphenyl)methanone (2-(4-(4-fluorophenoxy)-2-(trifluoromethyl)phenyl)cyclopropyl)(2,4,6-trihydroxyphenyl)methanone was synthesized as described in Example 19, but 4-methylbenzaldehyde was replaced by 4-(4-fluorophenoxy)-2-(trifluoromethyl)benzaldehyde. Yield: 30%. MS (ESI): calculated, m/z 449.1 (MH$^+$); found, 448.9. $^1$H NMR (400 MHz, d6-Acetone) δ=11.75 (br s, 2H), 9.36 (br s, 1H), 7.43 (d, J=8.5 Hz, 1H), 7.28 (d, J=2.6 Hz, 1H), 7.26-7.19 (m, 2H), 7.19-7.13 (m, 3H), 5.97 (s, 2H), 3.85 (td, J=5.1, 8.1 Hz, 1H), 2.98-2.86 (m, 1H), 1.83 (ddd, J=4.0, 5.3, 9.1 Hz, 1H), 1.60 (ddd, J=4.0, 6.7, 8.1 Hz, 1H).

Example 45

Synthesis of 1-(3-chloro-2,4,6-trihydroxyphenyl)-3-(4-(4-fluorophenoxy)phenyl)propan-1-one 1-(3-chloro-2,4,6-trihydroxyphenyl)-3-(4-(4-fluorophenoxy)phenyl)propan-1-one was synthesized as described in Example 40, but (E)-3-(2-methyl-4-phenoxy-phenyl)-1-(2,4,6-trihydroxyphenyl)prop-2-en-1-one was replaced by 3-(4-(4-fluorophenoxy)phenyl)-1-(2,4,6-trihydroxyphenyl)propan-1-one. Yield: 53%. MS (ESI): calculated, m/z 403.1 (MH$^+$); found, 403.0. $^1$H NMR (400 MHz, d6-Acetone) δ=13.55 (br s, 1H), 10.83 (br s, 1H), 9.89 (br s, 1H), 7.34-7.29 (m, 2H), 7.20-7.12 (m, 2H), 7.07-7.00 (m, 2H), 6.95-6.90 (m, 2H), 6.26 (s, 1H), 3.49-3.41 (m, 2H), 3.01 (d, J=7.9 Hz, 2H).

Example 46

Synthesis of (3-chloro-2,4,6-trihydroxyphenyl)(2-(4-(4-fluorophenoxy)phenyl)cyclopropyl)methanone (3-chloro-2,4,6-trihydroxyphenyl)(2-(4-(4-fluorophenoxy)phenyl)cyclopropyl)methanone was synthesized as described in Example 40, but (E)-3-(2-methyl-4-phenoxy-phenyl)-1-(2,4,6-trihydroxyphenyl)prop-2-en-1-one was replaced by (2-(4-(4-fluorophenoxy)phenyl)cyclopropyl)(2,4,6-trihydroxyphenyl)methanone. Yield: 60%. MS (ESI): calculated, m/z 415.1 (MH$^+$); found, 415.0. $^1$H NMR (400 MHz, d6-Acetone) δ=13.54 (br s, 1H), 10.66 (br s, 1H), 9.76 (br s, 1H), 7.31-7.23 (m, 2H), 7.21-7.12 (m, 2H), 7.08-7.01 (m, 2H), 6.97-6.90 (m, 2H), 6.25 (s, 1H), 3.90-3.67 (m, 1H), 2.69 (ddd, J=4.1, 6.5, 9.0 Hz, 1H), 1.89 (ddd, J=3.9, 5.4, 9.1 Hz, 1H), 1.51 (ddd, J=3.8, 6.6, 8.0 Hz, 1H).

Example 47

Synthesis of (2-(4-chloro-2-(trifluoromethyl)phenyl)cyclopropyl)(2,4,6-trihydroxyphenyl)methanone (2-(4-chloro-2-(trifluoromethyl)phenyl)cyclopropyl)(2,4,6-trihydroxyphenyl)methanone was synthesized as described in Example 19, but 4-methylbenzaldehyde was replaced by 4-chloro-2-(trifluoromethyl)benzaldehyde. Yield: 41%. MS (ESI): calculated, m/z 373.0 (MH$^+$); found, 372.8. $^1$H NMR (400 MHz, d6-Acetone) δ=11.92-11.42 (m, 2H), 9.33 (br s, 1H), 7.70 (d, J=2.0 Hz, 1H), 7.63 (dd, J=2.0, 8.4 Hz, 1H), 7.45 (d, J=8.4 Hz, 1H), 5.97 (s, 2H), 3.86 (td, J=5.1, 8.0 Hz, 1H), 2.98-2.78 (m, 1H), 1.86 (ddd, J=4.1, 5.4, 9.2 Hz, 1H), 1.64 (ddd, J=4.1, 6.7, 8.2 Hz, 1H).

Example 48

Synthesis of (E)-1-(3-chloro-2,4,6-trihydroxyphenyl)-3-(4-(4-fluorophenoxy)phenyl)prop-2-en-1-one (E)-1-(3-chloro-2,4,6-trihydroxyphenyl)-3-(4-(4-fluorophenoxy)phenyl)prop-2-en-1-one was synthesized as described in Example 40, but (E)-3-(2-methyl-4-phenoxy-phenyl)-1-(2,4,6-trihydroxyphenyl)prop-2-en-1-one was replaced by (E)-3-(4-(4-fluorophenoxy)phenyl)-1-(2,4,6-trihydroxyphenyl)prop-2-en-1-one. Yield: 19%. MS (ESI): calculated, m/z 401.1 (MH$^+$); found, 401.0. $^1$H NMR (400 MHz, d6-Acetone) δ=14.07 (br s, 1H), 10.91 (br s, 1H), 10.02 (br s, 1H), 8.20 (d, J=15.6 Hz, 1H), 7.84 (d, J=15.7 Hz, 1H), 7.78-7.70 (m, 2H), 7.28-7.13 (m, 4H), 7.09-6.99 (m, 2H), 6.30 (s, 1H).

Example 49

Synthesis of 1-(3-chloro-2,4,6-trihydroxyphenyl)-3-(4-(4-fluorophenoxy)-2-(trifluoromethyl)phenyl)propan-1-one 1-(3-chloro-2,4,6-trihydroxyphenyl)-3-(4-(4-fluorophenoxy)-2-(trifluoromethyl)phenyl)propan-1-one was synthesized as described in Example 40, but (E)-3-(2-methyl-4-phenoxy-phenyl)-1-(2,4,6-trihydroxyphenyl)prop-2-en-1-one was replaced by 3-(4-(4-fluorophenoxy)-2-(trifluoromethyl)phenyl)-1-(2,4,6-trihydroxyphenyl)propan-1-one. Yield: 56%. MS (ESI): calculated, m/z 471.1 (MH$^+$); found, 470.9. $^1$H NMR (400 MHz, d6-Acetone) δ=13.52 (br s, 1H), 10.86 (br s, 1H), 9.98 (br s, 1H), 7.59 (d, J=8.5 Hz, 1H), 7.28 (d, J=2.6 Hz, 1H), 7.25-7.18 (m, 3H), 7.18-7.12 (m, 2H), 6.27 (s, 1H), 3.58-3.35 (m, 2H), 3.23-3.15 (m, 2H).

Example 50

Synthesis of 1-(3-chloro-2,4,6-trihydroxyphenyl)-3-(4-(4-fluorophenoxy)-2-methylphenyl)propan-1-one 1-(3-chloro-2,4,6-trihydroxyphenyl)-3-(4-(4-fluorophenoxy)-2-methylphenyl)propan-1-one was synthesized as described in Example 40, but (E)-3-(2-methyl-4-phenoxy-phenyl)-1-(2,4,6-trihydroxyphenyl)prop-2-en-1-one was replaced by 3-(4-(4-fluorophenoxy)-2-methylphenyl)-1-(2,4,6-trihydroxyphenyl)propan-1-one. Yield: 47%. MS (ESI): calculated, m/z 417.1 (MH$^+$); found, 417.1. $^1$H NMR (400 MHz, d6-Acetone) δ=13.54 (br s, 1H), 10.80 (br s, 1H), 9.85 (br s, 1H), 7.22 (d, J=8.3 Hz, 1H), 7.18-7.12 (m, 2H), 7.06-7.00 (m, 2H), 6.83 (d, J=2.5 Hz, 1H), 6.76 (dd, J=2.6, 8.2 Hz, 1H), 6.24 (s, 1H), 3.44-3.36 (m, 2H), 3.03-2.98 (m, 2H), 2.34 (s, 3H).

Example 51

Synthesis of (3-chloro-2,4,6-trihydroxyphenyl)(2-(4-(4-fluorophenoxy)-2-(trifluoromethyl)phenyl)cyclopropyl)methanone (3-chloro-2,4,6-trihydroxyphenyl)(2-(4-(4-fluorophenoxy)-2-(trifluoromethyl)phenyl)cyclopropyl)methanone was synthesized as described in Example 40, but (E)-3-(2-methyl-4-phenoxy-phenyl)-1-(2,4,6-trihydroxyphenyl)prop-2-en-1-one was replaced by (2-(4-(4-fluorophenoxy)-2-(trifluoromethyl)phenyl)cyclopropyl)(2,4,6-trihydroxyphenyl)-methanone. Yield: 56%. MS (ESI): calculated, m/z 483.1 (MH$^+$); found, 483.0. $^1$H NMR (400 MHz, d6-Acetone) δ=13.51 (br s, 1H), 10.79 (br s, 1H), 9.92 (br s, 1H), 7.45 (d, J=8.7 Hz, 1H), 7.29 (d, J=2.5 Hz, 1H), 7.26-7.20 (m, 2H), 7.19-7.13 (m, 3H), 6.27 (s, 1H), 4.01-3.60 (m, 1H), 1.93-1.81 (m, 1H), 1.72-1.61 (m, 1H).

Example 52

Synthesis of (3-chloro-2,4,6-trihydroxyphenyl)(2-(4-(4-fluorophenoxy)-2-methylphenyl)cyclopropyl)methanone (3-chloro-2,4,6-trihydroxyphenyl)(2-(4-(4-fluorophenoxy)-2-methylphenyl)cyclopropyl)methanone was synthesized as described in Example 40, but (E)-3-(2-methyl-4-phenoxy-phenyl)-1-(2,4,6-trihydroxyphenyl)prop-2-en-1-one was replaced by (2-(4-(4-fluorophenoxy)-2-methylphenyl)cyclopropyl)(2,4,6-trihydroxyphenyl)methanone. Yield: 40%. MS (ESI): calculated, m/z 429.1 (MH$^+$); found, 429.1. $^1$H NMR (400 MHz, d6-Acetone) δ=13.74 (br s, 1H), 10.87 (br s, 1H), 10.05 (br s, 1H), 7.23-7.12 (m, 3H), 7.07-7.00 (m, 2H), 6.84 (d, J=2.3 Hz, 1H), 6.75 (dd, J=2.4, 8.4 Hz, 1H), 6.29 (s, 1H), 3.88-3.39 (m, 1H), 2.78-2.44 (m, 1H), 2.33 (s, 3H), 1.84 (ddd, J=3.8, 5.0, 8.8 Hz, 1H), 1.55 (dt, J=3.7, 7.5 Hz, 1H).

Example 53

Synthesis of (2-(4-chloro-2-methylphenyl)cyclopropyl)(2,4,6-trihydroxyphenyl)methanone (2-(4-chloro-2-methylphenyl)cyclopropyl)(2,4,6-trihydroxyphenyl)methanone was synthesized as described in Example 19, but 4-methylbenzaldehyde was replaced by 4-chloro-2-methylbenzaldehyde. Yield: 42%. MS (ESI): calculated, m/z 319.1 (MH$^+$); found, 319.0. $^1$H NMR (400 MHz, d6-Acetone) δ=12.29-11.31 (m, 2H), 9.64-8.99 (m, 1H), 7.25-7.12 (m, 3H), 5.98 (s, 2H), 3.61 (td, J=4.9, 7.8 Hz, 1H), 2.60 (ddd, J=4.5, 6.8, 8.7 Hz, 1H), 2.36 (s, 3H), 1.82 (ddd, J=3.8, 5.2, 8.9 Hz, 1H), 1.50 (ddd, J=3.6, 6.9, 8.0 Hz, 1H).

Example 54

Synthesis of (3-chloro-2,4,6-trihydroxyphenyl)(2-(4-chloro-2-(trifluoromethyl)phenyl)cyclopropyl)methanone (3-chloro-2,4,6-trihydroxyphenyl)(2-(4-chloro-2-(trifluoromethyl)phenyl)cyclopropyl)methanone was synthesized as described in Example 40, but (E)-3-(2-methyl-4-phenoxy-phenyl)-1-(2,4,6-trihydroxyphenyl)prop-2-en-1-one was replaced by (2-(4-chloro-2-(trifluoromethyl)phenyl)cyclopropyl)(2,4,6-trihydroxyphenyl)methanone. Yield: 46%. MS (ESI): calculated, m/z 407.0 (MH$^+$); found, 406.7. $^1$H NMR (400 MHz, d6-Acetone) δ=13.46 (br s, 1H), 10.74 (br s, 1H), 9.88 (br s, 1H), 7.71 (s, 1H), 7.65 (br d, J=8.4 Hz, 1H), 7.47 (d, J=8.4 Hz, 1H), 6.25 (s, 1H), 3.94-3.80 (m, 1H), 2.93 (br s, 1H), 1.91 (td, J=4.7, 9.2 Hz, 1H), 1.75-1.68 (m, 1H).

Example 55

Synthesis of (3-chloro-2,4,6-trihydroxyphenyl)(2-(4-chlorophenyl)cyclopropyl)methanone (3-chloro-2,4,6-trihydroxyphenyl)(2-(4-chlorophenyl)cyclopropyl)methanone was synthesized as described in Example 40, but (E)-3-(2-methyl-4-phenoxy-phenyl)-1-(2,4,6-trihydroxyphenyl)prop-2-en-1-one was replaced by (2-

(4-chlorophenyl)cyclopropyl)(2,4,6-trihydroxyphenyl) methanone. Yield: 37%. MS (ESI): calculated, m/z 339.0 (MH$^+$); found, 338.6. $^1$H NMR (400 MHz, d6-Acetone) δ=13.54 (br s, 1H), 10.70 (br s, 1H), 9.92 (br s, 1H), 7.38-7.23 (m, 4H), 6.25 (s, 1H), 3.86-3.72 (m, 1H), 2.67 (ddd, J=4.1, 6.4, 9.0 Hz, 1H), 1.91 (ddd, J=4.0, 5.3, 9.1 Hz, 1H), 1.52 (ddd, J=4.0, 6.6, 8.0 Hz, 1H).

Example 56

Synthesis of (3-chloro-2,4,6-trihydroxyphenyl)(2-(4-chloro-2-methylphenyl)cyclopropyl)methanone (3-chloro-2,4,6-trihydroxyphenyl)(2-(4-chloro-2-methylphenyl)cyclopropyl)methanone was synthesized as described in Example 40, but (E)-3-(2-methyl-4-phenoxyphenyl)-1-(2,4,6-trihydroxyphenyl)prop-2-en-1-one was replaced by (2-(4-chloro-2-methylphenyl)cyclopropyl)-(2,4,6-trihydroxyphenyl)methanone. Yield: 45%. MS (ESI): calculated, m/z 353.0 (MH$^+$); found, 353.0. $^1$H NMR (400 MHz, d6-Acetone) δ=13.59 (br s, 1H), 10.73 (br s, 1H), 10.11-9.64 (m, 1H), 7.25-7.12 (m, 3H), 6.27 (s, 1H), 3.69-3.57 (m, 1H), 2.72-2.60 (m, 1H), 2.36 (s, 3H), 1.93-1.81 (m, 1H), 1.56 (dt, J=3.7, 7.4 Hz, 1H).

Example 57

Synthesis of (2-(2,4-bis(trifluoromethyl)phenyl)cyclopropyl)(2,4,6-trihydroxyphenyl)methanone (2-(2,4-bis(trifluoromethyl)phenyl)cyclopropyl)(2,4,6-trihydroxyphenyl)methanone was synthesized as described in Example 19, but 4-methylbenzaldehyde was replaced by 2,4-bis(trifluoromethyl)benzaldehyde. Yield: 93%. MS (ESI): calculated, m/z 407.1 (MH$^+$); found, 406.8. $^1$H NMR (400 MHz, d6-Acetone) δ=11.92-11.46 (m, 2H), 9.44-9.18 (m, 1H), 8.01-7.93 (m, 2H), 7.66 (d, J=8.2 Hz, 1H), 5.97 (s, 2H), 4.00-3.89 (m, 1H), 2.98 (br d, J=4.3 Hz, 1H), 1.94 (ddd, J=4.3, 5.4, 9.2 Hz, 1H), 1.74 (ddd, J=4.1, 6.5, 8.3 Hz, 1H).

Example 58

Synthesis of (2-(4-(trifluoromethyl)phenyl)cyclopropyl)(2,4,6-trihydroxyphenyl)methanone (2-(4-(trifluoromethyl)phenyl)cyclopropyl)(2,4,6-trihydroxyphenyl)methanone was synthesized as described in Example 19, but 4-methylbenzaldehyde was replaced by 4-(trifluoromethyl)benzaldehyde. Yield: 43%. MS (ESI): calculated, m/z 339.1 (MH$^+$); found, 338.7. $^1$H NMR (400 MHz, d6-Acetone) δ=11.98-11.49 (m, 2H), 9.34 (br s, 1H), 7.63 (d, J=8.2 Hz, 2H), 7.47 (d, J=8.3 Hz, 2H), 5.96 (s, 2H), 4.01-3.77 (m, 1H), 2.76-2.64 (m, 1H), 1.93 (ddd, J=3.9, 5.5, 9.2 Hz, 1H), 1.55 (ddd, J=3.9, 6.4, 8.2 Hz, 1H).

Example 59

Synthesis of 3,5-dihydroxy-2-(2-(4-phenoxyphenyl) cyclopropanecarbonyl)-4,6,6-tripropylcyclohexa-2,4-dienone A solution of [2-(4-phenoxyphenyl)cyclopropyl]-(2,4,6-trihydroxyphenyl)methanone (Example 22, 20.00 mg, 55.19 umol) and 1-iodopropane (34.80 mg, 204.75 umol, 20.00 uL, Sigma-Aldrich) in anhydrous MeOH (1.00 mL) was added NaOMe (9.84 mg, 182.13 umol, 3.30 eq) and stirred at 20° C. for 16 hours. The reaction mixture was cooled to 0° C. and acidified with 1 M aqueous HCl and then extracted with ethyl acetate (3×10 mL). The combined organic layers were dried over anhydrous Na$_2$SO$_4$ and evaporated under vacuum. The residue was purified by prep-HPLC (Phenomenex Synergi C18 150*25*10 um, 60-90% B in 11 mins; buffer A=0.1% TFA-H$_2$O, buffer B=0.1% TFA-Acetonitrile) to afford 9 mg of the title compound as yellow solid. Yield: 33%. MS (ESI): calculated, m/z 489.2 (MH$^+$); found, 489.3. $^1$H NMR (400 MHz, d6-Acetone) δ=7.46-7.35 (m, 2H), 7.28 (d, J=8.7 Hz, 2H), 7.13 (t, J=7.4 Hz, 1H), 7.05-6.93 (m, 4H), 4.24-4.13 (m, 1H), 2.79-2.68 (m, 1H), 2.54-2.43 (m, 2H), 1.96-1.77 (m, 5H), 1.59-1.44 (m, 3H), 1.18-1.00 (m, 4H), 0.95 (t, J=7.3 Hz, 3H), 0.86-0.79 (m, 4H), 0.78-0.71 (m, 3H).

Example 60

Synthesis of 3,5-dihydroxy-2-(2-(4-phenoxyphenyl) cyclopropanecarbonyl)-6,6-dipropylcyclohexa-2,4-dien-1one A solution of [2-(4-phenoxyphenyl)cyclopropyl]-(2,4,6-trihydroxyphenyl)methanone (Example 22, 20.00 mg, 55.19 umol) and 1-iodopropane (34.80 mg, 204.75 umol, 20.00 uL, Sigma-Aldrich) in anhydrous MeOH (1.00 mL) was added NaOMe (9.84 mg, 182.13 umol, 3.30 eq) and stirred at 20° C. for 16 hours. The reaction mixture was cooled to 0° C. and acidified with 1 M aqueous HCl and then extracted with ethyl acetate (3×10 mL). The combined organic layers were dried over anhydrous Na$_2$SO$_4$ and evaporated under vacuum. The residue was purified by prep-HPLC (Phenomenex Synergi C18 150*25*10 um, 60-90% B in 11 mins; buffer A=0.1% TFA-H$_2$O, buffer B=0.1% TFA-Acetonitrile) to afford 9 mg of the title compound as yellow solid. Yield: 10%. MS (ESI): calculated, m/z 447.6 (MH$^+$); found, 447.2. $^1$H NMR (400 MHz, d6-Acetone) δ=7.39-7.35 (m, 2H), 7.26 (d, J=8.8 Hz, 1H), 7.00-6.94 (m, 5H), 5.62 (s, 1H), 4.24-4.13 (m, 1H), 2.79-2.68 (m, 1H), 2.54-2.43 (m, 2H), 1.81-1.70 (m, 4H), 1.25-1.00 (m, 4H), 0.84-0.75 (m, 6H).

Example 61

Synthesis of 4,6,6-triethyl-2-(3-(4-(4-fluorophenoxy)phenyl)propanoyl)-3,5-dihydroxycyclohexa-2,4-dienone To a solution of (E)-3-[4-(4-fluorophenoxy)phenyl]-1-(2,4,6-trihydroxyphenyl)prop-2-en-1-one (Example 60, 200.00 mg, 545.94 umol) in MeOH (10.00 mL) was added Pd/C (50.00 mg) and stirred at 20° C. under H$_2$ (15 psi) for 15 mins. The reaction mixture was filtered and evaporated under vacuum. The residue was purified by prep-HPLC (Phenomenex Synergi C18 150*25*10 um, 60-90% B in 11 mins; buffer A=0.1% TFA-H$_2$O, buffer B=0.1% TFA-Acetonitrile) to obtain 180 mg of 3-(4-(4-fluorophenoxy)phenyl)-1-(2,4,6-trihydroxyphenyl)propan-1-one as yellowish solid. Yield: 74%. MS (ESI): calculated, m/z 367.1 (MH$^+$); found, 367.1. $^1$H NMR (400 MHz, d6-Acetone) δ=12.21-11.93 (m, 1H), 11.98-11.70 (m, 1H), 9.36 (br s, 1H), 7.31 (d, J=8.4 Hz, 2H), 7.22-7.10 (m, 2H), 7.09-6.98 (m, 2H), 6.93 (d, J=8.4 Hz, 2H), 5.96 (s, 2H), 3.41 (t, J=7.7 Hz, 2H), 3.00-2.91 (m, 2H).

4,6,6-triethyl-2-(3-(4-(4-fluorophenoxy)phenyl)propanoyl)-3,5-dihydroxycyclohexa-2,4-dienone was synthesized as described in Example 59, but [2-(4-phenoxyphenyl) cyclopropyl]-(2,4,6-trihydroxyphenyl)methanone and 1-iodopropane were was replaced by 3-(4-(4-fluorophenoxy)phenyl)-1-(2,4,6-trihydroxyphenyl)propan-1-one and iodoethane. Yield: 32%. MS (ESI): calculated, m/z 453.1 (MH⁺); found, 453.1. ¹H NMR (400 MHz, d6-Acetone) δ=7.34 (d, J=8.4 Hz, 2H), 7.20-7.11 (m, 2H), 7.07-7.00 (m, 2H), 6.95 (d, J=8.4 Hz, 2H), 3.41-3.30 (m, 2H), 2.99-2.88 (m, 2H), 2.56 (q, J=7.4 Hz, 2H), 2.03-1.84 (m, 4H), 1.12-0.98 (m, 3H), 0.68 (t, J=7.5 Hz, 6H).

Example 62

Synthesis of 4,6,6-triethyl-2-(2-(4-(4-fluorophenoxy)phenyl)cyclopropanecarbonyl)-3,5-dihydroxycyclohexa-2,4-dienone 4,6,6-triethyl-2-(2-(4-(4-fluorophenoxy)phenyl)cyclopropanecarbonyl)-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by 4,6,6-triethyl-2-(2-(4-(4-fluorophenoxy)phenyl)cyclopropanecarbonyl)-3,5-dihydroxycyclohexa-2,4-dienone and iodoethane. Yield: 32%. MS (ESI): calculated, m/z 465.2 (MH⁺); found, 465.2. ¹H NMR (400 MHz, d6-Acetone) δ=7.31-7.26 (m, 2H), 7.20-7.13 (m, 2H), 7.09-7.03 (m, 2H), 6.95 (d, J=8.7 Hz, 2H), 4.25-4.12 (m, 1H), 2.80-2.68 (m, 1H), 2.56 (q, J=7.4 Hz, 2H), 2.04-1.77 (m, 6H), 1.57-1.45 (m, 1H), 1.15-1.01 (m, 3H), 0.76-0.58 (m, 7H).

Example 63

Synthesis of 2-(3-(4-(4-fluorophenoxy)phenyl)propanoyl)-3,5-dihydroxy-6,6-dipropylcyclohexa-2,4-dienone 2-(3-(4-(4-fluorophenoxy)phenyl)propanoyl)-3,5-dihydroxy-6,6-dipropylcyclohexa-2,4-dienone and 2-(3-(4-(4-fluorophenoxy)phenyl)propanoyl)-3,5-dihydroxy-4,6,6-tripropylcyclohexa-2,4-dienone were synthesized as described in Example 59, but [2-(4-phenoxyphenyl)cyclopropyl]-(2,4,6-trihydroxyphenyl)methanone was replaced by (2-(4-(4-fluorophenoxy)phenyl)cyclopropyl)(2,4,6-trihydroxyphenyl)methanone. Yield: 14%. MS (ESI): calculated, m/z 453.2 (MH⁺); found, 453.1. ¹H NMR (400 MHz, d6-Acetone) δ=7.36-7.28 (m, 2H), 7.20-7.11 (m, 2H), 7.07-7.00 (m, 2H), 6.97-6.90 (m, 2H), 5.75 (s, 1H), 3.38-3.29 (m, 2H), 2.95-2.88 (m, 1H), 1.96-1.85 (m, 2H), 1.78 (dt, J=4.6, 12.3 Hz, 2H), 1.55-1.41 (m, 1H), 1.25-0.76 (m, 10H).

Example 64

Synthesis of 2-(3-(4-(4-fluorophenoxy)phenyl)propanoyl)-3,5-dihydroxy-4,6,6-tripropylcyclohexa-2,4-dienone 2-(3-(4-(4-fluorophenoxy)phenyl)propanoyl)-3,5-dihydroxy-6,6-dipropylcyclohexa-2,4-dienone and 2-(3-(4-(4-fluorophenoxy)phenyl)propanoyl)-3,5-dihydroxy-4,6,6-tripropylcyclohexa-2,4-dienone were synthesized as described in Example 59, but [2-(4-phenoxyphenyl)cyclopropyl]-(2,4,6-trihydroxyphenyl)methanone was replaced by (2-(4-(4-fluorophenoxy)phenyl)cyclopropyl)(2,4,6-trihydroxyphenyl)methanone. Yield: 12%. MS (ESI): calculated, m/z 495.2 (MH⁺); found, 495.2. ¹H NMR (400 MHz, d6-Acetone) ¹H NMR (400 MHz, Acetone) δ=7.33 (d, J=8.4 Hz, 2H), 7.20-7.11 (m, 2H), 7.08-7.00 (m, 2H), 6.98-6.90 (m, 2H), 3.41-3.31 (m, 2H), 2.99-2.88 (m, 1H), 2.58-2.45 (m, 2H), 1.99-1.79 (m, 3H), 1.55-1.43 (m, 2H), 1.19-0.98 (m, 4H), 0.98-0.90 (m, 3H), 0.84-0.75 (m, 6H).

Example 65

Synthesis of 2-(2-(4-(4-fluorophenoxy)phenyl)cyclopropanecarbonyl)-3,5-dihydroxy-6,6-dipropylcyclohexa-2,4-dienone 2-(2-(4-(4-fluorophenoxy)phenyl)cyclopropanecarbonyl)-3,5-dihydroxy-6,6-dipropylcyclohexa-2,4-dienone and 2-(2-(4-(4-fluorophenoxy)phenyl)cyclopropanecarbonyl)-3,5-dihydroxy-4,6,6-tripropylcyclohexa-2,4-dienone were synthesized as described in Example 59, but [2-(4-phenoxyphenyl)cyclopropyl]-(2,4,6-trihydroxyphenyl)methanone was replaced by (2-(4-(4-fluorophenoxy)phenyl)cyclopropyl)(2,4,6-trihydroxyphenyl)methanone. Yield: 11%. MS (ESI): calculated, m/z 465.2 (MH⁺); found, 465.1. ¹H NMR (400 MHz, d6-Acetone) δ=7.36-7.28 (m, 2H), 7.20-7.11 (m, 2H), 7.07-7.00 (m, 2H), 6.97-6.90 (m, 2H), 5.75 (s, 1H), 3.38-3.29 (m, 2H), 2.95-2.88 (m, 1H), 1.96-1.85 (m, 2H), 1.78 (dt, J=4.6, 12.3 Hz, 2H), 1.55-1.41 (m, 1H), 1.25-0.76 (m, 10H).

Example 66

Synthesis of 2-(2-(4-(4-fluorophenoxy)phenyl)cyclopropanecarbonyl)-3,5-dihydroxy-4,6,6-tripropylcyclohexa-2,4-dienone 2-(2-(4-(4-fluorophenoxy)phenyl)cyclopropanecarbonyl)-3,5-dihydroxy-6,6-dipropylcyclohexa-2,4-dienone and 2-(2-(4-(4-fluorophenoxy)phenyl)cyclopropanecarbonyl)-3,5-dihydroxy-4,6,6-tripropylcyclohexa-2,4-dienone were synthesized as described in Example 59, but [2-(4-phenoxyphenyl)cyclopropyl]-(2,4,6-trihydroxyphenyl)methanone was replaced by (2-(4-(4-fluorophenoxy)phenyl)cyclopropyl)(2,4,6-trihydroxyphenyl)methanone. Yield: 12%. MS (ESI): calculated, m/z 495.2 (MH⁺); found, 495.2. ¹H NMR (400 MHz, Acetone) δ=7.33 (d, J=8.4 Hz, 2H), 7.20-7.11 (m, 2H), 7.08-7.00 (m, 2H), 6.98-6.90 (m, 2H), 3.41-3.31 (m, 2H), 2.99-2.88 (m, 1H), 2.58-2.45 (m, 2H), 1.99-1.79 (m, 3H), 1.55-1.43 (m, 2H), 1.19-0.98 (m, 4H), 0.98-0.90 (m, 3H), 0.84-0.75 (m, 6H).

Example 67

Synthesis of (E)-3-(4-(4-fluorophenoxy)phenyl)-1-(2,4,6-trihydroxy-3-propylphenyl)prop-2-en-1-one (E)-3-(4-(4-fluorophenoxy)phenyl)-1-(2,4,6-trihydroxy-3-propylphenyl)prop-2-en-1-one was synthesized as described in Example 59, but [2-(4-phenoxyphenyl)cyclopropyl]-(2,4,6-trihydroxyphenyl)methanone was replaced by (E)-3-(4-(4-fluorophenoxy)phenyl)-1-(2,4,6-trihydroxyphenyl)prop-2-en-1-one. Yield: 7%. MS (ESI): calculated, m/z 409.1 (MH⁺); found, 409.0. ¹H NMR (400 MHz, d6-Acetone) δ=12.45 (s, 1H), 9.69 (br s, 1H), 7.66-7.54 (m, 2H), 7.25-7.17 (m, 2H), 7.16-7.10 (m, 2H), 7.09-7.04 (m, 2H), 6.08 (s, 1H), 5.55 (dd, J=3.0, 12.9 Hz, 1H), 3.20 (dd, J=12.9, 17.1 Hz, 1H), 2.80 (dd, J=3.0, 17.1 Hz, 1H), 2.61-2.48 (m, 3H), 1.55 (sxt, J=7.5 Hz, 2H), 0.94 (t, J=7.4 Hz, 3H).

Example 68

Synthesis of 2-(3-(4-(4-fluorophenoxy)-2-(trifluoromethyl)phenyl)propanoyl)-3,5-dihydroxy-4,6,6-tripropylcyclohexa-2,4-dienone 2-(3-(4-(4-fluorophenoxy)-2-(trifluoromethyl)phenyl)propanoyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by 3-(4-(4-fluorophenoxy)-2-(trifluoromethyl)phenyl)-1-(2,4,6-trihydroxyphenyl)propan-1-one. Yield: 17%. MS (ESI): calculated, m/z 563.2 (MH$^+$); found, 563.1. $^1$H NMR (400 MHz, d6-Acetone) δ=7.63 (br d, J=8.5 Hz, 1H), 7.28 (d, J2.8 Hz, 1H), 7.25-7.19 (m, 3H), 7.18-7.13 (m, 2H), 3.42-3.36 (m, 2H), 3.14-3.08 (m, 2H), 2.54-2.47 (m, 2H), 1.97-1.82 (m, 4H), 1.50 (qd, J=7.2, 14.9 Hz, 2H), 1.18-1.01 (m, 4H), 0.99-0.92 (m, 3H), 0.84-0.76 (m, 6H).

Example 69

Synthesis of 2-(3-(4-(4-fluorophenoxy)-2-methylphenyl)propanoyl)-3,5-dihydroxy-4,6,6-tripropylcyclohexa-2,4-dienone 2-(3-(4-(4-fluorophenoxy)-2-methylphenyl)propanoyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by 3-(4-(4-fluorophenoxy)-2-methylphenyl)-1-(2,4,6-trihydroxyphenyl)propan-1-one. Yield: 23%. MS (ESI): calculated, m/z 509.3 (MH$^+$); found, 509.1. $^1$H NMR (400 MHz, d6-Acetone) δ=7.28-7.22 (m, 1H), 7.18-7.12 (m, 2H), 7.06-6.99 (m, 2H), 6.84 (d, J=2.4 Hz, 1H), 6.77 (dd, J=2.3, 8.2 Hz, 1H), 3.35-3.28 (m, 2H), 2.99-2.86 (m, 2H), 2.55-2.46 (m, 2H), 2.35 (s, 3H), 2.01-1.83 (m, 4H), 1.54-1.44 (m, 2H), 1.17-1.00 (m, 4H), 0.98-0.91 (m, 3H), 0.85-0.77 (m, 6H).

Example 70

Synthesis of 2-(2-(4-(4-fluorophenoxy)-2-(trifluoromethyl)phenyl)cyclopropanecarbonyl)-3,5-dihydroxy-4,6,6-tripropylcyclohexa-2,4-dienone 2-(2-(4-(4-fluorophenoxy)-2-(trifluoromethyl)phenyl)cyclopropanecarbonyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by (2-(4-(4-fluorophenoxy)-2-(trifluoromethyl)phenyl)cyclopropyl)(2,4,6-trihydroxyphenyl)methanone. Yield: 23%. MS (ESI): calculated, m/z 575.2 (MH$^+$); found, 575.3. $^1$H NMR (400 MHz, d6-Acetone) δ=7.35 (br d, J=8.6 Hz, 1H), 7.18-6.99 (m, 7H), 4.09-4.01 (m, 1H), 3.51-3.42 (m, 1H), 2.84-2.76 (m, 2H), 2.36 (br t, J=7.6 Hz, 2H), 1.83-1.65 (m, 6H), 1.58-1.51 (m, 1H), 1.42-1.32 (m, 2H), 1.10-0.88 (m, 5H), 0.85-0.59 (m, 12H).

Example 71

Synthesis of 2-(2-(4-(4-fluorophenoxy)-2-methylphenyl)cyclopropanecarbonyl)-3,5-dihydroxy-4,6,6-tripropylcyclohexa-2,4-dienone 2-(2-(4-(4-fluorophenoxy)-2-methylphenyl)cyclopropanecarbonyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by (2-(4-(4-fluorophenoxy)-2-methylphenyl)cyclopropyl)(2,4,6-trihydroxyphenyl)methanone. Yield: 18%. MS (ESI): calculated, m/z 521.3 (MH$^+$); found, 521.1. $^1$H NMR (400 MHz, d6-Acetone) δ=7.23 (d, J=8.4 Hz, 1H), 7.19-7.13 (m, 2H), 7.08-7.02 (m, 2H), 6.85 (d, J=2.4 Hz, 1H), 6.78 (dd, J=2.4, 8.3 Hz, 1H), 3.99-3.90 (m, 1H), 2.69-2.58 (m, 1H), 2.54-2.44 (m, 2H), 2.31-2.24 (m, 3H), 1.96-1.79 (m, 5H), 1.61-1.47 (m, 3H), 1.21-1.03 (m, 4H), 0.99-0.92 (m, 3H), 0.85-0.76 (m, 6H).

Example 72

Synthesis of 4,6,6-triethyl-2-(2-(4-(4-fluorophenoxy)-2-(trifluoromethyl)phenyl)cyclopropanecarbonyl)-3,5-dihydroxycyclohexa-2,4-dienone 4,6,6-triethyl-2-(2-(4-(4-fluorophenoxy)-2-(trifluoromethyl)phenyl)cyclopropanecarbonyl)-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-(4-fluorophenoxy)-2-(trifluoromethyl)phenyl)cyclopropyl)(2,4,6-trihydroxyphenyl)methanone and iodoethane. Yield: 30%. MS (ESI): calculated, m/z 533.2 (MH$^+$); found, 533.1. $^1$H NMR (400 MHz, d6-Acetone) δ=7.49 (br d, J=8.5 Hz, 1H), 7.28 (d, J=2.5 Hz, 1H), 7.26-7.16 (m, 5H), 4.28-4.14 (m, 1H), 2.95 (br s, 1H), 2.63-2.51 (m, 2H), 1.97-1.67 (m, 6H), 1.13-1.02 (m, 3H), 0.77-0.65 (m, 6H).

Example 73

Synthesis of 4,6,6-triethyl-2-(3-(4-(4-fluorophenoxy)-2-(trifluoromethyl)phenyl)propanoyl)-3,5-dihydroxycyclohexa-2,4-dienone 4,6,6-triethyl-2-(3-(4-(4-fluorophenoxy)-2-(trifluoromethyl)phenyl)propanoyl)-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by 3-(4-(4-fluorophenoxy)-2-(trifluoromethyl)phenyl)-1-(2,4,6-trihydroxyphenyl)propan-1-one and iodoethane. Yield: 20%. MS (ESI): calculated, m/z 521.2 (MH$^+$); found, 521.0. $^1$H NMR (400 MHz, CDCl$_3$) δ=7.46-7.35 (m, 1H), 7.28-7.21 (m, 1H), 7.12-7.04 (m, 3H), 7.02-6.95 (m, 2H), 3.57-3.29 (m, 2H), 3.18-3.07 (m, 2H), 2.55-2.36 (m, 2H), 2.00-1.91 (m, 2H), 1.87-1.76 (m, 2H), 1.17-1.00 (m, 3H), 0.74-0.63 (m, 6H).

Example 74

Synthesis of 4,6,6-triethyl-2-(3-(4-(4-fluorophenoxy)-2-methylphenyl)propanoyl)-3,5-dihydroxycyclohexa-2,4-dienone 4,6,6-triethyl-2-(3-(4-(4-fluorophenoxy)-2-methylphenyl)propanoyl)-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by 3-(4-(4-fluorophenoxy)-2-methylphenyl)-1-(2,4,6-trihydroxyphenyl)propan-1-one and iodoethane. Yield: 23%. MS (ESI): calculated, m/z 467.2 (MH$^+$); found, 467.1. $^1$H NMR (400 MHz, d6-Acetone) δ=7.25 (br d, J=8.3 Hz, 1H), 7.18-7.11 (m, 2H), 7.05-6.99 (m, 2H), 6.83 (d, J=2.1 Hz, 1H), 6.79-6.72 (m, 1H), 3.34-3.27 (m, 1H), 2.95-2.88 (m, 2H), 2.60-2.49 (m, 2H), 2.35 (s, 3H), 2.01-1.89 (m, 4H), 1.16-1.03 (m, 3H), 0.66 (t, J=7.5 Hz, 6H).

Example 75

Synthesis of 2-(2-(4-(4-fluorophenoxy)-2-methylphenyl)cyclopropanecarbonyl)-3,5-dihydroxy-4,6,6-trimethylcyclohexa-2,4-dienone 2-(2-(4-(4-fluorophenoxy)-2-methylphenyl)cyclopropanecarbonyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-(4-fluorophenoxy)-2-methylphenyl)cyclopropyl)(2,4,6-trihydroxyphenyl)methanone and iodomethane. Yield: 44%. MS (ESI): calculated, m/z 437.2 (MH+); found, 437.1. $^1$H NMR (400 MHz, d6-Acetone) δ=7.22 (d, J=8.4 Hz, 1H), 7.19-7.13 (m, 2H), 7.08-7.02 (m, 2H), 6.84 (d, J=2.0 Hz, 1H), 6.77 (dd, J=2.2, 8.3 Hz, 1H), 3.84 (br d, J=3.6 Hz, 1H), 2.63 (br s, 1H), 2.30 (s, 3H), 1.96-1.86 (m, 3H), 1.84-1.78 (m, 1H), 1.54 (br s, 1H), 1.39 (s, 6H).

Example 76

Synthesis of 2-(2-(4-chloro-2-(trifluoromethyl)phenyl)cyclopropanecarbonyl)-3,5-dihydroxy-4,6,6-trimethylcyclohexa-2,4-dienone 2-(2-(4-chloro-2-(trifluoromethyl)phenyl)cyclopropanecarbonyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-chloro-2-(trifluoromethyl)phenyl)cyclopropyl)(2,4,6-trihydroxyphenyl)methanone and iodomethane. Yield: 18%. MS (ESI): calculated, m/z 415.1 (MH+); found, 414.9. $^1$H NMR (400 MHz, d6-Acetone) δ=7.75-7.65 (m, 2H), 7.52 (br d, J=8.3 Hz, 1H), 4.16-4.08 (m, 1H), 2.93 (br s, 1H), 1.94-1.80 (m, 4H), 1.72-1.65 (m, 1H), 1.39 (d, J=11.4 Hz, 6H).

Example 77

Synthesis of 2-(2-(4-chloro-2-methylphenyl)cyclopropanecarbonyl)-3,5-dihydroxy-4,6,6-trimethylcyclohexa-2,4-dienone 2-(2-(4-chloro-2-methylphenyl)cyclopropanecarbonyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-chloro-2-methylphenyl)cyclopropyl)(2,4,6-trihydroxyphenyl)methanone and iodomethane. Yield: 18%. MS (ESI): calculated, m/z 361.1 (MH+); found, 360.7. $^1$H NMR (400 MHz, d6-Acetone) δ=7.27-7.17 (m, 3H), 3.94-3.81 (m, 1H), 2.71-2.57 (m, 1H), 2.38-2.28 (m, 3H), 1.90 (s, 3H), 1.85-1.79 (m, 1H), 1.55-1.51 (m, 1H), 1.40 (s, 6H).

Example 78

Synthesis of 2-(3-(4-(4-fluorophenoxy)phenyl)propanoyl)-3,5-dihydroxy-4,6,6-trimethylcyclohexa-2,4-dienone 2-(3-(4-(4-fluorophenoxy)phenyl)propanoyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by 3-(4-(4-fluorophenoxy)phenyl)-1-(2,4,6-trihydroxyphenyl)propan-1-one and iodomethane. Yield: 40%. MS (ESI): calculated, m/z 411.2 (MH+); found, 411.0. $^1$H NMR (400 MHz, d6-Acetone) δ=7.32 (d, J=8.4 Hz, 2H), 7.19-7.11 (m, 2H), 7.08-7.00 (m, 2H), 6.94 (d, J=8.5 Hz, 2H), 3.30 (br t, J=7.7 Hz, 2H), 2.92 (br t, J=7.8 Hz, 2H), 1.90 (s, 3H), 1.38 (s, 6H).

Example 79

Synthesis of 2-(2-(4-chlorophenyl)cyclopropanecarbonyl)-3,5-dihydroxy-4,6,6-tripropylcyclohexa-2,4-dienone 2-(2-(4-chlorophenyl)cyclopropanecarbonyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by (2-(4-chlorophenyl)cyclopropyl)(2,4,6-trihydroxyphenyl)methanone. Yield: 21%. MS (ESI): calculated, m/z 431.2 (MH+); found, 431.0. $^1$H NMR (400 MHz, d6-Acetone) δ=7.23-7.18 (m, 2H), 7.17-7.11 (m, 2H), 4.11-3.93 (m, 1H), 2.66-2.50 (m, 1H), 2.42-2.29 (m, 2H), 1.81-1.63 (m, 5H), 1.45-1.29 (m, 3H), 1.05-0.91 (m, 4H), 0.80 (t, J=7.3 Hz, 3H), 0.70-0.65 (m, 3H), 0.63-0.55 (m, 3H).

Example 80

Synthesis of 2-(2-(4-chloro-2-(trifluoromethyl)phenyl)cyclopropanecarbonyl)-3,5-dihydroxy-4,6,6-tripropylcyclohexa-2,4-dienone 2-(2-(4-chloro-2-(trifluoromethyl)phenyl)cyclopropanecarbonyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by (2-(4-chloro-2-(trifluoromethyl)phenyl)cyclopropyl)(2,4,6-trihydroxyphenyl)methanone. Yield: 22%. MS (ESI): calculated, m/z 499.2 (MH+); found, 499.1. $^1$H NMR (400 MHz, d6-Acetone) δ=7.75-7.65 (m, 2H), 7.52 (br d, J=8.3 Hz, 1H), 4.27-4.17 (m, 1H), 2.94 (br s, 1H), 2.56-2.47 (m, 2H), 1.98-1.82 (m, 5H), 1.75-1.68 (m, 1H), 1.51 (qd, J=7.4, 15.1 Hz, 2H), 1.19-1.03 (m, 4H), 0.95 (t, J=7.3 Hz, 3H), 0.79 (td, J=7.3, 19.8 Hz, 6H).

Example 81

Synthesis of 2-(2-(4-chlorophenyl)cyclopropanecarbonyl)-4,6,6-triethyl-3,5-dihydroxycyclohexa-2,4-dienone 2-(2-(4-chlorophenyl)cyclopropanecarbonyl)-4,6,6-triethyl-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-chlorophenyl)cyclopropyl)(2,4,6-trihydroxyphenyl)methanone and iodoethane. Yield: 35%. MS (ESI): calculated, m/z 389.1 (MH+); found, 389.0. $^1$H NMR (400 MHz, d6-Acetone) δ=7.38-7.33 (m, 2H), 7.32-7.27 (m, 2H), 4.23-4.15 (m, 1H), 2.76-2.69 (m, 1H), 2.62-2.50 (m, 2H), 1.99-1.82 (m, 5H), 1.55 (ddd, J=3.9, 6.5, 8.2 Hz, 1H), 1.10-1.00 (m, 3H), 0.71 (t, J=7.5 Hz, 3H), 0.63 (t, J=7.5 Hz, 3H).

Example 82

Synthesis of 2-(2-(4-chloro-2-methylphenyl)cyclopropanecarbonyl)-4,6,6-triethyl-3,5-dihydroxycyclohexa-2,4-dienone 2-(2-(4-chloro-2-methylphenyl)cyclopropanecarbonyl)-4,6,6-triethyl-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-chloro-2-methylphenyl)cyclopropyl)(2,4,6-trihydroxyphenyl)methanone and iodoethane. Yield: 24%. MS (ESI): calculated, m/z 403.2 (MH$^+$); found, 403.1. $^1$H NMR (400 MHz, d6-Acetone) δ=7.26-7.18 (m, 3H), 3.99-3.92 (m, 1H), 2.67-2.62 (m, 1H), 2.61-2.53 (m, 2H), 2.33 (s, 3H), 2.00-1.84 (m, 5H), 1.61-1.54 (m, 1H), 1.08 (t, J=7.4 Hz, 3H), 0.74-0.68 (m, 6H).

Example 83

Synthesis of 2-(2-(2,4-bis(trifluoromethyl)phenyl)cyclopropanecarbonyl)-3,5-dihydroxy-4,6,6-trimethylcyclohexa-2,4-dienone 2-(2-(2,4-bis(trifluoromethyl)phenyl)cyclopropanecarbonyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(2,4-bis(trifluoromethyl)phenyl)cyclopropyl)(2,4,6-trihydroxyphenyl)methanone and iodomethane. Yield: 23%. MS (ESI): calculated, m/z 449.1 (MH$^+$); found, 448.9. $^1$H NMR (400 MHz, d6-Acetone) δ=8.09-7.93 (m, 2H), 7.72 (br d, J=8.2 Hz, 1H), 4.30-4.08 (m, 1H), 3.02 (br s, 1H), 1.98-1.84 (m, 4H), 1.81-1.73 (m, 1H), 1.50-1.31 (m, 6H).

Example 84

Synthesis of 2-(2-(4-chloro-2-(trifluoromethyl)phenyl)cyclopropanecarbonyl)-4,6,6-triethyl-3,5-dihydroxycyclohexa-2,4-dienone 2-(2-(4-chloro-2-(trifluoromethyl)phenyl)cyclopropanecarbonyl)-4,6,6-triethyl-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-chloro-2-(trifluoromethyl)phenyl)cyclopropyl)(2,4,6-trihydroxyphenyl)methanone and iodoethane. Yield: 41%. MS (ESI): calculated, m/z 457.1 (MH$^+$); found, 457.0. $^1$H NMR (400 MHz, d6-Acetone) δ=7.60-7.46 (m, 2H), 7.37 (br d, J=8.4 Hz, 1H), 4.07 (br s, 1H), 2.79 (br s, 1H), 2.41 (q, J=7.0 Hz, 2H), 1.87-1.68 (m, 5H), 1.57 (br s, 1H), 0.92 (br t, J=7.0 Hz, 3H), 0.59-0.47 (m, 6H).

Example 85

Synthesis of 2-(2-(4-(4-fluorophenoxy)-2-(trifluoromethyl)phenyl)cyclopropanecarbonyl)-3,5-dihydroxy-4,6,6-trimethylcyclohexa-2,4-dienone 2-(2-(4-(4-fluorophenoxy)-2-(trifluoromethyl)phenyl)cyclopropanecarbonyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-(4-fluorophenoxy)-2-(trifluoromethyl)phenyl)cyclopropyl)(2,4,6-trihydroxyphenyl)methanone and iodomethane. Yield: 23%. MS (ESI): calculated, m/z 491.1 (MH$^+$); found, 491.1. $^1$H NMR (400 MHz, d6-Acetone) δ=7.48 (br d, J=8.7 Hz, 1H), 7.28 (d, J=2.6 Hz, 1H), 7.25-7.21 (m, 2H), 7.21-7.19 (m, 1H), 7.19-7.15 (m, 2H), 4.13-4.06 (m, 1H), 2.93 (br s, 1H), 1.90 (s, 3H), 1.83 (td, J=4.6, 9.0 Hz, 1H), 1.70-1.62 (m, 1H), 1.39 (br d, J=9.4 Hz, 6H).

Example 86

Synthesis of 2-(2-(2,4-bis(trifluoromethyl)phenyl)cyclopropanecarbonyl)-3,5-dihydroxy-4,6,6-tripropylcyclohexa-2,4-dienone 2-(2-(2,4-bis(trifluoromethyl)phenyl)cyclopropanecarbonyl)-3,5-dihydroxy-4,6,6-tripropylcyclohexa-2,4-dienone was synthesized as described in Example 59, but [2-(4-phenoxyphenyl)cyclopropyl]-(2,4,6-trihydroxyphenyl)methanone was replaced by (2-(2,4-bis(trifluoromethyl)phenyl)cyclopropyl)(2,4,6-trihydroxyphenyl)methanone. Yield: 38%. MS (ESI): calculated, m/z 533.2 (MH$^+$); found, 533.2. $^1$H NMR (400 MHz, d6-Acetone) δ=7.95-7.72 (m, 2H), 7.58 (d, J=8.2 Hz, 1H), 4.15 (br d, J=3.5 Hz, 1H), 2.87 (br s, 1H), 2.36 (br t, J=7.5 Hz, 2H), 1.86-1.54 (m, 6H), 1.42-1.28 (m, 2H), 1.08-0.85 (m, 4H), 0.80 (br t, J=7.2 Hz, 3H), 0.72-0.56 (m, 6H).

Example 87

Synthesis of 2-(2-(2,4-bis(trifluoromethyl)phenyl)cyclopropanecarbonyl)-4,6,6-triethyl-3,5-dihydroxycyclohexa-2,4-dienone 2-(2-(2,4-bis(trifluoromethyl)phenyl)cyclopropanecarbonyl)-4,6,6-triethyl-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(2,4-bis(trifluoromethyl)phenyl)cyclopropyl)(2,4,6-trihydroxyphenyl)methanone and iodoethane. Yield: 29%. MS (ESI): calculated, m/z 491.2 (MH$^+$); found, 491.1. $^1$H NMR (400 MHz, d6-Acetone) δ=8.08-7.93 (m, 2H), 7.74 (br d, J=8.3 Hz, 1H), 4.38-4.23 (m, 1H), 3.04 (br s, 1H), 2.66-2.42 (m, 2H), 2.01-1.74 (m, 6H), 1.17-0.96 (m, 3H), 0.80-0.61 (m, 6H).

Example 88

Synthesis of 3,5-dihydroxy-4,6,6-trimethyl-2-(2-(4-(trifluoromethyl)phenyl)cyclopropanecarbonyl)cyclohexa-2,4-dienone 3,5-dihydroxy-4,6,6-trimethyl-2-(2-(4-(trifluoromethyl)phenyl)cyclopropanecarbonyl)cyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-(trifluoromethyl)phenyl)cyclopropyl)(2,4,6-trihydroxyphenyl)methanone and iodomethane. Yield: 30%. MS (ESI): calculated, m/z 381.1 (MH$^+$); found, 381.8. $^1$H NMR (400 MHz, d6-Acetone) δ=7.67 (br d, J=8.2 Hz, 2H), 7.49 (br d, J=8.2 Hz, 2H), 4.19-4.10 (m, 1H), 2.83-2.75 (m, 1H), 1.92-1.87 (m, 3H), 1.60 (br d, J=3.1 Hz, 1H), 1.51-1.44 (m, 1H), 1.42-1.38 (m, 3H), 1.35 (s, 3H).

Example 89

Synthesis of 2-(2-(4-chlorophenyl)cyclopropanecarbonyl)-4,6,6-triethyl-3,5-dihydroxycyclohexa-2,4-dienone 2-(2-(4-chlorophenyl)cyclopropanecarbonyl)-4,6,6-triethyl-3,5-dihydroxycyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-chlorophenyl)cyclopropyl)(2,4,6-trihydroxyphenyl)methanone and iodoethane. Yield: 35%. MS (ESI): calculated, m/z 389.1 (MH$^+$); found, 389.0. $^1$H NMR (400 MHz, d6-Acetone) δ=7.38-7.32 (m, 2H), 7.32-7.26 (m, 2H), 4.22-4.13 (m, 1H), 2.76-2.68 (m, 1H), 2.55 (q, J=7.4 Hz, 2H), 2.01-1.82 (m, 5H), 1.55 (ddd, J=3.9, 6.5, 8.2 Hz, 1H), 1.12-1.02 (m, 3H), 0.71 (t, J7.5 Hz, 3H), 0.63 (t, J=7.5 Hz, 3H).

Example 90

Synthesis of 4,6,6-triethyl-3,5-dihydroxy-2-(2-(4-(trifluoromethyl)phenyl)cyclopropanecarbonyl)cyclohexa-2,4-dienone 4,6,6-triethyl-3,5-dihydroxy-2-(2-(4-(trifluoromethyl)phenyl)cyclopropanecarbonyl)cyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-(trifluoromethyl)phenyl)cyclopropyl)(2,4,6-trihydroxyphenyl)methanone and iodoethane. Yield: 40%. MS (ESI): calculated, m/z 422.2 (MH$^+$); found, 422.9. $^1$H NMR (400 MHz, d6-Acetone) δ=7.67 (d, J=8.2 Hz, 2H), 7.50 (d, J=8.0 Hz, 2H), 4.35-4.20 (m, 1H), 2.90-2.77 (m, 1H), 2.62-2.48 (m, 2H), 1.99-1.85 (m, 5H), 1.69-1.58 (m, 1H), 1.17-1.00 (m, 3H), 0.72 (t, J=7.4 Hz, 3H), 0.62 (t, J=7.4 Hz, 3H).

Example 91

Synthesis of 3,5-dihydroxy-4,6,6-tripropyl-2-(2-(4-(trifluoromethyl)phenyl)cyclopropanecarbonyl)cyclohexa-2,4-dienone 3,5-dihydroxy-4,6,6-tripropyl-2-(2-(4-(trifluoromethyl)phenyl)cyclopropanecarbonyl)cyclohexa-2,4-dienone was synthesized as described in Example 59, but [2-(4-phenoxyphenyl-)cyclopropyl]-(2,4,6-trihydroxyphenyl)methanone was replaced by (2-(4-(trifluoromethyl)phenyl)cyclopropyl)(2,4,6-trihydroxyphenyl)methanone. Yield: 40%. MS (ESI): calculated, m/z 465.2 (MH$^+$); found, 465.2. $^1$H NMR (400 MHz, d6-Acetone) δ=7.67 (d, J=8.2 Hz, 2H), 7.49 (d, J=8.2 Hz, 2H), 4.31-4.15 (m, 1H), 2.85-2.75 (m, 1H), 2.59-2.43 (m, 2H), 1.96-1.76 (m, 5H), 1.62 (ddd, J=4.0, 6.5, 8.4 Hz, 1H), 1.55-1.46 (m, 2H), 1.23-0.99 (m, 4H), 0.95 (t, J=7.4 Hz, 3H), 0.85-0.80 (m, 3H), 0.73 (t, J=7.3 Hz, 3H).

Example 92

Synthesis of 2-(2-(4-(4-fluorophenoxy)phenyl)cyclopropanecarbonyl)-3,5-dihydroxy-4,6,6-trimethylcyclohexa-2,4-dienone 2-(2-(4-(4-fluorophenoxy)phenyl)cyclopropanecarbonyl)-3,5-dihydroxy-4,6,6-trimethylcyclohexa-2,4-dienone was synthesized as described in Example 59, but [2-(4-phenoxyphenyl)cyclopropyl]-(2,4,6-trihydroxyphenyl)methanone and 1-iodopropane were replaced by (2-(4-(4-fluorophenoxy)phenyl)cyclopropyl)(2,4,6-trihydroxyphenyl)methanone and iodomethane. Yield: 40%. MS (ESI): calculated, m/z 445.2 (M+Na$^+$); found, 445.0. $^1$H NMR (400 MHz, d6-Acetone) δ=7.27 (br d, J=8.5 Hz, 2H), 7.19-7.15 (m, 2H), 7.09-7.04 (m, 2H), 6.98-6.92 (m, 2H), 4.13-3.98 (m, 1H), 2.71 (br s, 1H), 1.92-1.80 (m, 3H), 1.60 (br d, J=5.3 Hz, 1H), 1.51 (br s, 1H), 1.43-1.29 (m, 6H).

Example 93

Assay of Inhibition of Bacterial RNA Polymerase

Example 93.1

Assay of Inhibition of *Escherichia Coli* RNA Polymerase

Fluorescence-detected RNA polymerase assays with *E. coli* RNA polymerase were performed by a modification of the procedure of Kuhlman et al., 2004 [Kuhlman, P., Duff, H. & Galant, A. (2004) A fluorescence-based assay for multisubunit DNA-dependent RNA polymerases. *Anal. Biochem.* 324, 183-190]. Reaction mixtures contained (20 µl): 0-100 nM test compound, 75 nM *E. coli* RNA polymerase σ$^{70}$ holoenzyme, 20 nM 384 bp DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM MgCl$_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM CaCl$_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC50 is defined as the concentration of inhibitor resulting in 50% inhibition of RNA polymerase activity.

Example 93.2

Assay of Inhibition of *Staphylococcus Aureus* RNA Polymerase

Fluorescence-detected RNA polymerase assays with *S. aureus* RNA polymerase were performed as in Example 93.1, using reaction mixtures containing (20 µl): 0-100 nM test compound, 75 nM *S. aureus* RNA polymerase core enzyme, 300 nM *S. aureus* σ$^A$, 20 nM 384 bp DNA fragment containing the bacteriophage T4 N25 promoter, 100 µM ATP, 100 µM GTP, 100 µM UTP, 100 µM CTP, 40 mM Tris-HCl, pH 8.0, 80 mM NaCl, 5 mM MgCl$_2$, 2.5 mM DTT, and 12.7% glycerol. IC50 is defined as the concentration of inhibitor resulting in 50% inhibition of RNA polymerase activity.

Data for representative compounds are shown in Table 2.

TABLE 2

Inhibition of bacterial RNAP.

| Example | IC50 E. coli RNAP (nM) | IC50 S. aureus RNAP (nM) |
|---|---|---|
| 1 | 0.72 | 5.7 |
| 2 | 2.3 | 6.1 |
| 3 | 1.4 | 3.1 |
| 4 | 1.2 | 1.8 |
| 5 | 2.4 | 2.3 |
| 6 | 12 | 43 |
| 7 | 2.6 | 2.6 |
| 8 | 11 | 12 |
| 9 | 11 | 1.7 |
| 10 | 1.9 | 1.7 |
| 11 | 19 | 26 |
| 12 | 2.5 | 2.4 |
| 13 | 2.5 | 2.8 |
| 14 | 3.9 | 7.1 |
| 15 | 2.6 | 3 |
| 16 | 1.4 | 1.5 |
| 17 | 1.0 | 1.3 |
| 18 | 0.61 | 1.5 |
| 19 | 2.8 | 1.9 |
| 20 | 0.74 | 0.64 |
| 21 | 1.3 | 1.5 |
| 22 | 0.35 | 0.41 |
| 23 | 0.81 | 1.2 |
| 24 | 0.99 | 1.3 |
| 25 | 0.27 | 0.69 |
| 26 | 0.67 | 0.79 |
| 27 | 4.3 | 13 |
| 28 | 1.3 | 2.8 |
| 29 | 0.53 | 2.6 |
| 30 | 0.17 | 5.2 |
| 31 | 2.2 | 6 |
| 32 | 1.5 | 3.8 |
| 33 | 1.7 | 1.6 |
| 34 | 0.72 | 1.8 |
| 35 | 2.7 | 3.4 |
| 36 | 0.53 | 3.2 |
| 37 | 1.7 | 4.4 |
| 38 | 3.8 | 3.6 |
| 39 | 0.73 | 3.5 |
| 40 | 3.9 | 13 |
| 41 | 1.9 | 5.1 |
| 42 | 0.38 | 2.3 |
| 43 | 1.0 | 4.9 |
| 44 | 0.076 | 1.2 |
| 45 | 0.11 | 0.7 |
| 46 | 0.18 | 1.1 |
| 47 | 0.4 | 1.0 |
| 48 | 1.6 | 3.8 |
| 49 | 0.048 | 0.34 |
| 50 | 0.15 | 0.35 |
| 51 | 0.042 | 0.59 |
| 52 | 0.039 | 0.19 |
| 53 | 1.2 | 1.7 |
| 54 | 0.67 | 2.3 |
| 55 | 1.0 | 2.4 |
| 56 | 0.90 | 3.4 |
| 57 | 0.60 | 3.6 |
| 58 | 0.41 | 3.5 |
| 59 | 0.66 | 2.3 |
| 60 | 3.2 | 10 |
| 61 | 1.0 | 3.0 |
| 62 | 0.87 | 2.5 |
| 63 | 6.5 | >200 |
| 64 | 0.65 | 6.5 |
| 65 | >200 | >200 |

TABLE 2-continued

Inhibition of bacterial RNAP.

| Example | IC50 E. coli RNAP (nM) | IC50 S. aureus RNAP (nM) |
|---|---|---|
| 66 | 0.14 | 1.3 |
| 67 | 12 | >200 |
| 68 | 0.019 | 0.63 |
| 69 | 0.22 | 3.1 |
| 70 | 0.11 | 2.2 |
| 71 | 0.13 | 2.4 |
| 72 | 0.57 | 14 |
| 73 | 2.4 | >22 |
| 74 | 2.2 | 12 |
| 75 | 0.65 | 11 |
| 76 | >25 | >20 |
| 77 | >25 | 8.3 |
| 78 | 2.1 | 18 |
| 79 | 3.3 | 11 |
| 80 | 0.58 | 1.4 |
| 81 | >50 | 12 |
| 82 | 1.6 | 1.3 |
| 83 | >50 | 19 |
| 84 | 15 | 2.8 |
| 85 | 7.5 | >30 |
| 86 | 8.4 | 8.3 |
| 87 | 6.1 | 21 |
| 88 | 11 | >40 |
| 89 | 2.1 | 36 |
| 90 | 4.2 | >40 |
| 91 | 0.85 | 23 |
| 92 | 3.1 | >40 |

Example 94

Assay of Inhibition of Bacterial Growth in Culture

Minimum inhibitory concentrations (MICs) for *Staphylococcus aureus* ATCC 12600, *Enterococcus faecalis* ATCC 19433, and *Escherichia coli* D21f2tolC were quantified using spiral gradient endpoint assays, essentially as described [Wallace, A. and Corkill, J. (1989) Application of the spiral plating method to study antimicrobial action. *J. Microbiol. Meths.* 10, 303-310; Paton, J., Holt, A., and Bywater, M. (1990) Measurement of MICs of antibacterial agents by spiral gradient endpoint compared with conventional dilution methods. *Int. J. Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-100 μg/ml of test compound. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-compound concentration at the streak endpoint was calculated using the program SGE (Spiral Biotech, Inc.), and the MIC was defined as the calculated test-compound concentration at the streak endpoint.

Data for representative compounds are shown in Table 3.

TABLE 3

Inhibition of bacterial growth.

| Example | MIC S. aureus 12600 (µg/ml) | MIC E. faecalis H37Rv (µg/ml) | MIC E. coli D21f2tolC (µg/ml) |
|---|---|---|---|
| 1 | 32 | >40 | 24 |
| 2 | 12 | 12 | 9.3 |
| 3 | 1.9 | 3.7 | 1.9 |
| 4 | 2.4 | 3.2 | 1.5 |
| 5 | 2.6 | 6.0 | 1.6 |
| 6 | >40 | >40 | >40 |
| 7 | >40 | >40 | 16 |
| 8 | 6.5 | 31 | 3.8 |
| 9 | 13 | 16 | 8 |
| 10 | 3.1 | 5.1 | 1.5 |
| 11 | 17 | >40 | 5.9 |
| 12 | 3.1 | 4.0 | 1.5 |
| 13 | 4.3 | 4.8 | 2.1 |
| 14 | 32 | 32 | 20 |
| 15 | 3.2 | 3.6 | 1.8 |
| 16 | 1.1 | 1.8 | 1.3 |
| 17 | 1.8 | 1.9 | 2.5 |
| 18 | 1.3 | 2.4 | 1.1 |
| 19 | 20 | >40 | 13 |
| 20 | 2.1 | 2.4 | 1.7 |
| 21 | 16 | >40 | 20 |
| 22 | 1.0 | 1.3 | 0.49 |
| 23 | 1.1 | 1.7 | 1.7 |
| 24 | 1.8 | 3.0 | 1.1 |
| 25 | 1.7 | 1.7 | 1.5 |
| 26 | 1.4 | 2.1 | 1.4 |
| 27 | 5.1 | 17 | 2.4 |
| 28 | 3.1 | 6.5 | 2.4 |
| 29 | 1.5 | 2.4 | 1.5 |
| 30 | 14 | 17 | 6.5 |
| 31 | 5.8 | 9.6 | 1.4 |
| 32 | 3.5 | 5.7 | 2.1 |
| 33 | 4.6 | 7.5 | 1.6 |
| 34 | 3.6 | 5.2 | 1.1 |
| 35 | 3.5 | 5.1 | 1.3 |
| 36 | 2.4 | 4.4 | 1.7 |
| 37 | 3.5 | 4.4 | 2.4 |
| 38 | >40 | >40 | >40 |
| 39 | 3.6 | 4.1 | 1.6 |
| 40 | >40 | >40 | 9.4 |
| 41 | 19 | 19 | 9.4 |
| 42 | 14 | 16 | 10 |
| 43 | 6.6 | 8.4 | 2.8 |
| 44 | 1.5 | 1.8 | 1.5 |
| 45 | 9.6 | 11 | 5.2 |
| 46 | 9.6 | 12 | 6.6 |
| 47 | 9.6 | 9.6 | 4.8 |
| 48 | >40 | >40 | 20 |
| 49 | 12 | 12 | 12 |
| 50 | 16 | 18 | 19 |
| 51 | 11 | 15 | 16 |
| 52 | 3.2 | 5.2 | 7.5 |
| 53 | 4.7 | 5.3 | 4.7 |
| 54 | 12 | 17 | 17 |
| 55 | 17 | 22 | >40 |
| 56 | 17 | 22 | >40 |
| 57 | 4.3 | 5.7 | 3.5 |
| 58 | 10 | 12 | 3.9 |
| 59 | 0.7 | 3.0 | 1.1 |
| 60 | 10 | >40 | 3.9 |
| 61 | 0.56 | 0.44 | 0.24 |
| 62 | 0.40 | 0.51 | 0.28 |
| 63 | 5.1 | >40 | 2.4 |
| 64 | 0.26 | 0.34 | 0.34 |
| 65 | 1.9 | 1.9 | >40 |
| 66 | 0.16 | 0.55 | 0.72 |
| 67 |  | 0.55 | 0.72 |
| 68 | 0.6 | 1.3 | 1.5 |
| 69 | 1.1 | 1.4 | 1.1 |
| 70 | 1.5 | 1.2 | 8.2 |
| 71 | 0.9 | 2.1 | 2.3 |
| 72 | 6.5 | >40 | 1.6 |
| 73 | 1.5 | 1.6 | 1.2 |
| 74 | 1.7 | 11 | 0.9 |
| 75 | 17 | >40 | 5.1 |
| 76 | 12 | >40 | 3.1 |
| 77 | >40 | >40 | 7.4 |
| 78 | >40 | >40 | 6.5 |
| 79 | 0.27 | 0.61 | 0.15 |
| 80 | 0.14 | 0.42 | 0.33 |
| 81 | 4.5 | 11 | 2.2 |
| 82 | 3.6 | 12 | 1.2 |
| 83 | 5 | >40 | 2.4 |
| 84 | 1.3 | 2.1 | 0.44 |
| 85 | 12 | >40 | 4.0 |
| 86 | 0.65 | 1.7 | 2.2 |
| 87 | 5.9 | >40 | 3.2 |
| 88 | >40 | >40 | >40 |
| 89 | 7.9 | >40 | 3.0 |
| 90 | 1.4 | 2.3 | 1.1 |
| 91 | 0.36 | 0.41 | 0.66 |
| 92 | 21 | >40 | 5.5 |

The data in Table 2 show that certain compounds according to general structural formulae (I)-(VI) potently inhibit bacterial RNA polymerases.

The data in Table 3 show that certain compounds according to general structural formulae (I)-(VI) potently inhibit strains of the Gram-positive bacteria *Staphylococcus aureus* and *Enterococcus faecalis* and the Gram-negative bacterium *Escherichia coli*.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound selected from compounds of structural formulae (I)-(VI):

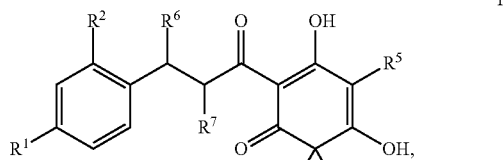

I

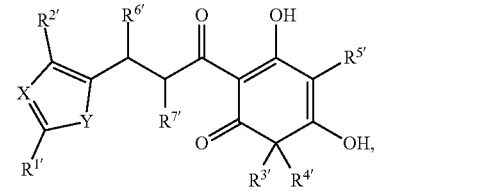

II

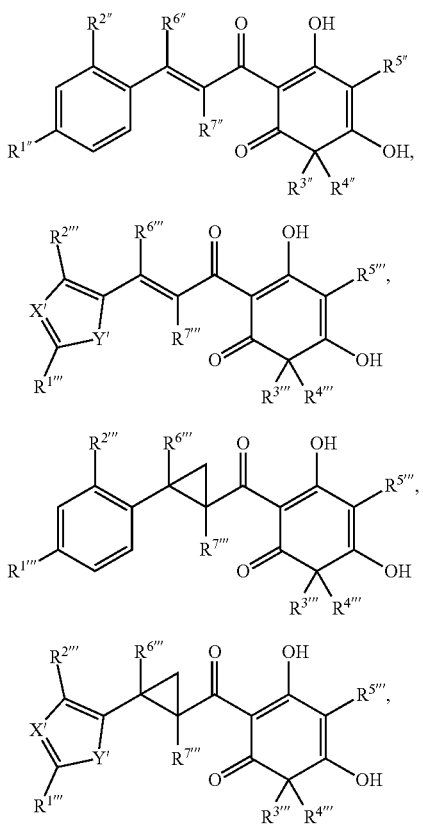

and tautomers and salts thereof, wherein:

$R^2$, $R^6$, and $R^7$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^1$ is fluoromethyl, difluoromethyl, fluoroethyl, difluoroethyl, trifluoroethyl, fluoropropyl, difluoropropyl, trifluoropropyl, fluoromethoxy, difluoromethoxy, fluoroethoxy, difluoroethoxy, trifluoroethoxy, fluoropropoxy, difluoropropoxy, trifluoropropoxy, alkaryl, alkheteroaryl, aryloxy, heteroaryloxy, or benzyloxy, which alkaryl, alkheteroaryl, aryloxy, heteroarlyoxy, or benzyloxy is substituted by one or more of halo, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^3$, $R^4$, and $R^5$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, —$NR^aR^b$, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, $(C_1-C_7)C(=O)NH$—, aryl, heteroaryl, aryloxy, and heteroaryloxy; $R^a$ and $R^b$ each independently is H or $(C_1-C_6)$alkyl, or $R^a$ and $R^b$, together with the nitrogen to which they are attached, form a morpholino, piperazino, pyrrolidino, or piperidino; and at least one of $R^3$, $R^4$, and $R^5$ is other than H; or $R^1$ is $(C_2-C_8)$alkenyl, alkaryl, alkheteroaryl, aryloxy, heteroaryloxy, or benzyloxy, which $(C_2-C_8)$alkenyl, alkaryl, alkheteroaryl, aryloxy, heteroarlyoxy, or benzyloxy optionally is substituted by one or more of halo, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, or heteroaryloxy; and $R^3$, $R^4$, and $R^5$ each is H;

X and Y are individually carbon, sulfur, oxygen, or nitrogen, wherein at least one of X and Y is other than carbon;

$R^{2'}$, $R^{6'}$, and $R^{7'}$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^{1'}$ is halo, $(C_1-C_8)$alkyl, $(C_2-C_8)$alkenyl, $(C_1-C_8)$alkoxy, aryl, heteroaryl, alkaryl, alkheteroaryl, aryloxy, heteroarloxy, or benzyloxy, which $(C_1-C_8)$alkyl, $(C_2-C_8)$alkenyl, $(C_1-C_8)$alkoxy, aryl, heteroaryl, alkaryl, alkheteroaryl, aryloxy, heteroaryloxy, or benzyloxy optionally is substituted with one or more of halo, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy;

$R^{3'}$, $R^{4'}$, and $R^{5'}$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, —$NR^{a'}R^{b'}$, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxyl, $(C_1-C_7)C(=O)NH$—, aryl, heteroaryl, aryloxy, and heteroaryloxy; and $R^{a'}$ and $R^{b'}$ each independently is H or $(C_1-C_6)$alkyl, or $R^{a'}$ and $R^{b'}$, together with the nitrogen to which they are attached, form a morpholino, piperazino, pyrrolidino, or piperidino;

$R^{2''}$, $R^{6''}$, and $R^{7''}$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^{1''}$ is $(C_2-C_8)$alkyl, $(C_2-C_8)$alkenyl, $(C_2-C_8)$alkoxy, aryl, heteroaryl, alkaryl, alkheteroaryl, aryloxy, heteroaryloxy, or benzyloxy, which $(C_2-C_8)$alkyl, $(C_2-C_8)$alkenyl, $(C_2-C_8)$alkoxy, aryl, heteroaryl, alkaryl, alkheteroaryl, aryloxy, heteroaryloxy, or benzyloxy optionally is substituted with one or more of halo, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^{3''}$, $R^{4''}$, and $R^{5''}$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, —$NR^{a''}R^{b''}$, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, $(C_1-C_7)C(=O)NH$—, aryl, heteroaryl, aryloxy, and heteroaryloxy; $R^{a''}$ and $R^{b''}$ each independently is H or $(C_1-C_6)$alkyl, or $R^{a''}$ and $R^{b''}$, together with the nitrogen to which they are attached, form a morpholino, piperazino, pyrrolidino, or piperidino, and at least one of $R^{3''}$, $R^{4''}$, and $R^{5''}$ is other than H; or $R^{1''}$ is fluoromethyl, difluoromethyl, trifluromethyl, fluoroethyl, difluoroethyl, trifluoroethyl, fluoropropyl, difluoropropyl, trifluoropropyl, fluoromethoxy, difluoromethoxy, trifluoromethoxy, fluoroethoxy, difluoroethoxy, trifluoroethoxy, fluoropropoxy, difluoropropoxy, trifluoropropoxy, aryloxy, heteroaryloxy, alkaryl, or alkheteroaryl, which aryloxy, heteroarlyoxy, alkaryl, alkheteroaryl optionally is substituted by one or more of halo, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^{3''}$, $R^{4''}$, and $R^{5''}$ each is H;

X' and Y' are individually carbon, sulfur, oxygen, or nitrogen, wherein at least one of X and Y is other than carbon;

$R^{2'''}$, $R^{6'''}$, and $R^{7'''}$ each independently is H, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

$R^{1'''}$ is halo, $(C_1-C_8)$alkyl, $(C_2-C_8)$alkenyl, $(C_1-C_8)$alkoxy, aryl, heteroaryl, alkaryl, alkheteroaryl, aryloxy, heteroaryloxy, or benzyloxy, which $(C_1-C_8)$alkyl, $(C_2-C_8)$alkenyl, $(C_1-C_8)$alkoxy, aryl, heteroaryl, alkaryl, alkheteroaryl, aryloxy, heteroaryloxy, or benzyloxy optionally is substituted with one or more of halo, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, and heteroaryloxy; and $R^{3'''}$, $R^{4'''}$, and $R^{5'''}$ each independently is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, carboxy, cyano, —$NR^{a'''}R^{b'''}$, fluoromethyl, difluoromethyl, trifluromethyl, fluoromethoxy, difluoromethoxy, trifluoromethoxy, $(C_1-C_8)$alkyl, $(C_2-C_8)$alkenyl, $(C_1-C_8)$alkoxy, $(C_1-C_7)C(=O)NH$—, aryl, heteroaryl, aryloxy, or heteroaryloxy, and $R^{a'''}$ and $R^{b'''}$ each independently is H or $(C_1-C_6)$alkyl, or $R^{a''}$ and $R^{b''}$, together with the nitrogen to which they are attached, form a morpholino, piperazino, pyrrolidino, or piperidino.

2. The compound tautomer or salt of claim 1 which is a compound of formula I or a tautomer or salt thereof.

3. The compound tautomer or salt of claim 1 which is a compound of formula II or a tautomer or salt thereof.

4. The compound tautomer or salt of claim 1 which is a compound of formula III or a tautomer or salt thereof.

5. The compound tautomer or salt of claim 1 which is a compound of formula IV or a tautomer or salt thereof.

6. The compound tautomer or salt of claim 1 which is a compound of formula V or a tautomer or salt thereof.

7. The compound tautomer or salt of claim 1 which is a compound of formula VI or a tautomer or salt thereof.

8. The compound

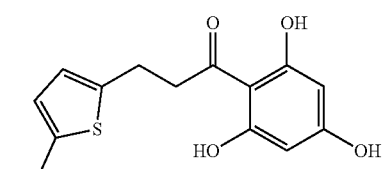

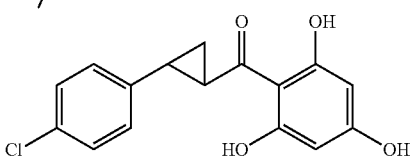

-continued

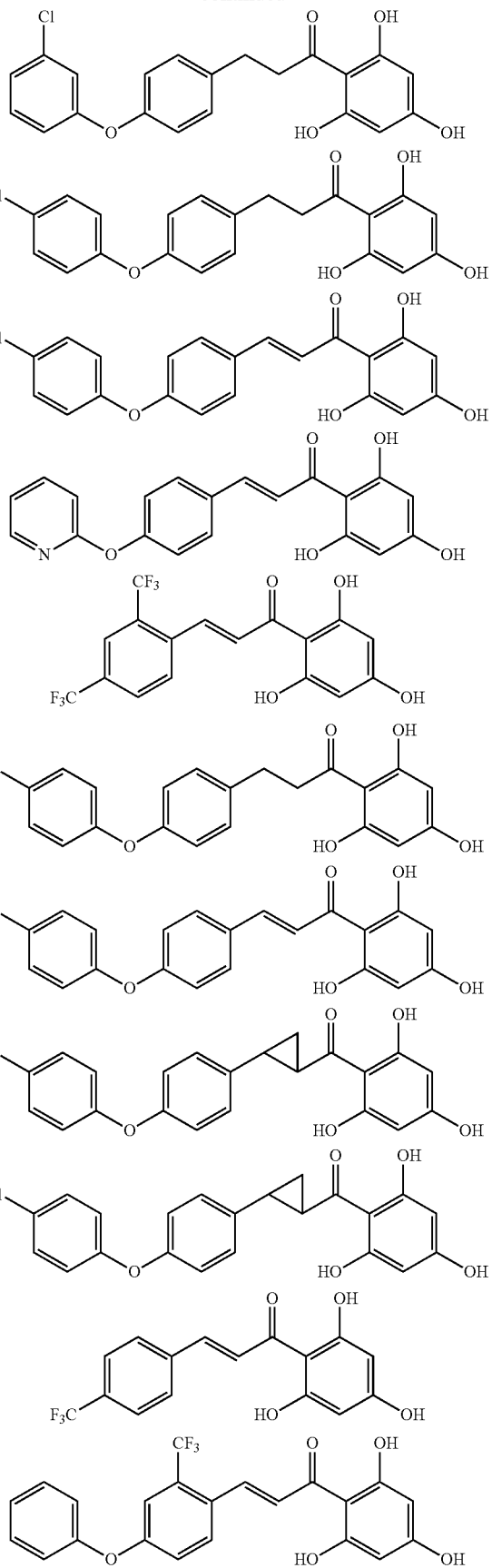

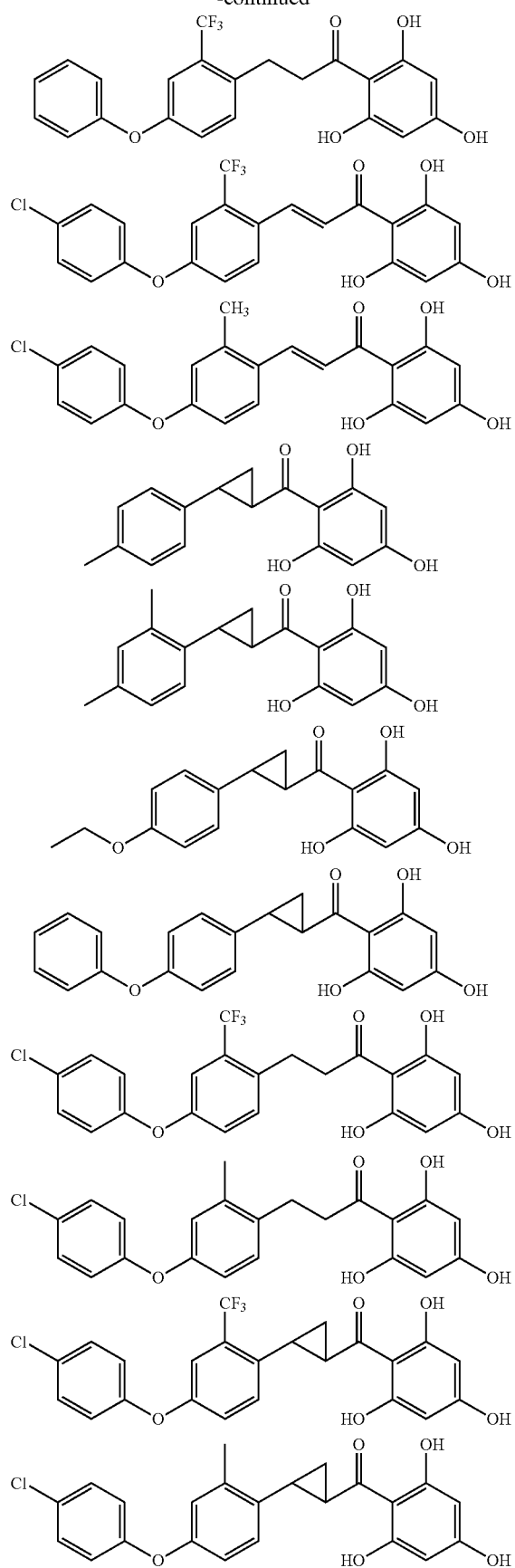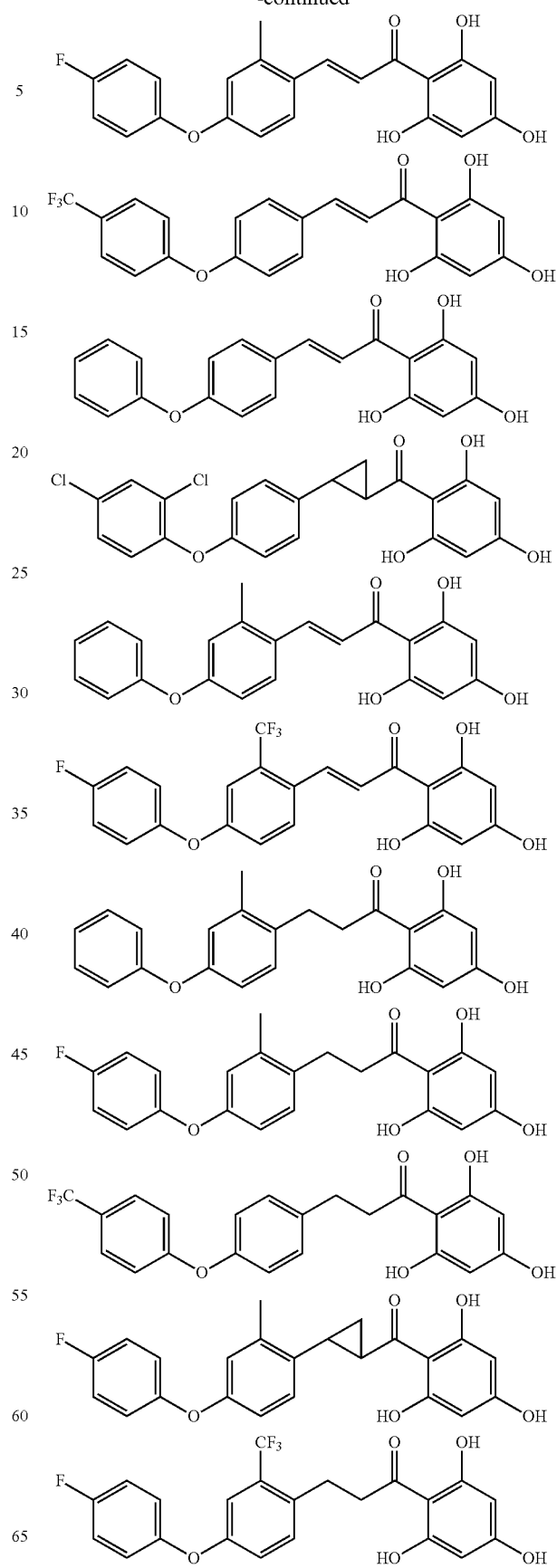

-continued
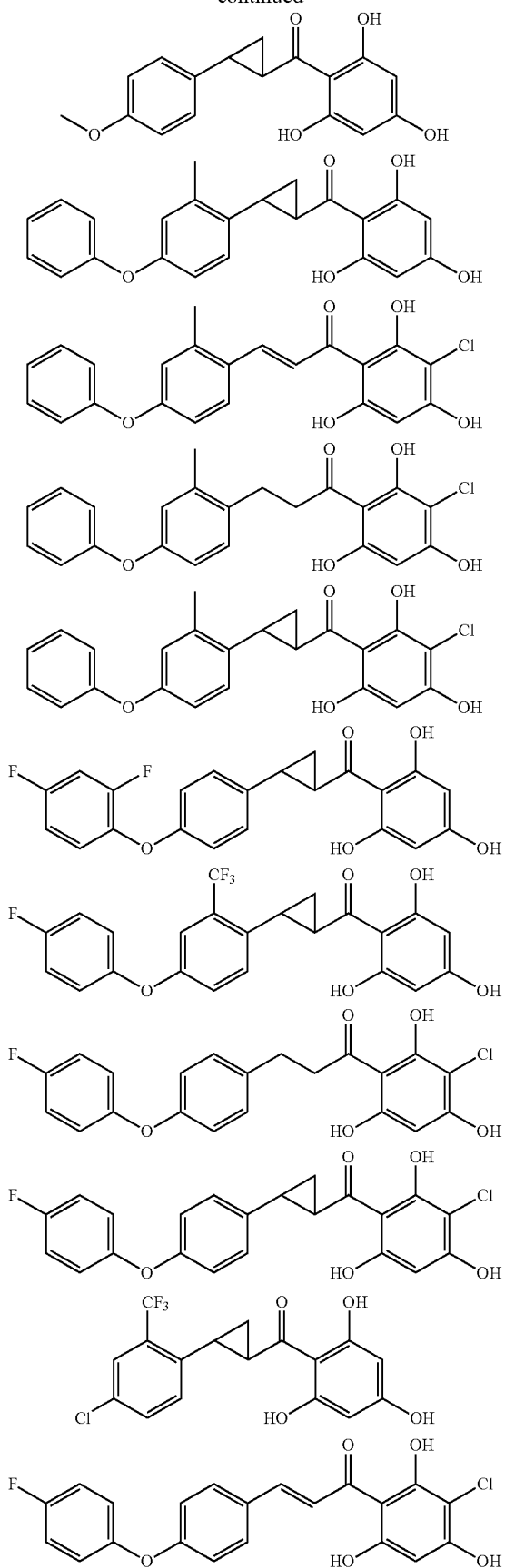
-continued
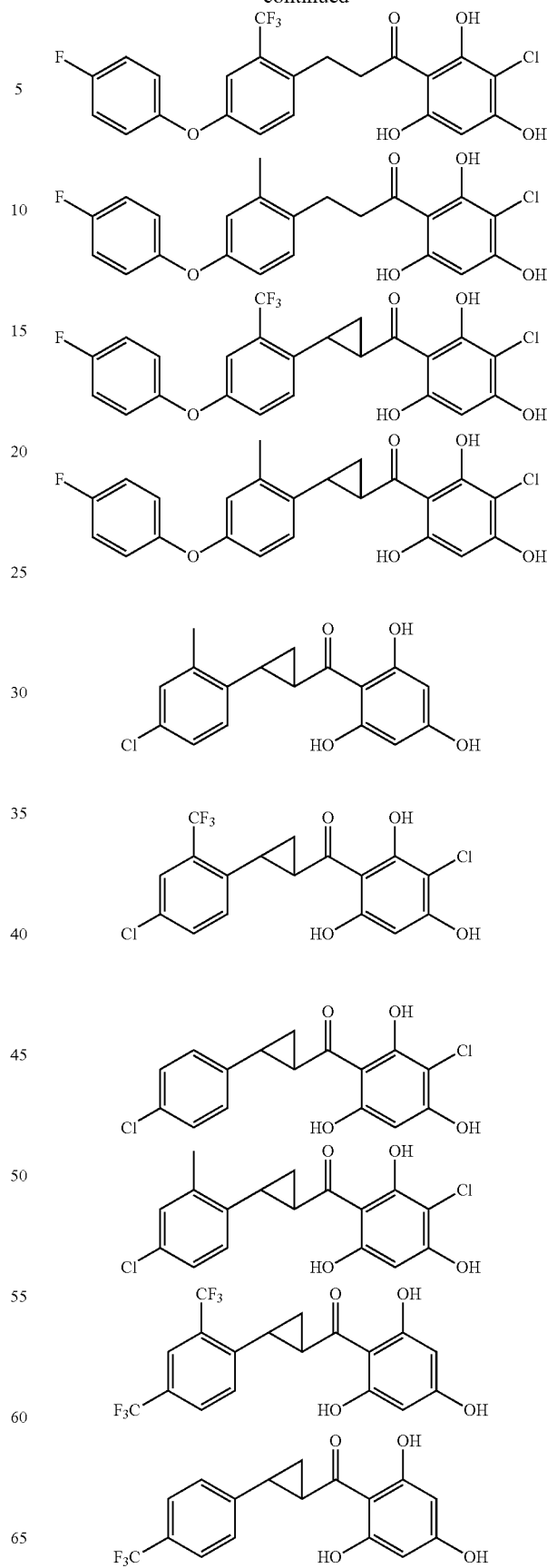

-continued
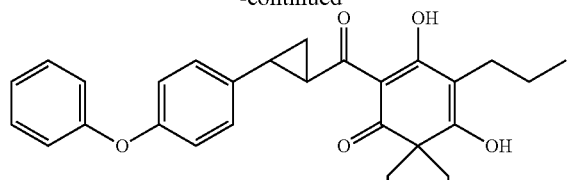
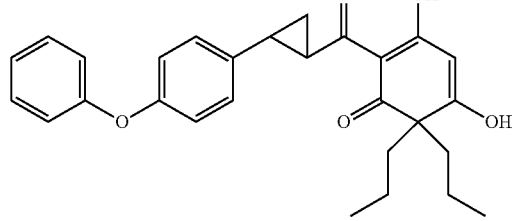
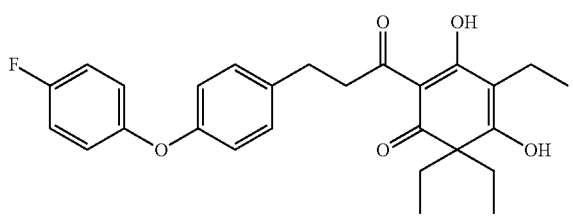
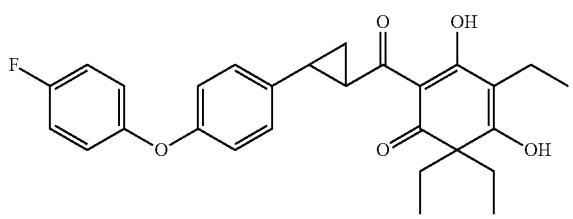
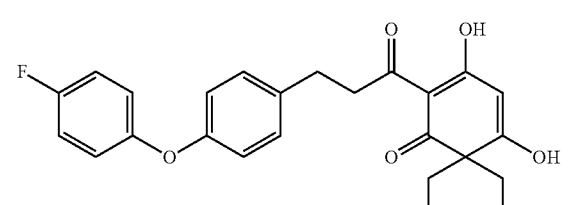
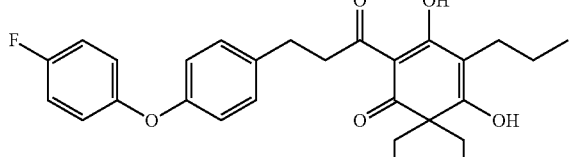
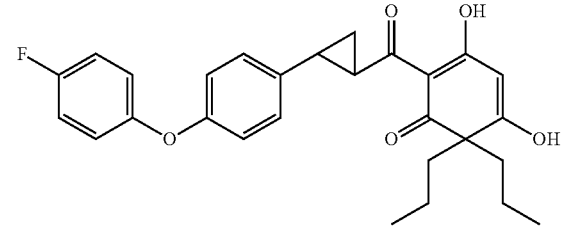
-continued
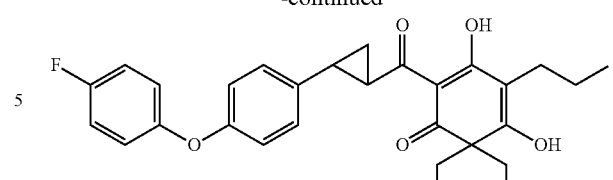
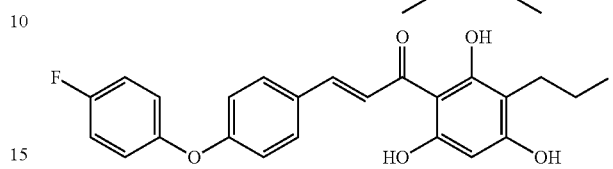
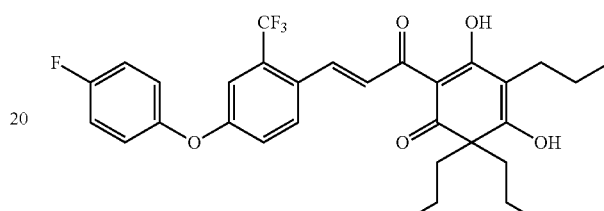
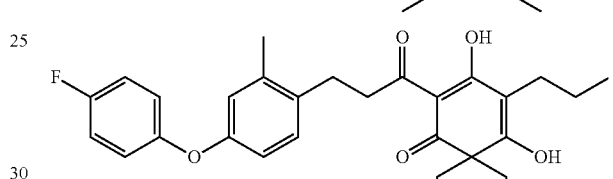
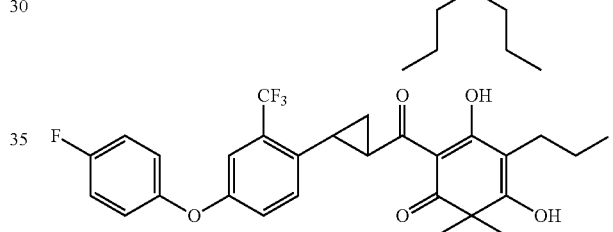
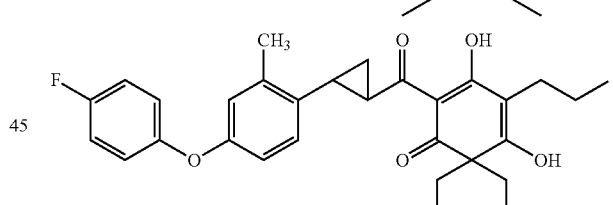
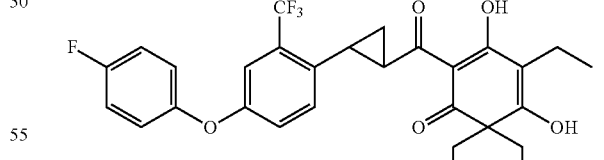
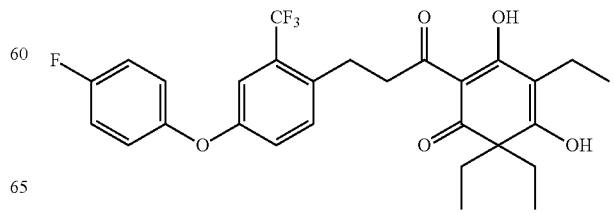

-continued
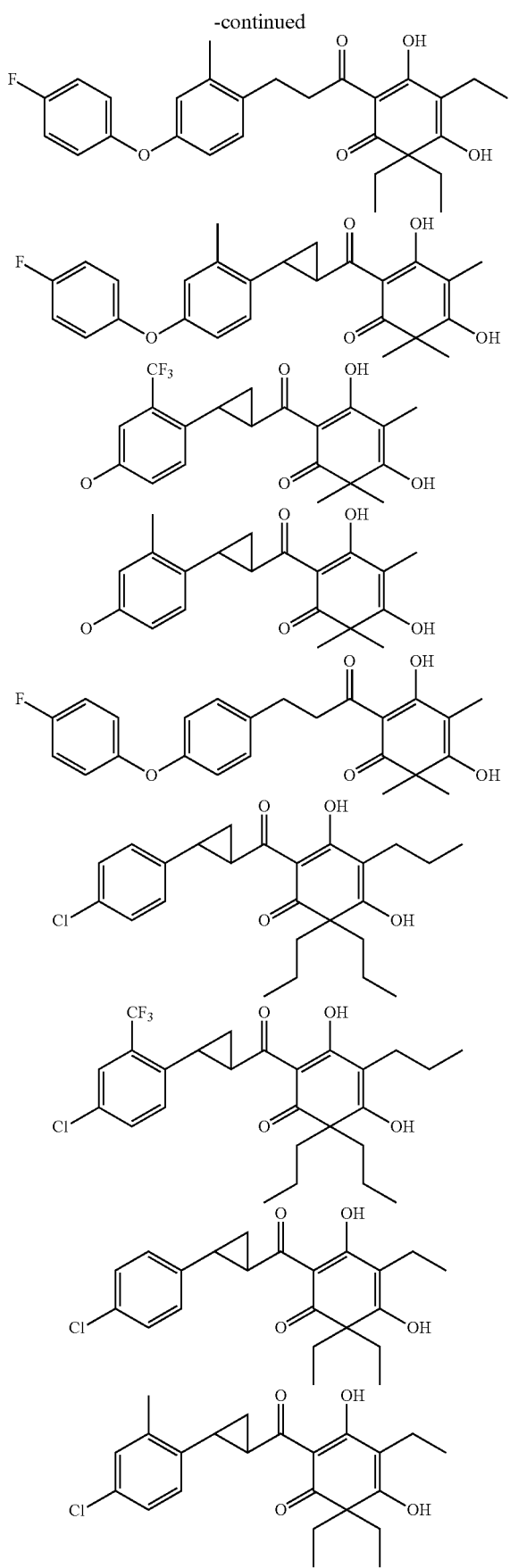
-continued
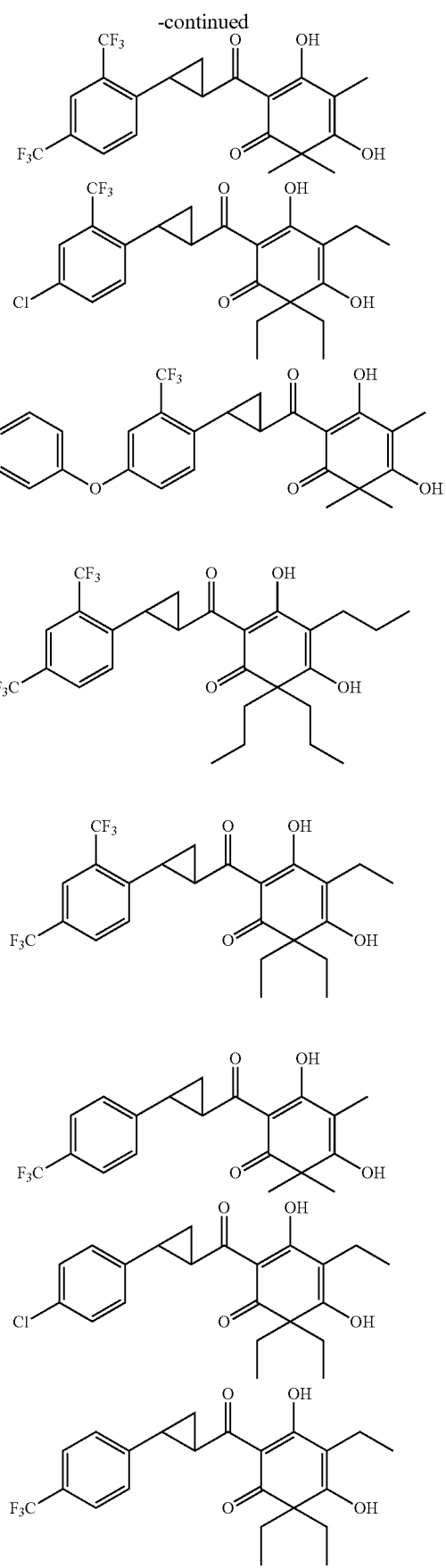

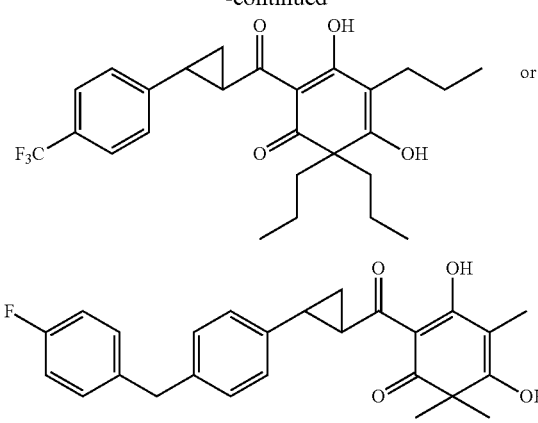
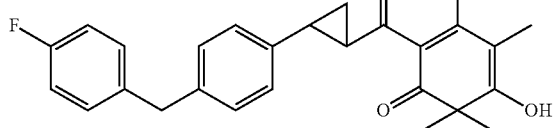
or a tautomer or salt thereof.
9. The compound, tautomer, or salt of claim 1 which is:
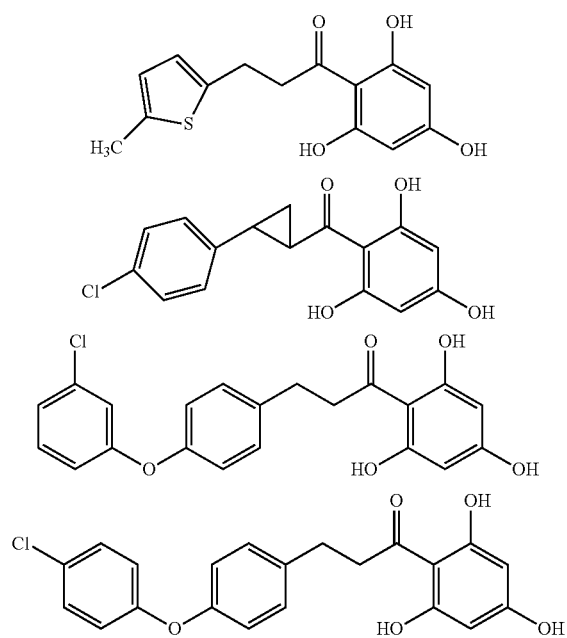
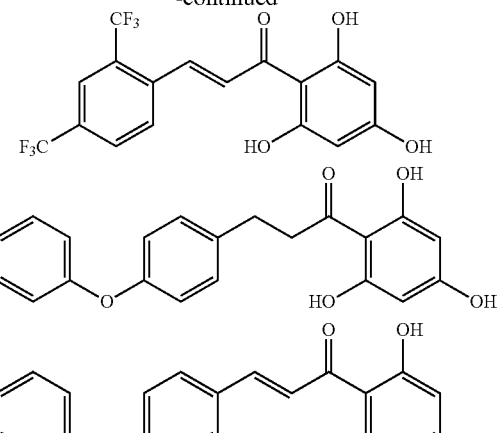
or a tautomer or salt thereof.
10. The compound:
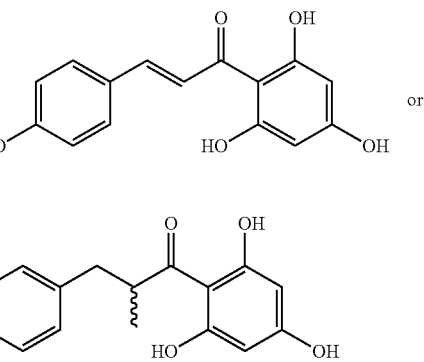
or a tautomer or a salt thereof.
11. A composition comprising a compound or tautomer as described in claim 1, or a pharmaceutically acceptable salt thereof, and a pharmaceutically acceptable vehicle.

12. A method for inhibiting a bacterial RNA polymerase comprising contacting the bacterial RNA polymerase with a compound or tautomer as described in claim 1, or a salt thereof.

13. A method for inhibiting the growth of bacteria comprising contacting the bacteria with a compound or tautomer as described in claim 1, or a salt thereof.

14. A method for treating a bacterial infection in a mammal comprising administering to the mammal an effective amount of a compound or tautomer as described in claim 1, or a pharmaceutically acceptable salt thereof.

* * * * *

UNITED STATES PATENT AND TRADEMARK OFFICE
CERTIFICATE OF CORRECTION

Page 1 of 2

PATENT NO. : 10,450,292 B2
APPLICATION NO. : 15/782002
DATED : October 22, 2019
INVENTOR(S) : Richard H. Ebright et al.

It is certified that error appears in the above-identified patent and that said Letters Patent is hereby corrected as shown below:

On the Title Page

Item (73), Assignee, please delete "Rutgers, The State University of New Jersesy" and insert
-- Rutgers, The State University of New Jersey --;

In the Claims

Column 73, Line 52, Claim 8, please delete "The compound" and insert -- The compound: --;

Column 80, Lines 15-25, Claim 8, please delete the following compound:

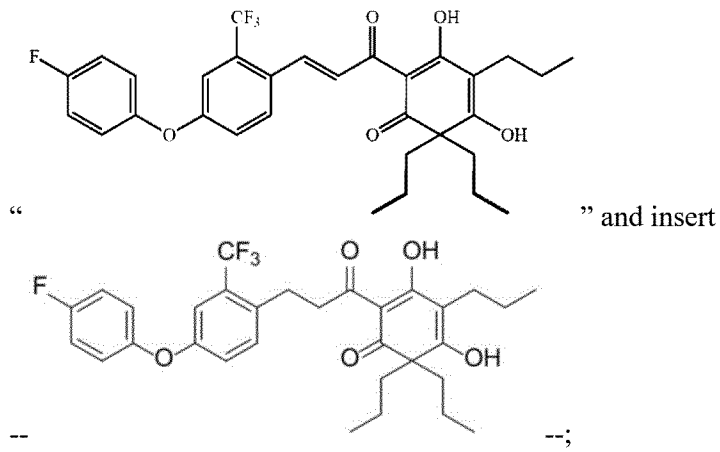

" and insert -- -- ;

Signed and Sealed this
Twenty-eighth Day of January, 2020

Andrei Iancu
*Director of the United States Patent and Trademark Office*

CERTIFICATE OF CORRECTION (continued)
U.S. Pat. No. 10,450,292 B2

Column 81, Lines 15-22, Claim 8, please delete the following compound:

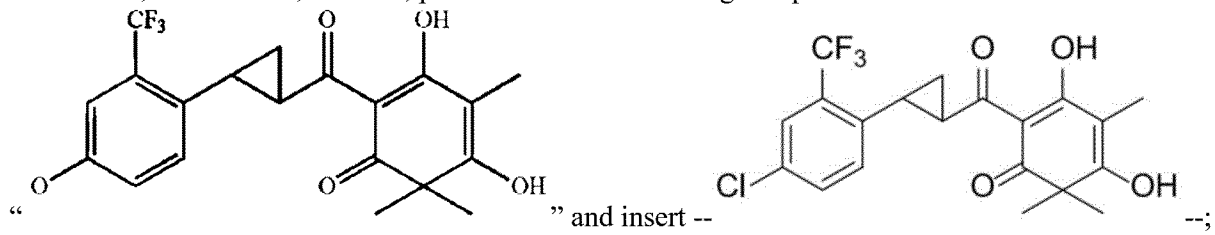

" and insert -- -- ;

Column 81, Lines 23-28, Claim 8, please delete the following compound:

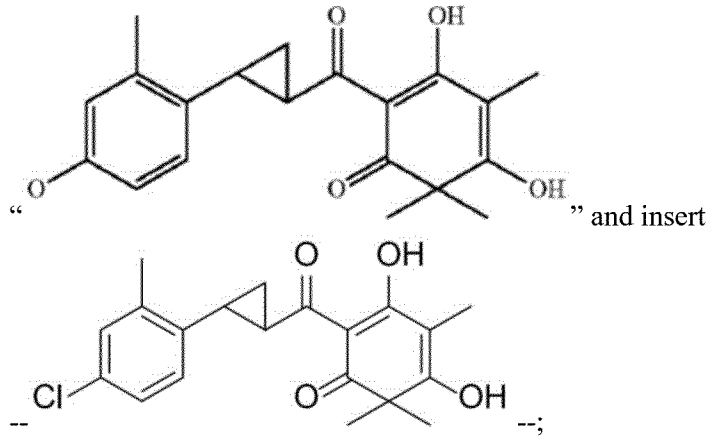

" and insert

-- -- ;

Column 83, Lines 10-18, Claim 8, please delete the following compound:

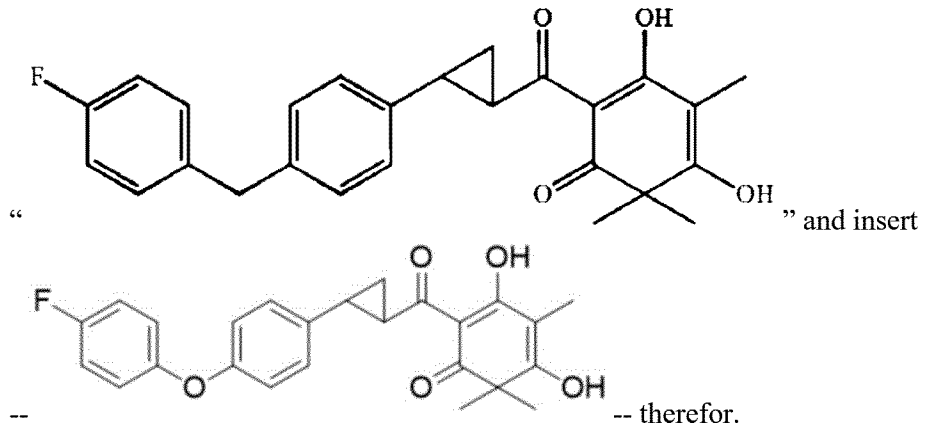

" and insert

-- -- therefor.

UNITED STATES PATENT AND TRADEMARK OFFICE
CERTIFICATE OF CORRECTION

PATENT NO. : 10,450,292 B2
APPLICATION NO. : 15/782002
DATED : October 22, 2019
INVENTOR(S) : Richard H. Ebright et al.

Page 1 of 1

It is certified that error appears in the above-identified patent and that said Letters Patent is hereby corrected as shown below:

In the Specification

Column 1, Lines 14-16, please delete "This invention was made with Government support under U19-AI109713 awarded by the National Institutes of Health. The government has certain rights in the invention." and insert -- This invention was made with Government support under AI109713 awarded by the National Institutes of Health. The government has certain rights in the invention. -- therefor.

Signed and Sealed this
Twenty-fourth Day of January, 2023

Katherine Kelly Vidal
*Director of the United States Patent and Trademark Office*